US008741287B2

(12) United States Patent
Brophy et al.

(10) Patent No.: US 8,741,287 B2
(45) Date of Patent: Jun. 3, 2014

(54) PLGF-1 ASSAY AND KITS AND COMPONENTS THEREOF

(75) Inventors: Susan E. Brophy, Lindenhurst, IL (US); Lianli Chi, Waukegan, IL (US); Saul A Datwyler, Evanston, IL (US); David J. Hawksworth, Lake Villa, IL (US); Don M. Laird, Mundelein, IL (US); Sharmila Manoj, Arlington Heights, IL (US); Mary S. Pinkus, Chicago, IL (US); Dominick L. Pucci, Libertyville, IL (US); Carol S. Ramsay, Arlington Heights, IL (US); David C. Sogin, Highland Park, IL (US); Bailin Tu, Libertyville, IL (US); Joan D. Tyner, Beach Park, IL (US); Lowell J. Tyner, legal representative, Chicago, IL (US); Zhiguang Yu, Libertyville, IL (US); Robert N. Ziemann, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 883 days.

(21) Appl. No.: 12/485,114

(22) Filed: Jun. 16, 2009

(65) Prior Publication Data

US 2010/0015637 A1  Jan. 21, 2010

Related U.S. Application Data

(60) Provisional application No. 61/073,624, filed on Jun. 18, 2008, provisional application No. 61/089,172, filed on Aug. 15, 2008.

(51) Int. Cl.
*A61K 39/395* (2006.01)
*C12Q 3/00* (2006.01)
*G01N 33/53* (2006.01)

(52) U.S. Cl.
USPC .................. 424/130.1; 424/141.1; 424/145.1; 435/4; 435/7.1

(58) Field of Classification Search
CPC ......... A61K 39/395; C12Q 3/00; G01N 33/53
USPC ............... 424/130.1, 141.1, 145.1; 435/4, 7.1
See application file for complete search history.

(56) References Cited

U.S. PATENT DOCUMENTS

| 4,554,101 A | 11/1985 | Hopp |
| 5,919,899 A | 7/1999 | Persico et al. |
| 7,767,792 B2 | 8/2010 | Johns et al. |
| 2004/0224347 A1 | 11/2004 | Love et al. |
| 2005/0070696 A1 | 3/2005 | Maglione et al. |
| 2005/0255555 A1 | 11/2005 | Johns et al. |
| 2007/0037224 A1 | 2/2007 | Hamer et al. |
| 2007/0087001 A1 | 4/2007 | Taylor et al. |
| 2007/0111326 A1 | 5/2007 | Sogin et al. |
| 2007/0254295 A1 | 11/2007 | Harvey et al. |
| 2008/0071151 A1 | 3/2008 | Sogin et al. |

FOREIGN PATENT DOCUMENTS

| EP | 0 550 519 | 11/1998 |
| EP | 1 472 286 B1 | 4/2007 |
| WO | 92/06194 A1 | 4/1992 |
| WO | 03/066676 A1 | 8/2003 |
| WO | 2005/092921 A2 | 10/2005 |
| WO | 2006/128553 A1 | 7/2006 |
| WO | 2006/102498 A2 | 9/2006 |
| WO | 2009/089271 A1 | 7/2009 |

OTHER PUBLICATIONS

Albert D.H., et al., "Preclinical Activity of ABT-889, A Multitargeted Receptor Tyrosine Kinase Inhibitor," Molecular Cancer Therapeutics, 2006, vol. 5 (4), pp. 995-1006.
Bass M.B., et al., "Placental Growth Factor as a Marker of Therapeutic Response to Treatment with Motesanib in Patients with Progressive Advanced Thyroid Cancer, Advanced Nonsquairious Non-small Cell Lung Cancer, and Locally Recurrent or Advanced Metastatic Breast Cancer, " Journal of Clinical Oncology, 2010, vol. 28.
Batchelor T.T., et al., "AZD2171, A Pan-Vegf Receptor Tyrosine Kinase Inhibitor. Normalizes Tumor Vasculature and Alleviates Edema in Glioblastoma Patients," Cancer Cell, 2007, vol. 11 (1), pp. 83-95.
Burstein H.J., et al., "Phase II Study of Sunitinib Malate, an Oral Multitargeted Tyrosine Kinase Inhibitor, in Patients with Metastatic Breast Cancer Previously Treated with an Anthracycline and a Taxane," Journal of Clinical Oncology, 2008, vol. 26 (11), pp. 1810-1816.
Chen C.N., et al., "The Significance oh Placenta Growth Factor in Angiogenesis and Clinical Outcome of Human Gastric Cancer," Cancer Letters, 2004; vol. 213 (1), pp. 73-82.
Deprimo S.E., et al., "Circulating Protein Biomarkers of Pharmacodynamic Activity of Sunitinib in Patients with Metastatic Renal Cell Carcinoma: Modulation of Vegf and Vegf-Related Proteins," Journal of Translational Medicine, 2007; vol. 5, pp. 32.
Ebos J.M., et al., "Multiple Circulating Proangiogenic Factors Induced by Sunitinib Malate are Tumor-Independent and Correlate with Antitumor Efficacy," Proceedings of the National Academy of Sciences, 2007, vol. 104 (43), pp. 17069-17074.
Grandinetti C.A , et al., "Sorafenib and Sunitinib: Novel Targeted Therapies for Renal Cell Cancer," Pharmacotherapy, 2001, vol. 27 (8), pp. 1125-1144.
Henry J.A., et al., "Prognostic Significance of the Estrogen-Regulated Protein Cathespsin D, in Breast Cancer: An Immunohistochemical Study," Cancer, 1990, vol. 65 (2), pp. 265-271.
International Search Report for Application No. PCT/US2009/47714, mailed on Sep. 15, 2009, 1 page.

(Continued)

*Primary Examiner* — Rodney P Swartz
(74) *Attorney, Agent, or Firm* — Audrey L. Bartnicki; Carol Larcher; Larcher & Chao Law Group

(57) ABSTRACT

The present disclosure relates to glycosylated and deglycosylated human PlGF-1, methods of using the glycosylated and deglycosylated human PlGF-1, antibodies that bind to human PlGF-1, methods of using the antibodies and human PlGF-1 immunoassays and kits.

20 Claims, 24 Drawing Sheets

(56) References Cited

OTHER PUBLICATIONS

Levine R.J., et al., "Urinary Placental growth Factor and Risk of Preeclampsia," Journal of the American Medical Association, 2005, vol. 293 (1), pp. 77-85.

Morabito A., et al., "Tyrosine Kinase Inhibitors of Vascular Endothelial Growth Factor Receptors in Clinical Trials: Current Status and Future Directions," Oncologist, 2006, vol. 11 (7), pp. 753-764.

Motzer R.J., et al., "Activity of SU11248, a Multitargeted Inhibitor of Vascular Endothelial Growth Factor Receptor and Platelet-Derived Growth Factor Receptor, in Patients with Metastatic Renal Cell Carcinoma," Journal of Clinical Oncology, 2006, vol. 24 (1), pp. 16-24.

Soo R.A., et al., The Effect of Varying Doses of ABT-869 on Biomarkers of Angiogensis and their Correlation with Pharmacodynamic Outcome, ASCO Annual Meeting [online], 2008 [retrieved on Feb. 29, 2012]. Retrieved from the Internet.<URL: http://tinyurl.com/847l6aq>.

Stein M.N., et al., "Sorafenib and Sunitinib in Renal Cell Carcinoma," Clinical Cancer Research, 2007, vol. 13 (13), pp. 3765-3770.

Supplementary European Search Report for Application No. EP09767690, mailed on Mar. 13, 2012, 2 pages.

Tsatsaris V., et al., "Overexpression of the Soluble Vascular Endothelial Growth Factor Receptor in Preeclamptic Patients: Pathophysiological Consequences," Journal of Clinical Endocrinology and Metabolism, 2003, vol. 88 (11), pp. 5555-5563.

Wei S.C., et al., "Preoperative Serum Placenta Growth Factor Level is a Prognostic Biomarker in Colorectal Cancer," Diseases of the Colon and Rectum, 2009, vol. 52 (9), pp. 1630-1636.

Wilhelm S., et al., "Discovery and Development of Sorafenib: a Multikinase Inhibitor for Treating Cancer," Nature Reviews, Drug Discovery, 2006, vol. 5 (10), pp. 835-844.

Willett C.G., et al., "Surrogate Markers for Antiangiogenic Therapy and Dose-Limiting Toxicities for Bevacizumab with Radiation and Chemotherapy: Continued Experience of a Phase I Trial in Rectal Cancer Patients," Journal of Clinical Oncology, 2005, vol. 23 (31), pp. 8136-8139.

Written Opinion for Application No. PCT/US2009/047714, mailed on Sep. 15, 2009, 9 pages.

Zhu A.X., "Development of Sorafenib and Other Molecularly Targeted Agents in Hepatocellular Carcinoma," Cancer, 2008, vol. 112 (2), pp. 250-259.

Bird, et al. "Single-Chain Antigen-Binding Proteins," Science 21, 242:4877, (1998), pp. 423-426.

De Falco, et al., "Structure and Function of Placental Growth Factor," Trends Cardiovascular Medicine, 12:6. (2002), pp. 241-246.

Errico, M., "Identification of placenta growth factore determinants for binding and activation of Flt-1 receptor". The Journal of Bological Chemistry, vol. 279, 2004, No. 42, pp. 43929-43939.

Ferrara, N., "Vascular Endothelial Growth Factor: Basic Science and Clinical Progress." Endocrine Reviews. 25:4. (2004), pp. 581-611.

Heeschen, et al., "Prognostic Value of Placental Growth Factor in Patients With Acute Chest Pains," Journal of the American Medical Association, 291:4, (2004), pp. 435-441.

Huston. et al., "Protein engineering of binding sites: Recovery of specific activity in an anti-digoxin single-chain Fv analogue produced in *Escherichia coli*," Proc. Natl. Sci. USA, 85, (1988), pp. 5879-5883.

Iyer, et al., "The Crystal Structure of Human Placenta Growth Factor-1 (PlGF-1), an Angiogenic Protein, at 2.0 A Resolution," The Journal of Biological Chemistry, 276:15, (2001), pp. 12153-12161.

Kohler, et al. "Continuous cultures of fused cells secreting antibody of predefined specificity." Nature, 256, (1975) pp. 495-497.

Kozak, M., "At Least Six Nucleotides Preceding the AUG Initiator Codon Enhance Translation in Mammalian Cells," J. Mol. Biol. 196, (1987), pp. 947-950.

Kozbor, et al., "The production of monoclonal antibodies from human lymphocytes," Immunology Today, 4:3, (1983), pp. 72-79.

Kumazaki, et al., "Expression of Vascular Endothelial Growth Factor, and Their Receptors Flt-1 and KDR in Human Placenta Under Pathologic Conditions," Human Pathology, 33:11, (2002), pp. 1069-1077.

Maglione, et al., "Isolation of a human placenta, cDNA coding for a protein related to the vascular permeability factor," Proc. Natl. Acad. Sci., 88, (1991) pp. 9267-9271.

McCafferty, et al., "Phage antibodies: filamentous phage displaying antibody variable domains." Nature, 348.6, (1990), pp. 552-554.

Nelson, et al., "A General Method of Site-Specific Mutagenesis Using a Modification of the Thermus aquaticus Polymerase Chain Reaction," Analytical Biochemistry, 180, (1989), pp. 147-151.

OriGene Technologies, Inc., Certificate of Analysis, "Human cDNA Clone," Catalog No. SC118512, 2010.

PCT/US2009/047623 International Search Report and Written Opinion of the EP International Searching Authority, mailed Dec. 30, 2009.

R & D Systems®, Inc., "Anti-human PlGF Detection Antibody," Catalog No. AB-264-PB, Product Insert Sheet, Release Date Sep. 24, 2009.

R & D Systems®, Inc., "Monoclonal Anti-human PlGF Antibody," Catalog No. MAB264, Product Insert Sheet, Release Date Mar. 18, 2009.

R & D Systems®, Inc., Quantikine®, Human PlGF Immunoassay. Catalog Nos. DPG00, SPG00, PDPG00, Product Sheet, Release Date Jun. 2008.

R & D Systems®, Inc., "Recombinanat Human PlGF," Catalog No. 264-PG-CF. Product Insert Sheet, Release Date Jul. 22, 2009.

Roeckl, et al., "Differential Binding Characteristics and Cellular Inhibition by Soluble VEGF Receptors 1 and 2." Experimental Cell Research, 241. (1998), pp. 161-170.

Schmidt, "Altered angiogenesis in preeclampsia: Evaluation of a new test system for measuring placental growth factor", Clinical Chemistry and Laboratory Medicine, vol. 45, No. 211, 2007, pp. 1504-1510.

Su, et al., "Raised maternal serum placenta growth factor concentration during the second trimester is associated with Down syndrome." Prenatal Diagnosis, 22:1, (2002) pp. 8-12.

Wands, et al., "High Affinity Monoclonal Antibodies to Hepatitis B Surface Antigen (HBsAg) Produced by Somatic Cell Hybrids." Gastroenterology, 80, (1981), pp. 225-232.

5'-
*ATGGACATGCGCGTGCCCGCCCAGCTGCTGGGCCTGCTGCTGCTGTGGTTCCCCGGC
TCGCGATGC*CATCATCACCATCACCATCTGCCTGCTGTGCCCCCCCAGCAGTGGG
CCTTGTCTGCTGGGAACGGCTCGTCAGAGGTGGAAGTGGTACCCTTCCAGGAAGT
GTGGGGCCGCAGCTACTGCCGGGCGCTGGAGAGGCTGGTGGACGTCGTGTCCGA
GTACCCCAGCGAGGTGGAGCACATGTTCAGCCCATCCTGTGTCTCCCTGCTGCGC
TGCACCGGCTGCTGCGGCGATGAGAATCTGCACTGTGTGCCGGTGGAGACGGCC
AATGTCACCATGCAGCTCCTAAAGATCCGTTCTGGGGACCGGCCCTCCTACGTGG
AGCTGACGTTCTCTCAGCACGTTCGCTGCGAATGCCGGCCTCTGCGGGAGAAGAT
GAAGCCGGAAAGGTGCGGCGATGCTGTTCCCCGGAGG-3'

FIGURE 1

5'-
*ATGGACATGCGCGTGCCCGCCCAGCTGCTGGGCCTGCTGCTGCTGTGGTTCC
CCGGCTCGCGATGC*<u>CATCATCACCATCACCAT</u>TCGTCAGAGGTGGAAGTGGTA
CCCTTCCAGGAAGTGTGGGGCCGCAGCTACTGCCGGGCGCTGGAGAGGCTGG
TGGACGTCGTGTCCGAGTACCCCAGCGAGGTGGAGCACATGTTCAGCCCATCC
TGTGTCTCCCTGCTGCGCTGCACCGGCTGCTGCGGCGATGAGAATCTGCACTG
TGTGCCGGTGGAGACGGCCAATGTCACCATGCAGCTCCTAAAGATCCGTTCTG
GGGACCGGCCCTCCTACGTGGAGCTGACGTTCTCTCAGCACGTTCGCTGCGAA
TGCCGGCCTCTGCGGGAGAAGATGAAGCCGGAAAGGTGCGGCGATGCTGTTC
CCCGGAGG-3'

FIGURE 6

5'-
*ATGGACATGCGCGTGCCCGCCCAGCTGCTGGGCCTGCTGCTGCTGTGGTTCCCCGGC TCGCGATGC*<u>CATCATCACCATCACCAT</u>GGTGACGATGACGACGACAAGCTGCCT GCTGTGCCCCCCAGCAGTGGGCCTTGTCTGCTGGGAACGGCTCGTCAGAGGTGG AAGTGGTACCCTTCCAGGAAGTGTGGGGCCGCAGCTACTGCCGGGCGCTGGAGA GGCTGGTGGACGTCGTGTCCGAGTACCCCAGCGAGGTGGAGCACATGTTCAGCC CATCCTGTGTCTCCCTGCTGCGCTGCACCGGCTGCTGCGGCGATGAGAATCTGCA CTGTGTGCCGGTGGAGACGGCCAATGTCACCATGCAGCTCCTAAAGATCCGTTCT GGGGACCGGCCCTCCTACGTGGAGCTGACGTTCTCTCAGCACGTTCGCTGCGAAT GCCGGCCTCTGCGGGAGAAGATGAAGCCGGAAAGGTGCGGCGATGCTGTTCCCC GGAGG-3'

FIGURE 9

```
1    GATGTTGTG ATGACCCAA ACTCCACTC TCCCTACCT GTCAGTCCT GGAGATCAA
     CTACAACAC TACTGGGTT TGAGGTGAG AGGGATGGA CAGTCAGGA CCTCTAGTT

CDR L1 (15 a.a.)
                 ~~~~~~~~~~~~~~~~~~~~~~~~~~~~~~~~~~~~~~~~
55   GCCTCCATC TCTTGCAGA TCTAGTCAG AGCCTTGTA CACAGTAAT GGACACACC
     CGGAGGTAG AGAACGTCT AGATCAGTC TCGGAACAT GTGTCATTA CCTGTGTGG

CDR L1 (15 a.a.)
     ~~~~~~~~~~
109  TATTTACAT TGGTACCTG CAGAAGCCA GGCCAGTCT CCAAAGCTC CTGATCTAC
     ATAAATGTA ACCATGGAC GTCTTCGGT CCGGTCAGA GGTTTCGAG GACTAGATG

CDR L2 (7 a.a.)
     ~~~~~~~~~~~~~~~~~~~~~~~
163  AAAGTTTCC AACCGATTT TCTGGGGTC CCCGACAGG GTCAGTGGC AGTGGATCA
     TTTCAAAGG TTGGCTAAA AGACCCCAG GGGCTGTCC CAGTCACCG TCACCTAGT

217  GGGACAGAT TTCACACTC AAGATCAGC AGAGTGGAG GCTGAGGAT CTGGGAGTT
     CCCTGTCTA AAGTGTGAG TTCTAGTCG TCTCACCTC CGACTCCTA GACCCTCAA

CDR L3 (9 a.a.)
                 ~~~~~~~~~~~~~~~~~~~~~~~~~~~~~~
271  TATTTCTGC TCTCAAAGT ACACATGTT CCTCCGACG TTCGGTGGA GGCACCAAG
     ATAAAGACG AGAGTTTCA TGTGTACAA GGAGGCTGC AAGCCACCT CCGTGGTTC

325  CTGGAAATC AAACGG
     GACCTTTAG TTTGCC
```

FIGURE 12

```
1    DVVMTQTPLS LPVSPGDQAS ISCRSSQSLV HSNGHTYLHW YLQKPGQSPK
51   LLIYKVSNRF SGVPDRVSGS GSGTDFTLKI SRVEAEDLGV YFCSQSTHVP
101  PTFGGGTKLE IKR
```

FIGURE 13

```
1     CAGGTTCAC CTGCAGCAG TCTGGAGCT GAGCTGATG AAGCCTGGG GCCTCAGTG
      GTCCAAGTG GACGTCGTC AGACCTCGA CTCGACTAC TTCGGACCC CGGAGTCAC

CDR H1 (10a.a.)
                              ~~~~~~~~~~~~~~~~~~~~~~~~~~~~~~~~
55    AAGATATCC TGCAAGGCT ACTGGCTAC ACATTCAGT AGCTACTGG ATAGAGTGG
      TTCTATAGG ACGTTCCGA TGACCGATG TGTAAGTCA TCGATGACC TATCTCACC

CDR H2 (17a.a.)
                                                     ~~~~~~~~~~~~~~~~~
109   GTAAAGCAG AGGCCTGGA CATGGCCTT GAGTGGATT GGAGAGATT TTACCTGGA
      CATTTCGTC TCCGGACCT GTACCGGAA CTCACCTAA CCTCTCTAA AATGGACCT

CDR H2 (17a.a.)
      ~~~~~~~~~~~~~~~~~~~~~~~~~~~~~~~~~~~~~~~~
163   AGTGTAAGT AATAATTTC AATGAGAAG TTCAAGGAC AAGGCCACA CTCACTGCA
      TCACATTCA TTATTAAAG TTACTCTTC AAGTTCCTG TTCCGGTGT GAGTGACGT

217   GATCCTTCC TCCAACACA GCCTACATA CAAGTCAGC AGCCTGACA TCTGAGGAC
      CTAGGAAGG AGGTTGTGT CGGATGTAT GTTCAGTCG TCGGACTGT AGACTCCTG

CDR H3 (13a.a.)
                                   ~~~~~~~~~~~~~~~~~~~~~~~~~~~~~~~~~~
271   TCTGCCGTC TATTACTGT GCAAGATCA ACGGGCTTT TACTACGGG GGTAACTAC
      AGACGGCAG ATAATGACA CGTTCTAGT TGCCCGAAA ATGATGCCC CCATTGATG

CDR H3 (13a.a.)
      ~~~~~~~~~~
325   TTTGACCAC TGGGGCCAA GGCACCACT CTCGCAGTC TCCTCA
      AAACTGGTG ACCCCGGTT CCGTGGTGA GAGCGTCAG AGGAGT
```

FIGURE 14

1    QVHLQQSGAE LMKPGASVKI SCKAT*GYTFS SYWIE*WVKQR PGHGLEWIG*E*
51   *ILPGSVSNNF NEKFKD*KATL TADPSSNTAY IQVSSLTSED SAVYYCAR*ST*
101  *GFYYGGNYFD H*WGQGTTLAV SS

FIGURE 15

```
1    GCCATC CAGATG ACTCAG TCTTCA TCCTCC TTTTCT GTATCT CTGGGA GACAGA
     CGGTAG GTCTAC TGAGTC AGAAGT AGGAGG AAAAGA CATAGA GACCCT CTGTCT

CDR-L1 (11aa)
                     ~~~~~~~~~~~~~~~~~~~~~~~~~~~~~~~~~~~
  55 GTCACC ATTACT TGCAAG GCAAGT GAGGAC ATATAT AATCGG TTCGCC TGGTAT
     CAGTGG TAATGA ACGTTC CGTTCA CTCCTG TATATA TTAGCC AAGCGG ACCATA

CDR-L2 (7aa)
                                                      ~~~~~~~~~~~~~~~~~~
 109 CAGCAG AAACCC GGAAAT GCTCCT AGGCTC TTAATA TCTGGT GCAGCC AGTTTG
     GTCGTC TTTGGG CCTTTA CGAGGA TCCGAG AATTAT AGACCA CGTCGG TCAAAC

CDR-L2 (7aa)
     ~~~~~~
 163 GAAGCT GGGGTT CCTTCA AGATTC AGTGGC AGTGGA TCTGGA CAGGAT TACACT
     CTTCGA CCCCAA GGAAGT TCTAAG TCACCG TCACCT AGACCT GTCCTA ATGTGA

CDR-L3
     (9aa)
                                                               ~~~~~~
 217 CTCAGC ATTACC AGTCTT CAGACT GAAGAT GTTGCT ACTTAT TACTGT CAACAG
     GAGTCG TAATGG TCAGAA GTCTGA CTTCTA CAACGA TGAATA ATGACA GTTGTC

CDR-L3 (9aa)
     ~~~~~~~~~~~~~~~~~~~~~~~~
 271 TATTGG AGTACT CCGTGG ACGTTC GGTGGA GGCACC AAGCTG GAAATC AAACGG
     ATAACC TCATGA GGCACC TGCAAG CCACCT CCGTGG TTCGAC CTTTAG TTTGCC
```

FIGURE 16

```
  1    AIQMTQSSSS FSVSLGDRVT ITCKASEDIY NRFAWYQQKP GNAPRLLISG
 51    AASLEAGVPS RFSGSGSGQD YTLSITSLQT EDVATYYCQQ YWSTPWTFGG
101    GTKLEIKR
```

FIGURE 17

```
1     CAGGTGCAG CTGAAGCAG TCAGGACCT GGCCTTGTG CAGCCCTCA CAGAGCCTG
      GTCCACGTC GACTTCGTC AGTCCTGGA CCGGAACAC GTCGGGAGT GTCTCGGAC

CDR H1 (10a.a.)
                            ~~~~~~~~~~~~~~~~~~~~~~~~~~~~~~~
55    TCCATCACC TGCACAGTC TCTGGTTTC TCATTGACT ACGTATGGT ATACACTGG
      AGGTAGTGG ACGTGTCAG AGACCAAAG AGTAACTGA TGCATACCA TATGTGACC

CDR H2 (16a.a.)
                                              ~~~~~~~~~~~~~~~~~
109   GTTCGCCAG TCCCCAGGA AAGGGTCTG GAGTGGCTG GGAGTGATG TGGAGTGGT
      CAAGCGGTC AGGGGTCCT TTCCCAGAC CTCACCGAC CCTCACTAC ACCTCACCA

CDR H2 (16a.a.)
      ~~~~~~~~~~~~~~~~~~~~~~~~~~~~~~~~~~
163   GGAGACACA GACTATGAT GCAGCTTTC ATATCCAGA CTGAGCATC AGCAAGGAC
      CCTCTGTGT CTGATACTA CGTCGAAAG TATAGGTCT GACTCGTAG TCGTTCCTG

217   AATTCCAAG AGCCAAGTT TTCTTTAAA ATGAACAGT CTGCAAGCT AATGACACA
      TTAAGGTTC TCGGTTCAA AAGAAATTT TACTTGTCA GACGTTCGA TTACTGTGT

CDR H3 (8a.a.)
                                   ~~~~~~~~~~~~~~~~~~~~~~~~~~~
271   GGCATATAT TACTGTGCC AGATATAGG TTCTATGGT ATGGACTAC TGGGGTCAA
      CCGTATATA ATGACACGG TCTATATCC AAGATACCA TACCTGATG ACCCCAGTT

325   GGAACCTCA GTCACCGTC TCCTCA
      CCTTGGAGT CAGTGGCAG AGGAGT
```

FIGURE 18

```
1    QVQLKQSGPG LVQPSQSLSI TCTVSGFSLT TYGIHWVRQS PGKGLEWLGV
51   MWSGGDTDYD AAFISRLSIS KDNSKSQVFF KMNSLQANDT GIYYCARYRF
101  YGMDYWGQGT SVTVSS
```

FIGURE 19

HHHHHHHLPAV PPQQWALSAG *D*GSSEVEVVP FQEVWGRSYC
RALERLVDVV SEYPSEVEHM FSPSCVSLLR CTGCCGDENL
HCVPVETAN(D)V TMQLLKIRSG DRPSYVELTF SQHVRCECRP
LREKMKPERC GDAVPRR

FIGURE 20

SEQUENCE LISTING

<160> NUMBER OF SEQ ID NOS: 43

<210> SEQ ID NO 1
<211> LENGTH: 131
<212> TYPE: PRT
<213> ORGANISM: Homo sapiens

<400> SEQUENCE: 1

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

```
Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
 50                  55                  60

Cys Thr Gly Cys Cys Gly Asp Glu Asn Leu His Cys Val Pro Val Glu
 65                  70                  75                  80

Thr Ala Asn Val Thr Met Gln Leu Leu Lys Ile Arg Ser Gly Asp Arg
                 85                  90                  95

Pro Ser Tyr Val Glu Leu Thr Phe Ser Gln His Val Arg Cys Glu Cys
                100                 105                 110

Arg Pro Leu Arg Glu Lys Met Lys Pro Glu Arg Cys Gly Asp Ala Val
            115                 120                 125

Pro Arg Arg
    130

<210> SEQ ID NO 2
<211> LENGTH: 137
<212> TYPE: PRT
<213> ORGANISM: Homo sapiens

<400> SEQUENCE: 2

His His His His His His Leu Pro Ala Val Pro Pro Gln Gln Trp Ala
 1               5                  10                  15

Leu Ser Ala Gly Asn Gly Ser Ser Glu Val Glu Val Val Pro Phe Gln
             20                  25                  30

Glu Val Trp Gly Arg Ser Tyr Cys Arg Ala Leu Glu Arg Leu Val Asp
            35                  40                  45

Val Val Ser Glu Tyr Pro Ser Glu Val Glu His Met Phe Ser Pro Ser
 50                  55                  60

Cys Val Ser Leu Leu Arg Cys Thr Gly Cys Cys Gly Asp Glu Asn Leu
 65                  70                  75                  80

His Cys Val Pro Val Glu Thr Ala Asn Val Thr Met Gln Leu Leu Lys
                 85                  90                  95

Ile Arg Ser Gly Asp Arg Pro Ser Tyr Val Glu Leu Thr Phe Ser Gln
                100                 105                 110

His Val Arg Cys Glu Cys Arg Pro Leu Arg Glu Lys Met Lys Pro Glu
            115                 120                 125

Arg Cys Gly Asp Ala Val Pro Arg Arg
        130                 135

<210> SEQ ID NO 3
<211> LENGTH: 138
<212> TYPE: PRT
<213> ORGANISM: Homo sapiens

<400> SEQUENCE: 3

Gly Ala Asp Asp Asp Asp Lys Leu Pro Ala Val Pro Pro Gln Gln Trp
 1               5                  10                  15

Ala Leu Ser Ala Gly Asn Gly Ser Ser Glu Val Glu Val Val Pro Phe
             20                  25                  30

Gln Glu Val Trp Gly Arg Ser Tyr Cys Arg Ala Leu Glu Arg Leu Val
            35                  40                  45

Asp Val Val Ser Glu Tyr Pro Ser Glu Val Glu His Met Phe Ser Pro
 50                  55                  60

Ser Cys Val Ser Leu Leu Arg Cys Thr Gly Cys Cys Gly Asp Glu Asn
 65                  70                  75                  80
```

```
Leu His Cys Val Pro Val Glu Thr Ala Asn Val Thr Met Gln Leu Leu
                85                  90                  95
Lys Ile Arg Ser Gly Asp Arg Pro Ser Tyr Val Glu Leu Thr Phe Ser
            100                 105                 110
Gln His Val Arg Cys Glu Cys Arg Pro Leu Arg Glu Lys Met Lys Pro
        115                 120                 125
Glu Arg Cys Gly Asp Ala Val Pro Arg Arg
    130                 135

<210> SEQ ID NO 4
<211> LENGTH: 144
<212> TYPE: PRT
<213> ORGANISM: Homo sapiens

<400> SEQUENCE: 4

His His His His His Gly Ala Asp Asp Asp Asp Lys Leu Pro Ala
1               5                   10                  15
Val Pro Pro Gln Gln Trp Ala Leu Ser Ala Gly Asn Gly Ser Ser Glu
            20                  25                  30
Val Glu Val Val Pro Phe Gln Glu Val Trp Gly Arg Ser Tyr Cys Arg
        35                  40                  45
Ala Leu Glu Arg Leu Val Asp Val Val Ser Glu Tyr Pro Ser Glu Val
    50                  55                  60
Glu His Met Phe Ser Pro Ser Cys Val Ser Leu Arg Cys Thr Gly
65                  70                  75                  80
Cys Cys Gly Asp Glu Asn Leu His Cys Val Pro Val Glu Thr Ala Asn
                85                  90                  95
Val Thr Met Gln Leu Leu Lys Ile Arg Ser Gly Asp Arg Pro Ser Tyr
            100                 105                 110
Val Glu Leu Thr Phe Ser Gln His Val Arg Cys Glu Cys Arg Pro Leu
        115                 120                 125
Arg Glu Lys Met Lys Pro Glu Arg Cys Gly Asp Ala Val Pro Arg Arg
    130                 135                 140

<210> SEQ ID NO 5
<211> LENGTH: 115
<212> TYPE: PRT
<213> ORGANISM: Homo sapiens

<400> SEQUENCE: 5

Ser Ser Glu Val Glu Val Val Pro Phe Gln Glu Val Trp Gly Arg Ser
1               5                   10                  15
Tyr Cys Arg Ala Leu Glu Arg Leu Val Asp Val Val Ser Glu Tyr Pro
            20                  25                  30
Ser Glu Val Glu His Met Phe Ser Pro Ser Cys Val Ser Leu Leu Arg
        35                  40                  45
Cys Thr Gly Cys Cys Gly Asp Glu Asn Leu His Cys Val Pro Val Glu
    50                  55                  60
Thr Ala Asn Val Thr Met Gln Leu Leu Lys Ile Arg Ser Gly Asp Arg
65                  70                  75                  80
Pro Ser Tyr Val Glu Leu Thr Phe Ser Gln His Val Arg Cys Glu Cys
                85                  90                  95
Arg Pro Leu Arg Glu Lys Met Lys Pro Glu Arg Cys Gly Asp Ala Val
            100                 105                 110
Pro Arg Arg
    115
```

```
<210> SEQ ID NO 6
<211> LENGTH: 121
<212> TYPE: PRT
<213> ORGANISM: Homo sapiens

<400> SEQUENCE: 6

His His His His His His Ser Ser Glu Val Glu Val Pro Phe Gln
1               5                   10                  15

Glu Val Trp Gly Arg Ser Tyr Cys Arg Ala Leu Glu Arg Leu Val Asp
            20                  25                  30

Val Val Ser Glu Tyr Pro Ser Glu Val Glu His Met Phe Ser Pro Ser
        35                  40                  45

Cys Val Ser Leu Leu Arg Cys Thr Gly Cys Cys Gly Asp Glu Asn Leu
    50                  55                  60

His Cys Val Pro Val Glu Thr Ala Asn Val Thr Met Gln Leu Leu Lys
65                  70                  75                  80

Ile Arg Ser Gly Asp Arg Pro Ser Tyr Val Glu Leu Thr Phe Ser Gln
                85                  90                  95

His Val Arg Cys Glu Cys Arg Pro Leu Arg Glu Lys Met Lys Pro Glu
            100                 105                 110

Arg Cys Gly Asp Ala Val Pro Arg Arg
        115                 120

<210> SEQ ID NO 7
<211> LENGTH: 122
<212> TYPE: PRT
<213> ORGANISM: Homo sapiens

<400> SEQUENCE: 7

Gly Ala Asp Asp Asp Asp Lys Ser Ser Glu Val Glu Val Pro Phe
1               5                   10                  15

Gln Glu Val Trp Gly Arg Ser Tyr Cys Arg Ala Leu Glu Arg Leu Val
            20                  25                  30

Asp Val Val Ser Glu Tyr Pro Ser Glu Val Glu His Met Phe Ser Pro
        35                  40                  45

Ser Cys Val Ser Leu Leu Arg Cys Thr Gly Cys Cys Gly Asp Glu Asn
    50                  55                  60

Leu His Cys Val Pro Val Glu Thr Ala Asn Val Thr Met Gln Leu Leu
65                  70                  75                  80

Lys Ile Arg Ser Gly Asp Arg Pro Ser Tyr Val Glu Leu Thr Phe Ser
                85                  90                  95

Gln His Val Arg Cys Glu Cys Arg Pro Leu Arg Glu Lys Met Lys Pro
            100                 105                 110

Glu Arg Cys Gly Asp Ala Val Pro Arg Arg
        115                 120

<210> SEQ ID NO 8
<211> LENGTH: 128
<212> TYPE: PRT
<213> ORGANISM: Homo sapiens

<400> SEQUENCE: 8

His His His His His His Gly Ala Asp Asp Asp Asp Lys Ser Ser Glu
1               5                   10                  15

Val Glu Val Val Pro Phe Gln Glu Val Trp Gly Arg Ser Tyr Cys Arg
            20                  25                  30

Ala Leu Glu Arg Leu Val Asp Val Val Ser Glu Tyr Pro Ser Glu Val
        35                  40                  45
```

```
Glu His Met Phe Ser Pro Ser Cys Val Ser Leu Leu Arg Cys Thr Gly
     50                  55                  60

Cys Cys Gly Asp Glu Asn Leu His Cys Val Pro Val Glu Thr Ala Asn
 65                  70                  75                  80

Val Thr Met Gln Leu Leu Lys Ile Arg Ser Gly Asp Arg Pro Ser Tyr
                 85                  90                  95

Val Glu Leu Thr Phe Ser Gln His Val Arg Cys Glu Cys Arg Pro Leu
                100                 105                 110

Arg Glu Lys Met Lys Pro Glu Arg Cys Gly Asp Ala Val Pro Arg Arg
            115                 120                 125
```

<210> SEQ ID NO 9
<211> LENGTH: 393
<212> TYPE: DNA
<213> ORGANISM: Homo sapiens

<400> SEQUENCE: 9

| ctgcctgctg | tgccccccca | gcagtgggcc | ttgtctgctg | ggaacggctc | gtcagaggtg | 60 |
| gaagtggtac | ccttccagga | agtgtggggc | cgcagctact | gccgggcgct | ggagaggctg | 120 |
| gtggacgtcg | tgtccgagta | ccccagcgag | gtggagcaca | tgttcagccc | atcctgtgtc | 180 |
| tccctgctgc | gctgcaccgg | ctgctgcggc | gatgagaatc | tgcactgtgt | gccggtggag | 240 |
| acggccaatg | tcaccatgca | gctcctaaag | atccgttctg | ggaccggcc | ctcctacgtg | 300 |
| gagctgacgt | tctctcagca | cgttcgctgc | gaatgccggc | ctctgcggga | agatgaag | 360 |
| ccggaaaggt | gcggcgatgc | tgttccccgg | agg | | | 393 |

<210> SEQ ID NO 10
<211> LENGTH: 411
<212> TYPE: DNA
<213> ORGANISM: Homo sapiens

<400> SEQUENCE: 10

| catcatcacc | atcaccatct | gcctgctgtg | ccccccagc | agtgggcctt | gtctgctggg | 60 |
| aacggctcgt | cagaggtgga | agtggtaccc | ttccaggaag | tgtggggccg | cagctactgc | 120 |
| cgggcgctgg | agaggctggt | ggacgtcgtg | tccgagtacc | ccagcgaggt | ggagcacatg | 180 |
| ttcagcccat | cctgtgtctc | cctgctgcgc | tgcaccggct | gctgcggcga | tgagaatctg | 240 |
| cactgtgtgc | cggtggagac | ggccaatgtc | accatgcagc | tcctaaagat | ccgttctggg | 300 |
| gaccggccct | cctacgtgga | gctgacgttc | tctcagcacg | ttcgctgcga | atgccggcct | 360 |
| ctgcgggaga | agatgaagcc | ggaaaggtgc | ggcgatgctg | ttccccggag | g | 411 |

<210> SEQ ID NO 11
<211> LENGTH: 408
<212> TYPE: DNA
<213> ORGANISM: Homo sapiens

<400> SEQUENCE: 11

| gatgacgacg | acaagctgcc | tgctgtgccc | ccccagcagt | gggccttgtc | tgctgggaac | 60 |
| ggctcgtcag | aggtggaagt | ggtacccttc | caggaagtgt | ggggccgcag | ctactgccgg | 120 |
| gcgctggaga | ggctggtgga | cgtcgtgtcc | gagtacccca | gcgaggtgga | gcacatgttc | 180 |
| agcccatcct | gtgtctccct | gctgcgctgc | accggctgct | gcggcgatga | gaatctgcac | 240 |
| tgtgtgccgg | tggagacggc | caatgtcacc | atgcagctcc | taaagatccg | ttctggggac | 300 |
| cggcctcct | acgtggagct | gacgttctct | cagcacgttc | gctgcgaatg | ccggcctctg | 360 |
| cgggagaaga | tgaagccgga | aaggtgcggc | gatgctgttc | cccggagg | | 408 |

<210> SEQ ID NO 12
<211> LENGTH: 432
<212> TYPE: DNA
<213> ORGANISM: Homo sapiens

<400> SEQUENCE: 12

```
catcatcacc atcaccatgg tgcagatgac gacgacaagc tgcctgctgt gccccccag      60 cagtgggcct tgtctgctgg gaacggctcg tcagaggtgg aagtggtacc cttccaggaa    120
gtgtggggcc gcagctactg ccgggcgctg gagaggctgg tggacgtcgt gtccgagtac    180
cccagcgagg tggagcacat gttcagccca tcctgtgtct ccctgctgcg ctgcaccggc    240
tgctgcggcg atgagaatct gcactgtgtg ccggtggaga cggccaatgt caccatgcag    300
ctcctaaaga tccgttctgg ggaccggccc tcctacgtgg agctgacgtt ctctcagcac    360
gttcgctgcg aatgccggcc tctgcgggag aagatgaagc cggaaaggtg cggcgatgct    420
gttccccgga gg                                                        432
```

<210> SEQ ID NO 13
<211> LENGTH: 345
<212> TYPE: DNA
<213> ORGANISM: Homo sapiens

<400> SEQUENCE: 13

```
tcgtcagagg tggaagtggt acccttccag gaagtgtggg gccgcagcta ctgccgggcg     60
ctggagaggc tggtggacgt cgtgtccgag taccccagcg aggtggagca catgttcagc    120
ccatcctgtg tctccctgct gcgctgcacc ggctgctgcg gcgatgagaa tctgcactgt    180
gtgccggtgg agacggccaa tgtcaccatg cagctcctaa agatccgttc tggggaccgg    240
ccctcctacg tggagctgac gttctctcag cacgttcgct gcgaatgccg gcctctgcgg    300
gagaagatga agccggaaag gtgcggcgat gctgttcccc ggagg                    345
```

<210> SEQ ID NO 14
<211> LENGTH: 363
<212> TYPE: DNA
<213> ORGANISM: Homo sapiens

<400> SEQUENCE: 14

```
catcatcacc atcaccattc gtcagaggtg gaagtggtac ccttccagga agtgtgggc      60 cgcagctact gccgggcgct ggagaggctg gtggacgtcg tgtccgagta ccccagcgag    120
gtggagcaca tgttcagccc atcctgtgtc tccctgctgc gctgcaccgg ctgctgcggc    180
gatgagaatc tgcactgtgt gccggtggag acggccaatg tcaccatgca gctcctaaag    240
atccgttctg ggaccggcc ctcctacgtg gagctgacgt tctctcagca cgttcgctgc    300
gaatgccggc tctgcggga aagatgaag ccggaaggt gcggcgatgc tgttccccgg      360
agg                                                                  363
```

<210> SEQ ID NO 15
<211> LENGTH: 360
<212> TYPE: DNA
<213> ORGANISM: Homo sapiens

<400> SEQUENCE: 15

```
gatgacgacg acaagtcgtc agaggtggaa gtggtaccct tccaggaagt gtggggccgc     60
agctactgcc gggcgctgga gaggctggtg gacgtcgtgt ccgagtaccc cagcgaggtg    120
gagcacatgt tcagcccatc ctgtgtctcc ctgctgcgct gcaccggctg ctgcggcgat    180
```

```
gagaatctgc actgtgtgcc ggtggagacg gccaatgtca ccatgcagct cctaaagatc      240
cgttctgggg accggccctc ctacgtggag ctgacgttct ctcagcacgt tcgctgcgaa      300
tgccggcctc tgcgggagaa gatgaagccg gaaaggtgcg gcgatgctgt tccccggagg      360
```

<210> SEQ ID NO 16
<211> LENGTH: 384
<212> TYPE: DNA
<213> ORGANISM: Homo sapiens

<400> SEQUENCE: 16

```
catcatcacc atcaccatgg tgcagatgac gacgacaagt cgtcagaggt ggaagtggta       60
cccttccagg aagtgtgggg ccgcagctac tgccgggcgc tggagaggct ggtggacgtc      120
gtgtccgagt accccagcga ggtggagcac atgttcagcc atcctgtgt ctccctgctg       180 cgctgcaccg gctgctgcgg cgatgagaat ctgcactgtg tgccggtgga cggccaat       240 gtcaccatgc agctcctaaa gatccgttct ggggaccggc cctcctacgt ggagctgacg      300
ttctctcagc acgttcgctg cgaatgccgg cctctgcggg agaagatgaa gccggaaagg      360
tgcggcgatg ctgttccccg gagg                                            384
```

<210> SEQ ID NO 17
<211> LENGTH: 6
<212> TYPE: PRT
<213> ORGANISM: Artificial sequence
<220> FEATURE:
<223> OTHER INFORMATION: Chemically synthesized - His Tag

<400> SEQUENCE: 17

```
His His His His His His
1               5
```

<210> SEQ ID NO 18
<211> LENGTH: 5
<212> TYPE: PRT
<213> ORGANISM: Artificial sequence
<220> FEATURE:
<223> OTHER INFORMATION: Chemically synthesized - enterokinase cleavage
      site

<400> SEQUENCE: 18

```
Asp Asp Asp Asp Lys
1               5
```

<210> SEQ ID NO 19
<211> LENGTH: 15
<212> TYPE: PRT
<213> ORGANISM: Artificial Sequence
<220> FEATURE:
<223> OTHER INFORMATION: Chemically synthesized - Linking Sequence

<400> SEQUENCE: 19

```
Gly Pro Ala Lys Glu Leu Thr Pro Leu Lys Glu Ala Lys Val Ser
1               5                  10                  15
```

<210> SEQ ID NO 20
<211> LENGTH: 57
<212> TYPE: DNA
<213> ORGANISM: Artificial sequence
<220> FEATURE:
<223> OTHER INFORMATION: Chemically synthesized

<400> SEQUENCE: 20

```
ccggctcgcg atgccatcat caccatcacc atctgcctgc tgtgcccccc cagcagt         57
```

<210> SEQ ID NO 21
<211> LENGTH: 33
<212> TYPE: DNA
<213> ORGANISM: Artificial sequence
<220> FEATURE:
<223> OTHER INFORMATION: Chemically synthesized

<400> SEQUENCE: 21
ccccgcggcc gctcacctcc ggggaacagc atc        33

<210> SEQ ID NO 22
<211> LENGTH: 477
<212> TYPE: DNA
<213> ORGANISM: Homo sapiens

<400> SEQUENCE: 22
atggacatgc gcgtgcccgc ccagctgctg ggcctgctgc tgctgtggtt ccccggctcg        60
cgatgccatc atcaccatca ccatctgcct gctgtgcccc ccagcagtg ggccttgtct       120
gctgggaacg gctcgtcaga ggtggaagtg gtacccttcc aggaagtgtg gggccgcagc       180
tactgccggg cgctggagag gctggtggac gtcgtgtccg agtaccccag cgaggtggag       240
cacatgttca gcccatcctg tgtctccctg ctgcgctgca ccggctgctg cggcgatgag       300
aatctgcact gtgtgccggt ggagacggcc aatgtcacca tgcagctcct aaagatccgt       360
tctggggacc ggccctccta cgtggagctg acgttctctc agcacgttcg ctgcgaatgc       420
cggcctctgc gggagaagat gaagccggaa aggtgcggcg atgctgttcc ccggagg        477

<210> SEQ ID NO 23
<211> LENGTH: 429
<212> TYPE: DNA
<213> ORGANISM: Homo sapiens

<400> SEQUENCE: 23
atggacatgc gcgtgcccgc ccagctgctg ggcctgctgc tgctgtggtt ccccggctcg        60
cgatgccatc atcaccatca ccattcgtca gaggtggaag tggtacccct tccaggaagtg      120
tggggccgca gctactgccg ggcgctggag aggctggtgg acgtcgtgtc cgagtacccc       180
agcgaggtgg agcacatgtt cagcccatcc tgtgtctccc tgctgcgctg caccggctgc       240
tgcggcgatg agaatctgca ctgtgtgccg gtggagacgg ccaatgtcac catgcagctc       300
ctaaagatcc gttctgggga ccggccctcc tacgtggagc tgacgttctc tcagcacgtt       360
cgctgcgaat gccggcctct gcgggagaag atgaagccgg aaaggtgcgg cgatgctgtt       420
ccccggagg                                                               429

<210> SEQ ID NO 24
<211> LENGTH: 62
<212> TYPE: DNA
<213> ORGANISM: Artificial sequence
<220> FEATURE:
<223> OTHER INFORMATION: Chemically synthesized

<400> SEQUENCE: 24
ccggctcgcg atgccatcat caccatcacc attcgtcaga ggtggaagtg gtacccttcc        60
ag                                                                       62

<210> SEQ ID NO 25
<211> LENGTH: 72
<212> TYPE: DNA
<213> ORGANISM: Artificial sequence

```
<220> FEATURE:
<223> OTHER INFORMATION: Chemically synthesized

<400> SEQUENCE: 25
ggctcgcgat gccatcatca ccatcaccat ggtgcagatg acgacgacaa gctgcctgct      60
gtgccccccc ag                                                          72

<210> SEQ ID NO 26
<211> LENGTH: 498
<212> TYPE: DNA
<213> ORGANISM: Homo sapiens

<400> SEQUENCE: 26
atggacatgc gcgtgcccgc ccagctgctg ggcctgctgc tgctgtggtt ccccggctcg      60
cgatgccatc atcaccatca ccatggtgac gatgacgacg acaagctgcc tgctgtgccc     120
ccccagcagt gggccttgtc tgctgggaac ggctcgtcag aggtggaagt ggtacccttc     180
caggaagtgt ggggccgcag ctactgccgg gcgctggaga ggctggtgga cgtcgtgtcc     240
gagtacccca gcgaggtgga gcacatgttc agcccatcct gtgtctccct gctgcgctgc     300
accggctgct gcgcgatgaa gaatctgcac tgtgtgccgg tggagacggc caatgtcacc     360
atgcagctcc taaagatccg ttctggggac cggcctcct acgtggagct gacgttctct      420
cagcacgttc gctgcgaatg ccggcctctg cgggagaaga tgaagccgga aggtgcggc      480 gatgctgttc cccggagg                                                   498

<210> SEQ ID NO 27
<211> LENGTH: 339
<212> TYPE: DNA
<213> ORGANISM: Murine

<400> SEQUENCE: 27
gatgttgtga tgacccaaac tccactctcc ctacctgtca gtcctggaga tcaagcctcc     60
atctcttgca gatctagtca gagccttgta cacagtaatg gacacaccta tttacattgg    120
tacctgcaga agccaggcca gtctccaaag ctcctgatct acaaagtttc caaccgattt    180
tctggggtcc ccgacagggt cagtggcagt ggatcaggga cagatttcac actcaagatc    240
agcagagtgg aggctgagga tctgggagtt tatttctgct ctcaaagtac acatgttcct    300
ccgacgttcg gtggaggcac caagctggaa atcaaacgg                           339

<210> SEQ ID NO 28
<211> LENGTH: 339
<212> TYPE: DNA
<213> ORGANISM: Murine

<400> SEQUENCE: 28
ctacaacact actgggtttg aggtgagagg gatggacagt caggacctct agttcggagg     60
tagagaacgt ctagatcagt ctcggaacat gtgtcattac ctgtgtggat aaatgtaacc    120
atggacgtct tcggtccggt cagaggtttc gaggactaga tgtttcaaag gttggctaaa    180
agaccccagg ggctgtccca gtcaccgtca cctagtccct gtctaaagtg tgagttctag    240
tcgtctcacc tccgactcct agaccctcaa ataaagacga gagtttcatg tgtacaagga    300
ggctgcaagc cacctccgtg gttcgacctt tagtttgcc                           339

<210> SEQ ID NO 29
<211> LENGTH: 113
<212> TYPE: PRT
<213> ORGANISM: Murine
```

<400> SEQUENCE: 29

Asp Val Val Met Thr Gln Thr Pro Leu Ser Leu Pro Val Ser Pro Gly
1               5                   10                  15

Asp Gln Ala Ser Ile Ser Cys Arg Ser Ser Gln Ser Leu Val His Ser
            20                  25                  30

Asn Gly His Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

Arg

<210> SEQ ID NO 30
<211> LENGTH: 366
<212> TYPE: DNA
<213> ORGANISM: Murine

<400> SEQUENCE: 30
caggttcacc tgcagcagtc tggagctgag ctgatgaagc ctggggcctc agtgaagata      60
tcctgcaagg ctactggcta cacattcagt agctactgga tagagtgggt aaagcagagg     120
cctggacatg gccttgagtg gattggagag attttacctg gaagtgtaag taataatttc     180
aatgagaagt tcaaggacaa ggccacactc actgcagatc cttcctccaa cacagcctac     240
atacaagtca gcagcctgac atctgaggac tctgccgtct attactgtgc aagatcaacg     300 ggctttact acgggggtaa ctactttgac cactggggcc aaggcaccac tctcgcagtc     360
tcctca                                                                366

<210> SEQ ID NO 31
<211> LENGTH: 366
<212> TYPE: DNA
<213> ORGANISM: Murine

<400> SEQUENCE: 31
gtccaagtgg acgtcgtcag acctcgactc gactacttcg gaccccggag tcacttctat      60
aggacgttcc gatgaccgat gtgtaagtca tcgatgacct atctcaccca tttcgtctcc     120
ggacctgtac cggaactcac ctaacctctc taaaatggac cttcacattc attattaaag     180
ttactcttca agttcctgtt ccggtgtgag tgacgtctag aaggaggtt gtgtcggatg      240 tatgttcagt cgtcggactg tagactcctg agacggcaga taatgacacg ttctagttgc     300
ccgaaaatga tgcccccatt gatgaaactg gtgaccccgg ttccgtggtg agagcgtcag     360
aggagt                                                                366

<210> SEQ ID NO 32
<211> LENGTH: 122
<212> TYPE: PRT
<213> ORGANISM: Murine

<400> SEQUENCE: 32

Gln Val His Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Val Ser Asn Asn Phe Asn Glu Lys Phe
    50                  55                  60

Lys Asp Lys Ala Thr Leu Thr Ala Asp Pro Ser Ser Asn Thr Ala Tyr
65                  70                  75                  80

Ile Gln Val Ser Ser Leu Thr Ser Glu Asp Ser Ala Val Tyr Tyr Cys
                85                  90                  95

Ala Arg Ser Thr Gly Phe Tyr Tyr Gly Asn Tyr Phe Asp His Trp
            100                 105                 110

Gly Gln Gly Thr Thr Leu Ala Val Ser Ser
        115                 120

<210> SEQ ID NO 33
<211> LENGTH: 348
<212> TYPE: DNA
<213> ORGANISM: Murine

<400> SEQUENCE: 33
caggtgcagc tgaagcagtc aggacctggc cttgtgcagc cctcacagag cctgtccatc      60
acctgcacag tctctggttt ctcattgact acgtatggta tacactgggt tcgccagtcc     120
ccaggaaagg gtctggagtg gctgggagtg atgtggagtg gtggagacac agactatgat     180
gcagctttca tatccagact gagcatcagc aaggacaatt ccaagagcca gttttctttt     240
aaaatgaaca gtctgcaagc taatgacaca ggcatatatt actgtgccag atataggttc     300
tatggtatgg actactgggg tcaaggaacc tcagtcaccg tctcctca                  348

<210> SEQ ID NO 34
<211> LENGTH: 348
<212> TYPE: DNA
<213> ORGANISM: Murine

<400> SEQUENCE: 34
gtccacgtcg acttcgtcag tcctggaccg gaacacgtcg ggagtgtctc ggacaggtag      60
tggacgtgtc agagaccaaa gagtaactga tgcataccat atgtgaccca gcggtcagg     120 ggtcctttcc agacctcac cgaccctcac tacacctcac cacctctgtg tctgatacta     180
cgtcgaaagt ataggtctga ctcgtagtcg ttcctgttaa ggttctcggt tcaaaagaaa     240
ttttacttgt cagacgttcg attactgtgt ccgtatataa tgacacggtc tatatccaag     300
ataccatacc tgatgacccc agttccttgg agtcagtggc agaggagt                  348

<210> SEQ ID NO 35
<211> LENGTH: 116
<212> TYPE: PRT
<213> ORGANISM: Murine

<400> SEQUENCE: 35

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Ile His Trp Val Arg Gln Ser Pro Gly Lys Gly Leu Glu Trp Leu
        35                  40                  45

Gly Val Met Trp Ser Gly Gly Asp Thr Asp Tyr Asp Ala Ala Phe Ile

```
                 50                  55                  60
Ser Arg Leu Ser Ile Ser Lys Asp Asn Ser Lys Ser Gln Val Phe Phe
 65                  70                  75                  80

Lys Met Asn Ser Leu Gln Ala Asn Asp Thr Gly Ile Tyr Tyr Cys Ala
                 85                  90                  95

Arg Tyr Arg Phe Tyr Gly Met Asp Tyr Trp Gly Gln Gly Thr Ser Val
                100                 105                 110

Thr Val Ser Ser
        115

<210> SEQ ID NO 36
<211> LENGTH: 131
<212> TYPE: PRT
<213> ORGANISM: Homo sapiens

<400> SEQUENCE: 36

Leu Pro Ala Val Pro Pro Gln Gln Trp Ala Leu Ser Ala Gly Asp Gly
 1               5                  10                  15

Ser Ser Glu Val Glu Val Val Pro Phe Gln Glu Val Trp Gly Arg Ser
                20                  25                  30

Tyr Cys Arg Ala Leu Glu Arg Leu Val Asp Val Val Ser Glu Tyr Pro
             35                  40                  45

Ser Glu Val Glu His Met Phe Ser Pro Ser Cys Val Ser Leu Leu Arg
 50                  55                  60

Cys Thr Gly Cys Cys Gly Asp Glu Asn Leu His Cys Val Pro Val Glu
 65                  70                  75                  80

Thr Ala Asn Val Thr Met Gln Leu Leu Lys Ile Arg Ser Gly Asp Arg
                 85                  90                  95

Pro Ser Tyr Val Glu Leu Thr Phe Ser Gln His Val Arg Cys Glu Cys
                100                 105                 110

Arg Pro Leu Arg Glu Lys Met Lys Pro Glu Arg Cys Gly Asp Ala Val
            115                 120                 125

Pro Arg Arg
    130

<210> SEQ ID NO 37
<211> LENGTH: 137
<212> TYPE: PRT
<213> ORGANISM: Homo sapiens

<400> SEQUENCE: 37

His His His His His His Leu Pro Ala Val Pro Pro Gln Gln Trp Ala
 1               5                  10                  15

Leu Ser Ala Gly Asp Gly Ser Ser Glu Val Glu Val Val Pro Phe Gln
                20                  25                  30

Glu Val Trp Gly Arg Ser Tyr Cys Arg Ala Leu Glu Arg Leu Val Asp
             35                  40                  45

Val Val Ser Glu Tyr Pro Ser Glu Val Glu His Met Phe Ser Pro Ser
 50                  55                  60

Cys Val Ser Leu Leu Arg Cys Thr Gly Cys Cys Gly Asp Glu Asn Leu
 65                  70                  75                  80

His Cys Val Pro Val Glu Thr Ala Asn Val Thr Met Gln Leu Leu Lys
                 85                  90                  95

Ile Arg Ser Gly Asp Arg Pro Ser Tyr Val Glu Leu Thr Phe Ser Gln
                100                 105                 110

His Val Arg Cys Glu Cys Arg Pro Leu Arg Glu Lys Met Lys Pro Glu
            115                 120                 125
```

```
Arg Cys Gly Asp Ala Val Pro Arg Arg
    130                 135

<210> SEQ ID NO 38
<211> LENGTH: 131
<212> TYPE: PRT
<213> ORGANISM: Homo sapiens

<400> SEQUENCE: 38

Leu Pro Ala Val Pro Gln Gln Trp Ala Leu Ser Ala Gly Asp Gly
1               5                   10                  15

Ser Ser Glu Val Glu Val Pro Phe Gln Gln Val Trp Gly Arg Ser
                20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
        50                  55                  60

Cys Thr Gly Cys Cys Gly Asp Glu Asn Leu His Cys Val Pro Val Glu
65                  70                  75                  80

Thr Ala Asp Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 39
<211> LENGTH: 137
<212> TYPE: PRT
<213> ORGANISM: Homo sapiens

<400> SEQUENCE: 39

His His His His His His Leu Pro Ala Val Pro Pro Gln Gln Trp Ala
1               5                   10                  15

Leu Ser Ala Gly Asp Gly Ser Ser Glu Val Glu Val Val Pro Phe Gln
                20                  25                  30

Glu Val Trp Gly Arg Ser Tyr Cys Arg Ala Leu Glu Arg Leu Val Asp
            35                  40                  45

Val Val Ser Glu Tyr Pro Ser Glu Val Glu His Met Phe Ser Pro Ser
        50                  55                  60

Cys Val Ser Leu Leu Arg Cys Thr Gly Cys Cys Gly Asp Glu Asn Leu
65                  70                  75                  80

His Cys Val Pro Val Glu Thr Ala Asp Val Thr Met Gln Leu Leu Lys
                85                  90                  95

Ile Arg Ser Gly Asp Arg Pro Ser Tyr Val Glu Leu Thr Phe Ser Gln
            100                 105                 110

His Val Arg Cys Glu Cys Arg Pro Leu Arg Glu Lys Met Lys Pro Glu
        115                 120                 125

Arg Cys Gly Asp Ala Val Pro Arg Arg
    130                 135

<210> SEQ ID NO 40
<211> LENGTH: 137
<212> TYPE: PRT
<213> ORGANISM: Homo sapiens
<220> FEATURE:
```

<221> NAME/KEY: MISC_FEATURE
<223> OTHER INFORMATION: Where Xaa can be N or D
<220> FEATURE:
<221> NAME/KEY: misc_feature
<222> LOCATION: (89)..(89)
<223> OTHER INFORMATION: Xaa can be any naturally occurring amino acid

<400> SEQUENCE: 40

```
His His His His His Leu Pro Ala Val Pro Pro Gln Gln Trp Ala
 1               5                  10                  15

Leu Ser Ala Gly Asp Gly Ser Ser Glu Val Glu Val Pro Phe Gln
             20                  25                  30

Glu Val Trp Gly Arg Ser Tyr Cys Arg Ala Leu Glu Arg Leu Val Asp
             35                  40                  45

Val Val Ser Glu Tyr Pro Ser Glu Val Glu His Met Phe Ser Pro Ser
 50                  55                  60

Cys Val Ser Leu Leu Arg Cys Thr Gly Cys Cys Gly Asp Glu Asn Leu
 65                  70                  75                  80

His Cys Val Pro Val Glu Thr Ala Xaa Val Thr Met Gln Leu Leu Lys
                 85                  90                  95

Ile Arg Ser Gly Asp Arg Pro Ser Tyr Val Glu Leu Thr Phe Ser Gln
                100                 105                 110

His Val Arg Cys Glu Cys Arg Pro Leu Arg Glu Lys Met Lys Pro Glu
            115                 120                 125

Arg Cys Gly Asp Ala Val Pro Arg Arg
            130                 135
```

<210> SEQ ID NO 41
<211> LENGTH: 324
<212> TYPE: DNA
<213> ORGANISM: Murine

<400> SEQUENCE: 41

```
gccatccaga tgactcagtc ttcatcctcc ttttctgtat ctctgggaga cagagtcacc    60
attacttgca aggcaagtga ggacatatat aatcggttcg cctggtatca gcagaaaccc   120
ggaaatgctc ctaggctctt aatatctggt gcagccagtt tggaagctgg ggttccttca   180
agattcagtg gcagtggatc tggacaggat tacactctca gcattaccag tcttcagact   240
gaagatgttg ctacttatta ctgtcaacag tattggagta ctccgtggac gttcggtgga   300
ggcaccaagc tggaaatcaa acgg                                          324
```

<210> SEQ ID NO 42
<211> LENGTH: 324
<212> TYPE: DNA
<213> ORGANISM: Murine

<400> SEQUENCE: 42

```
cggtaggtct actgagtcag aagtaggagg aaaagacata gagaccctct gtctcagtgg    60
taatgaacgt tccgttcact cctgtatata ttagccaagc ggaccatagt cgtctttggg   120
cctttacgag gatccgagaa ttatagacca cgtcggtcaa accttcgacc ccaaggaagt   180
tctaagtcac cgtcacctag acctgtccta atgtgagagt cgtaatggtc agaagtctga   240
cttctacaac gatgaataat gacagttgtc ataacctcat gaggcacctg caagccacct   300
ccgtggttcg acctttagtt tgcc                                          324
```

<210> SEQ ID NO 43
<211> LENGTH: 108
<212> TYPE: PRT

-continued

```
<213> ORGANISM: Murine

<400> SEQUENCE: 43

Ala Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Phe Ala Trp Tyr Gln Gln Lys Pro Gly Asn Ala Pro Arg Leu Leu Ile
        35                  40                  45

Ser Gly Ala Ala Ser Leu Glu Ala Gly Val Pro Ser Arg Phe Ser Gly
    50                  55                  60

Ser Gly Ser Gly Gln Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Trp
                85                  90                  95

Thr Phe Gly Gly Gly Thr Lys Leu Glu Ile Lys Arg
            100                 105
```

PLGF-1 ASSAY AND KITS AND COMPONENTS THEREOF

RELATED APPLICATION INFORMATION

This application claims priority to U.S. Ser. No. 61/073,624 filed on Jun. 18, 2008 and U.S. Ser. No. 61/089,172 filed on Aug. 15, 2008, the contents of each of which are herein incorporated by reference.

TECHNICAL FIELD

The present disclosure relates, among other things, to human PlGF-1 (i.e., both glycosylated and deglycosylated human PlGF-1), and methods of using the human PlGF-1. The present disclosure also relates to antibodies that bind to human PlGF-1, and methods of using these antibodies. Finally, the present disclosure further relates to human PlGF-1 immunoassays and kits, and to methods of using human PlGF-1 and antibodies that bind to human PlGF-1 in immunoassays and kits.

BACKGROUND

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis, which takes place in healthy individuals, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

Because of the crucial role of angiogenesis in so many physiological and pathological processes, factors involved in the control of angiogenesis have been intensively investigated. A number of growth factors have been shown to be involved in the regulation of angiogenesis. These growth factors include fibroblast growth factors (FGFs), vascular endothelial growth factors (VEGF), platelet-derived growth factor (PDGF), transforming growth factor α (TGFα), and hepatocyte growth factor (HGF) (See, Folkman et al., *J. Biol. Chem.*, 267: 10931-10934 (1992)).

The PDGF and VEGF family of growth factors are similar in that both naturally exist as dimeric forms in order to interact with their specific receptors. Additionally, these families of growth factors and their corresponding receptors are believed to be primarily responsible for stimulation of endothelial cell growth and differentiation, and for certain functions of differentiated cells. It is believed that these factors act via receptor tyrosine kinases (RTKs).

A number of PDGF/VEGF family members have been identified. These include PDGF-A (See, for example, GenBank Accession No. X06374), PDGF-B (See, for example, GenBank Accession No. M12783), PDGF-C (see, e.g., PCT International Application WO 00/18212), PDGF-D (see, e.g., PCT International Application WO 00/027879), VEGF (also known as VEGF-A, or by particular isoform), Placenta growth factor, PlGF (see, e.g., U.S. Pat. No. 5,919,899), VEGF-B (also known as VEGF-related factor (VRF); see, e.g., PCT International Application WO 96/26736 and WO 96/26736), VEGF-C, (see, e.g., U.S. Pat. No. 6,221,839 and WO 98/33917), VEGF-D (also known as c-fos-induced growth factor (FIGF); see, e.g., U.S. Pat. No. 6,235,713 and PCT International Application WO 98/07832), VEGF-E (also known as NZ7 VEGF or OV NZ7; see, e.g., PCT International Application WO 00/025805 and U.S. Patent Publication No. 2003/0113870), NZ2 VEGF (also known as OV NZ2; see, GenBank Accession No. S67520), D1701 VEGF-like protein (see, e.g., GenBank Accession No. AF106020; Meyer et al., *EMBO J.* 18:363-374), and NZ10 VEGF-like protein (see, e.g., PCT International Application WO 00/25805; Stacker and Achen, *Growth Factors,* 17:1-11 (1999); Neufeld et al., *FASEB J.,* 13:9-22 (1999); Ferrara, *J Mol Med* 77:527-543 (1999)).

Type 1 Placental Growth Factor (PlGF-1) is an angiogenic homodimeric glycoprotein. When in dimeric form, PlGF-1 exhibits angiogenic activity. In monomeric form, PlGF-1 is inactive. The complete polynucleotide sequence encoding the PlGF-1 protein, along with its polypeptide sequence, is described in European Patent Publication No. 0 550 519 and PCT International Application WO 92/06194. PlGF-1 binds as a homodimer to its receptor, the fms-like tyrosine kinase Flt-1 receptor. A soluble form of the Flt-1 receptor (sFlt-1) has been identified. sFlt-1 is a splice variant of the Flt-1 receptor which lacks the transmembrane and cytoplasmic domains of the Flt-1 receptor, but contains seven IgG-like domains of the external portion of the receptor. PlGF-1 also binds to the sFlt-1 receptor. Because PlGF-1 plays such an important role in pathological angiogenesis, it has the potential to become a prognostic marker for use in identifying or predicting risk of certain diseases (e.g., cardiovascular disease and hypertensive disorders including hypertension during pregnancy). Additionally, there is no reported biological role for the circulating complex of the PlGF-1 and sFlt-1 proteins bound to each other, therefore the detection of the free (uncomplexed), forms of these proteins could provide potentially more useful clinical information (e.g., published U.S. Patent Application No. 2007-0111326).

Thereupon, there is a need in the art for methods and kits and components thereof that can be employed for monitoring for PlGF-1. Moreover, there is also a need in the art for methods and kits and components thereof that can be employed for monitoring for free PlGF-1. These and other objects of the disclosure will be apparent from the description following herein.

SUMMARY

In one embodiment the present disclosure relates to an isolated antibody that specifically binds to human PlGF-1 or human PlGF-1 fragment, wherein the antibody:

(a) has a variable heavy domain region comprising the amino acid sequence of SEQ ID NO:32; (b) has a variable light domain region comprising the amino acid sequence of SEQ ID NO: 29; or (c) has a variable heavy domain region comprising the amino acid sequence of SEQ ID NO:32 and a variable light domain region comprising the amino acid sequence of SEQ ID NO:29. Such an antibody includes that produced by murine hybridoma cell line 1-255-713 having ATCC Accession No. PTA-8536, and the disclosure further provides a murine hybridoma cell line 1-255-713 having ATCC Accession No. PTA-8536.

In another embodiment the disclosure provides an isolated antibody that specifically binds to human PlGF-1 or human PlGF-1 fragment, wherein the antibody:

(a) has a variable heavy domain region comprising the amino acid sequence of SEQ ID NO:35; (b) has a variable light domain region comprising the amino acid sequence of SEQ ID NO:43; or (c) has a variable heavy domain region comprising the amino acid sequence of SEQ ID NO:35 and a variable light domain region comprising the amino acid sequence of SEQ ID NO:43. Such an antibody includes that produced by murine hybridoma cell line 2-826-335 having ATCC Accession No. PTA-8539 (as well as fragments thereof that can be employed as conjugate, e.g., a Fab'2 fragment), and the disclosure further provides a murine hybridoma cell line 2-826-335 having ATCC Accession No. PTA-8539.

The disclosure further conveys a method for determining the amount of human PlGF-1 or human PlGF-1 fragment in a test sample, the method comprising the steps of:

(a) contacting a test sample suspected of containing human PlGF-1 or human PlGF-1 fragment with at least one first capture antibody so as to form a first capture antibody/human PlGF-1 or human PlGF-1 fragment complex, wherein the at least one capture first antibody binds to human PlGF-1 or human PlGF-1 fragment;

(b) contacting the antibody/human PlGF-1 or human PlGF-1 fragment complex with at least one second detection antibody that binds to human PlGF-1 or human PlGF-1 fragment and that has been conjugated to a detectable label to form a second detection antibody/human PlGF-1 or human PlGF-1 fragment/first capture antibody complex, wherein the at least one second detection antibody differs from the first capture antibody; and (c) determining the amount of human PlGF-1 or human PlGF-1 fragment contained in the test sample based on the amount of the second detection antibody/human PlGF-1 or human PlGF-1 fragment/first antibody capture complex formed in step (b), wherein the at least one first capture antibody or the at least one detection antibody is an antibody selected from the group consisting of an antibody produced by murine hybridoma cell line 1-255-713 having ATCC Accession No. PTA-8536, an antibody produced by murine hybridoma cell line 2-826-335 having ATCC Accession No. PTA-8539, and combinations thereof.

In one aspect of this method, the at least one first capture antibody is immobilized on a solid phase either prior to or following contacting with the test sample. Alternately, the at least one first capture antibody is immobilized on a solid phase prior to formation of the second detection antibody/human PlGF-1 or human PlGF-1 fragment/first capture antibody complex. Optionally, the at least one first capture antibody is immobilized on a solid phase prior to formation of the first capture antibody/human PlGF-1 or human PlGF-1 fragment complex. Further optionally, the at least one first antibody is immobilized on a solid phase after formation of the first capture antibody/human PlGF-1 or human PlGF-1 fragment complex.

In such a method, optionally the detectable label is selected from the group consisting of a radioactive label, an enzymatic label, a chemiluminescent label, a fluorescence label, a thermometric label, and an immuno-polymerase chain reaction label. In one aspect, the detectable label is acridinium.

The method can be carried out in the assessment of a variety of diseases, disorders and conditions. In one aspect, the method is carried out to evaluate whether or not a subject is suffering from cardiovascular disease, sickle cell disease, chronic obstructive pulmonary disease, age-related macular degeneration, peripheral vascular occlusive disease, inflammation, preeclampsia, psoriasis, Crohn's disease, endometriosis or rheumatoid arthritis. In another aspect, the method is carried out to evaluate whether or not a subject is suffering from preeclampsia or cardiovascular disease.

In one embodiment, the method is adapted for use in an automated system or semi-automated system. Optimally the automated or semi-automated system is from about 1.5 to about 2 times better at detecting free PlGF-1 than is the non-automated ELISA, especially within a range of sFlt-1:PlGF molar ratios of from about 2.5 to about 50 (e.g., about 2.5, about 5, about 10, about 20, about 30, about 40, or about 50).

In the methods as described herein, optionally the amount of human PlGF-1 or human PlGF-1 fragment assessed is free human PlGF-1 or free human PlGF-1 fragment. The disclosure thus provides a method for determining the amount of free human PlGF-1 or free human PlGF-1 fragment in a test sample. In one embodiment, this method comprising the steps of:

(a) contacting a test sample suspected of containing free human PlGF-1 or free human PlGF-1 fragment with at least one first capture antibody so as to form a first capture antibody/human PlGF-1 or human PlGF-1 fragment complex, wherein the at least one capture first antibody binds to free human PlGF-1 or free human PlGF-1 fragment and further wherein the at least one capture antibody does not substantially bind to human PlGF-1 or human PlGF-1 fragment that is already bound to sFlt-1;

(b) contacting the antibody/human PlGF-1 or human PlGF-1 fragment complex with at least one second detection antibody that binds to human PlGF-1 or human PlGF-1 fragment and that has been conjugated to a detectable label to form a second detection antibody/human PlGF-1 or human PlGF-1 fragment/first capture antibody complex, wherein the at least one second detection antibody differs from the first capture antibody; and (c) determining the amount of free human PlGF-1 or free human PlGF-1 fragment contained in the test sample based on the amount of the second detection antibody/human PlGF-1 or human PlGF-1 fragment/first antibody capture complex formed in step (b).

In such a method, optionally the at least one first capture antibody is an antibody produced by murine hybridoma cell line 2-826-335 having ATCC Accession No. PTA-8539, and further, optionally the at least one second detection antibody is an antibody produced by murine hybridoma cell line 1-255-713 having ATCC Accession No. PTA-8536 and combinations thereof. Alternately, optionally the at least one first capture antibody is MAB264. The second detection antibody can be any appropriate antibody different than MAB264, such as polyclonal antibody pB264. Further optionally, the method is adapted for use in an automated system or semi-automated system. Optimally the automated or semi-automated system is from about 1.5 to about 2 times better at detecting free PlGF-1 than is the non-automated ELISA, especially within a range of sFlt-1:PlGF molar ratios of from about 2.5 to about 50 (e.g., about 2.5, about 5, about 10, about 20, about 30, about 40, or about 50).

Accordingly, the present disclosure provides among other things an immunodiagnostic reagent comprising one or more antibodies selected from the group consisting of:

(a) an isolated antibody that specifically binds to human PlGF-1 or human PlGF-1 fragment, wherein the antibody has a variable heavy domain region comprising the amino acid sequence of SEQ ID NO:32;

(b) an isolated antibody that specifically bind to human PlGF-1 or human PlGF-1 fragment, wherein the antibody has a variable light domain region comprising the amino acid sequence of SEQ ID NO:29;

(c) an isolated antibody that specifically binds to human PlGF-1 or human PlGF-1 fragment, wherein the antibody has a variable heavy domain region comprising the amino acid sequence of SEQ ID NO:32 and a variable light domain region comprising the amino acid sequence of SEQ ID NO:29;

(d) an antibody produced by murine hybridoma cell line 1-255-713 having ATCC Accession No. PTA-8536;

(e) an isolated antibody that specifically binds to human PlGF-1 or human PlGF-1 fragment, wherein the antibody has a variable heavy domain region comprising the amino acid sequence of SEQ ID NO:35;

(f) an isolated antibody that specifically bind to human PlGF-1 or human PlGF-1 fragment, wherein the antibody has a variable light domain region comprising the amino acid sequence of SEQ ID NO:43;

(g) an isolated antibody that specifically binds to human PlGF-1 or human PlGF-1 fragment, wherein the antibody has a variable heavy domain region comprising the amino acid sequence of SEQ ID NO:35 and a variable light domain region comprising the amino acid sequence of SEQ ID NO:43; and (h) an antibody produced by murine hybridoma cell line 2-826-335 having ATCC Accession No. PTA-8539.

The present disclosure further provides a mammalian cell line which produces glycosylated human PlGF-1 or a glycosylated human PlGF-1 fragment. The mammalian cell line can be any cell line, but optionally is a chinese hamster ovary cell line or human embryonic kidney cell line. The disclosure thus also provides a chinese hamster ovary cell line selected from the group consisting of ATCC Accession No. PTA-8538, ATCC Accession No. PTA-8540 and ATCC Accession No. PTA-8537.

In one aspect, the mammalian cell line (e.g., chinese hamster ovary cell line) produces glycosylated human PlGF-1 that is a full length human PlGF-1 having an amino acid sequence of 131 amino acids. Alternately, the mammalian cell line (e.g., chinese hamster ovary cell line) produces glycosylated human PlGF-1 that comprises an amino acid sequence selected from the group consisting of SEQ ID NO: 1, SEQ ID NO:2, SEQ ID NO:3 and SEQ ID NO:4. Furthermore, the mammalian cell line (e.g., chinese hamster ovary cell line) optionally produces glycosylated human PlGF-1 that is a human PlGF-1 fragment having an amino acid sequence of 115 amino acids. Alternately, the glycosylated human PlGF-1 fragment comprises an amino acid sequence selected from the group consisting of SEQ ID NO:5, SEQ ID NO:6, SEQ ID NO:7 and SEQ ID NO:8.

In another aspect, the glycosylated human PlGF-1 or the glycosylated human PlGF-1 fragment optionally further comprises at least one linking sequence. Among others, the at least one linking sequence is selected from the group consisting of a histidine tag, an enterokinase cleavage site or a combination of a histidine tag and an enterokinase cleavage site.

In yet another embodiment, provided by the disclosure is a method of producing glycosylated human PlGF-1 or glycosylated human PlGF-1 fragment thereof. Optionally, the method comprises the steps of:

(a) transfecting a cell line with a gene encoding human PlGF-1 under conditions such that glycosylated human PlGF-1 or glycosylated human PlGF-1 fragment is produced; and (b) recovering the glycosylated human PlGF-1 or glycosylated human PlGF-1 fragment produced by the cell line (e.g., a chinese hamster ovary cell line).

This method further optionally comprises in step (a) transfecting the cell line with an amplification gene, carrying out selection for amplified cells, and then carrying out step (b). In one aspect of this method, the amplification gene optionally encodes dihydrofolate reductase or glutamine synthase, and selection is done with methotrexate or glutamine. In another aspect, the glycosylated human PlGF-1 is a full-length human PlGF-1 having an amino acid sequence of 131 amino acids. Optionally the glycosylated human PlGF-1 further comprises at least one linking sequence, especially wherein the at least one linking sequence is selected from the group consisting of a histidine tag, an enterokinase cleavage site, and a combination of a histidine tag and an enterokinase cleavage site.

In other aspects of this method, the glycosylated human PlGF-1 comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, and any fragment thereof, or is a human PlGF-1 fragment having an amino acid sequence of 115 amino acids. Optionally the glycosylated human PlGF-1 fragment further comprises at least one linking sequence, especially wherein the at least one linking sequence is selected from the group consisting of a histidine tag, an enterokinase cleavage site, and a combination of a histidine tag and an enterokinase cleavage site.

The present disclosure thus accordingly further provides an isolated or purified glycosylated human PlGF-1 or glycosylated human PlGF-1 fragment, wherein the human PlGF-1 or human PlGF-1 fragment comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

Moreover, the disclosure provides an isolated or purified deglycosylated human PlGF-1 or deglycosylated human PlGF-1 fragment wherein at least one amino acid residue of a glycosylated human PlGF-1 or glycosylated human PlGF-1 fragment is converted to a different amino acid residue as a result of the deglycosylation. For example, at least one asparagine residue can be converted to an aspartic acid residue as a result of the deglycosylation.

Moreover, the present disclosure also provides isolated or purified deglycosylated human PlGF-1 or deglycosylated human PlGF-1 fragment, wherein said deglycosylated human PlGF-1 or deglycosylated human PlGF-1 fragment comprises a sequence selected from the group consisting of: SEQ ID NO:36, SEQ ID NO:37, SEQ ID NO:38, SEQ ID NO:39 and SEQ ID NO:40.

Additionally, the disclosure provides a calibrator or control for use in an assay for detecting human PlGF-1 in a test sample, the calibrator or control comprising glycosylated human PlGF-1 or glycosylated human PlGF-1 fragment, especially wherein the glycosylated human PlGF-1 or glycosylated human PlGF-1 fragment is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

Moreover, the disclosure provides a calibrator or control for use in an assay for detecting human PlGF-1 in a test sample, the calibrator or control comprising deglycosylated human PlGF-1, especially wherein the deglycosylated human PlGF-1 is selected from the group consisting of SEQ ID NO:1, SEQ ID NO:2, SEQ ID NO:3, SEQ ID NO:4, SEQ ID NO:36, SEQ ID NO:37, SEQ ID NO:38, SEQ ID NO:39 and SEQ ID NO:40.

Also provided by this disclosure is an isolated or purified glycosylated human PlGF-1 or glycosylated human PlGF-1 fragment wherein amino acid residue 89 of SEQ ID NO:2 is on average about 100% glycosylated, and residue 21 of SEQ ID NO:2 is on average is about 70% glycosylated, as compared to the wild-type sequence.

Still further provided by the disclosure is an isolated or purified glycosylated human PlGF-1 or glycosylated human PlGF-1 fragment wherein amino acid residue 83 of SEQ ID NO: 1 is on average about 100% glycosylated, and residue 15 of SEQ ID NO: 1 is on average about 70% glycosylated, as compared to the wild-type sequence.

The disclosure also provides an isolated or purified human PlGF-1 or human PlGF-1 fragment comprising a sequence selected of the group consisting of a polypeptide wherein:

(a) amino acid residue 21 of SEQ ID NO:2 is converted from asparagine to aspartic acid as compared to the wild-type sequence; and (b) amino acid residue 89 of SEQ ID NO:2 is converted from asparagine to aspartic acid as compared to the wild-type sequence.

Moreover, the disclosure still further provides an isolated or purified human PlGF-1 or human PlGF-1 fragment comprising a sequence selected of the group consisting of a polypeptide wherein:

(a) amino acid residue 15 of SEQ ID NO: 1 is converted from asparagine to aspartic acid as compared to the wild-type sequence; and (b) amino acid residue 83 of SEQ ID NO: 1 is converted from asparagine to aspartic acid as compared to the wild-type sequence.

The disclosure further provides an isolated or purified human PlGF-1 or human PlGF-1 fragment wherein one or more asparagine residues at position 21, position 89 or position 21 and 89 of SEQ ID NO:2 is glycosylated with at least one N-glycan having a structure selected from the group consisting of: (a) N-acetylneuraminic acid(Galactose)$_2$(Mannose)$_3$(N-acetyl-D-glucosamine)$_4$Fucose, (b) (N-acetylneuraminic acid)$_2$(Galactose)$_2$(Mannose)$_3$(N-acetyl-D-glucosamine)$_4$Fucose, (c) (N-acetylneuraminic acid)$_2$(Galactoseβ1-4N-acetyl-D-glucosamine)$_2$(Galactose)$_2$(Mannose)$_3$ (N-acetyl-D-glucosamine)$_4$Fucose or (Galactoseβ1-4N-acetyl-D-glucosamine) (Galactose)$_3$ (Mannose)$_3$ (N-acetyl-D-glucosamine)$_5$Fucose; (d) (N-acetylneuraminic acid)$_2$(Galactose)$_3$(Mannose)$_3$ (N-acetyl-D-glucosamine)$_5$Fucose; (e) (N-acetylneuraminic acid)$_3$(Galactose)$_3$(Mannose)$_3$(N-acetyl-D-glucosamine)$_5$ Fucose; (f) (N-acetylneuraminic acid)$_3$(Galactoseβ1-4N-acetyl-D-glucosamine) (Galactose)$_3$ (Mannose)$_3$ (N-acetyl-D-glucosamine)$_5$Fucose or (N-acetylneuraminic acid)$_3$ (Galactose)$_4$(Mannose)$_3$ (N-acetyl-D-glucosamine)$_6$Fucose; (g) (N-acetylneuraminic acid)$_4$(Galactose)$_4$(Mannose)$_3$(N-acetyl-D-glucosamine)$_6$Fucose; and (h) (N-acetylneuraminic acid)$_4$(Galactoseβ1-4N-acetyl-D-glucosamine) (Galactose)$_4$ (Mannose)$_3$ (N-acetyl-D-glucosamine)$_6$Fucose.

Still further, the disclosure provides an isolated or purified human PlGF-1 or human PlGF-1 fragment wherein one or more asparagine residues at position 15, position 83 or position 15 and 83 of SEQ ID NO: 1 is glycosylated with at least one N-glycan having a structure selected from the group consisting of: (a) N-acetylneuraminic acid(Galactose)$_2$(Mannose)$_3$(N-acetyl-D-glucosamine)$_4$Fucose, (b) (N-acetylneuraminic acid)$_2$(Galactose)$_2$(Mannose)$_3$(N-acetyl-D-glucosamine)$_4$Fucose, (c) (N-acetylneuraminic acid)$_2$ (Galactoseβ1-4N-acetyl-D-glucosamine)$_2$(Galactose)$_2$ (Mannose)$_3$ (N-acetyl-D-glucosamine)$_4$Fucose or (Galactoseβ1-4N-acetyl-D-glucosamine)(Galactose)$_3$(Mannose)$_3$(N-acetyl-D-glucosamine)$_5$Fucose; (d) (N-acetylneuraminic acid)$_2$(Galactose)$_3$(Mannose)$_3$(N-acetyl-D-glucosamine)$_5$Fucose; (e) (N-acetylneuraminic acid)$_3$ (Galactose)$_3$(Mannose)$_3$(N-acetyl-D-glucosamine)$_5$Fucose; (f) (N-acetylneuraminic acid)$_3$(Galactoseβ1-4N-acetyl-D-glucosamine) (Galactose)$_3$ (Mannose)$_3$ (N-acetyl-D-glucosamine)$_5$Fucose or (N-acetylneuraminic acid)$_3$ (Galactose)$_4$(Mannose)$_3$ (N-acetyl-D-glucosamine)$_6$Fucose; (g) (N-acetylneuraminic acid)$_4$(Galactose)$_4$(Mannose)$_3$(N-acetyl-D-glucosamine)$_6$Fucose; and (h) (N-acetylneuraminic acid)$_4$(Galactoseβ1-4N-acetyl-D-glucosamine) (Galactose)$_4$ (Mannose)$_3$ (N-acetyl-D-glucosamine)$_6$Fucose.

Further provided by the disclosure is an improvement of a method for detecting the presence of human PlGF-1 or human PlGF-1 fragment in a test sample. Such an improved method comprises:

(a) contacting a test sample suspected of containing human PlGF-1 or human PlGF-1 fragment with at least one antibody specific for the human PlGF-1 or human PlGF-1 fragment for a time and under conditions that allow the formation of a human PlGF-1 or human PlGF-1 fragment/antibody complex; and (b) detecting any mammalian human PlGF-1 or human PlGF-1 fragment/antibody complex formed as indicating the presence of the human PlGF-1 or human PlGF-1 fragment;

wherein the improvement comprises employing as a calibrator or control a calibrator or control comprising glycosylated or deglycosylated human PlGF-1 or glycosylated human PlGF-1 fragment selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

Still additionally, the disclosure relates to a diagnostic kit for the detection of human PlGF-1 or human PlGF-1 fragment, the kit comprising:

(a) at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539; and (b) instructions for using the kit.

In one aspect, the kit further comprises a calibrator or control comprising glycosylated or deglycosylated human PlGF-1 or glycosylated human PlGF-1 fragment selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8.

In another aspect, provided herein is a diagnostic kit for the detection of human PlGF-1 or human PlGF-1 fragment, wherein the kit comprises:

(a) at least one calibrator or control a calibrator or control comprising glycosylated or deglycosylated human PlGF-1 or glycosylated human PlGF-1 fragment selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8.; and (b) instructions for using the kit. Optionally the kit further comprises at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539.

In still a further embodiment, the disclosure provides a diagnostic kit for the detection of human PlGF-1 or human PlGF-1 fragment, wherein the kit comprises:

(a) at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539;

(b) at least one calibrator or control a calibrator or control comprising glycosylated or deglycosylated human PlGF-1 or glycosylated human PlGF-1 fragment selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8; and (c) instructions for using the kit.

Furthermore, provided by the disclosure herein is an isolated or purified polynucleotide selected from the group consisting of SEQ ID NO:9, SEQ ID NO: 10, SEQ ID NO:11, SEQ ID NO: 12, SEQ ID NO:13, SEQ ID NO: 14, SEQ ID NO:15, SEQ ID NO:16, SEQ ID NO:22, SEQ ID NO:23, SEQ ID NO:26, SEQ ID NO:27, SEQ ID NO:28, SEQ ID NO:30 and SEQ ID NO:31.

DESCRIPTION OF THE FIGURES

FIG. 1 shows the polynucleotide sequence for human PlGF-1 (SEQ ID NO:22). The antibody kappa light chain signal sequence is shown in italics and the His tag is underlined.

FIG. 4 is a Western Blot showing the results of an assay as described in Example 2 which demonstrated that anti-human PlGF-1 monoclonal antibodies (namely, either monoclonal antibody 1-255-713 (255) or 2-826-335 (826)) bind to recombinant human PlGF-1 antigen in non-reduced forms.

FIG. 6 shows the polynucleotide sequence for human PlGF-1 fragment (SEQ ID NO:23). The antibody kappa light chain signal sequence is shown in italics and the His tag is underlined.

FIG. 9 shows the polynucleotide sequence for human PlGF-1 (SEQ ID NO:26). The antibody kappa light chain signal sequence is shown in italics and the His tag is underlined and the enterokinase cleavage site (DDDDK) is shown in bold.

FIG. 12 shows, in the top sequence, the variable light chain polynucleotide sequence for monoclonal antibody 1-255-713 (SEQ ID NOS:27 and 28). The bottom sequence, contains the complement of the top sequence, which is shown in the 3' to 5' direction.

FIG. 13 shows the amino acid sequence for the light chain of the monoclonal antibody 1-255-713 complementarity determining regions (CDR) 1, 2 and 3 are italicized and underlined (SEQ ID NO:29).

FIG. 14 shows, in the top sequence, the variable heavy chain polynucleotide sequence for monoclonal antibody 1-255-713 (SEQ ID NOS:30 and 31). The bottom sequence, contains the complement of the top sequence, which is shown in the 3' to 5' direction.

FIG. 15 shows the amino acid sequence for the heavy chain of the monoclonal antibody 1-255-713 CDR 1, 2 and 3 are italicized and underlined (SEQ ID NO:32).

FIG. 16 shows, in the top sequence, the variable light chain polynucleotide sequence for monoclonal antibody 2-826-335 (SEQ ID NOS:41 and 42). The bottom sequence, contains the complement of the top sequence, which is shown in the 3' to 5' direction.

FIG. 17 shows the amino acid sequence for the light chain of the monoclonal antibody 2-826-335 CDR 1, 2 and 3 are italicized and underlined (SEQ ID NO:43).

FIG. 18 shows, in the top sequence, the variable heavy chain polynucleotide sequence for monoclonal antibody 2-826-335 (SEQ ID NOS:33 and 34). The bottom sequence, contains the complement of the top sequence, which is shown in the 3' to 5' direction.

FIG. 19 shows the amino acid sequence for the heavy chain of the monoclonal antibody 2-826-335 CDR 1, 2 and 3 are italicized and underlined (SEQ ID NO:35).

FIG. 20 shows trypsin digested and deglycosylated human PlGF-1 (SEQ ID NO:40). At amino acid position 21, asparagine (N) was converted to aspartic acid (D) (shown in italics and bold) after deglycosylation. At position 89, both asparagine (N) and aspartic acid were detected (shown only in bold).

DETAILED DESCRIPTION

Figure 2:
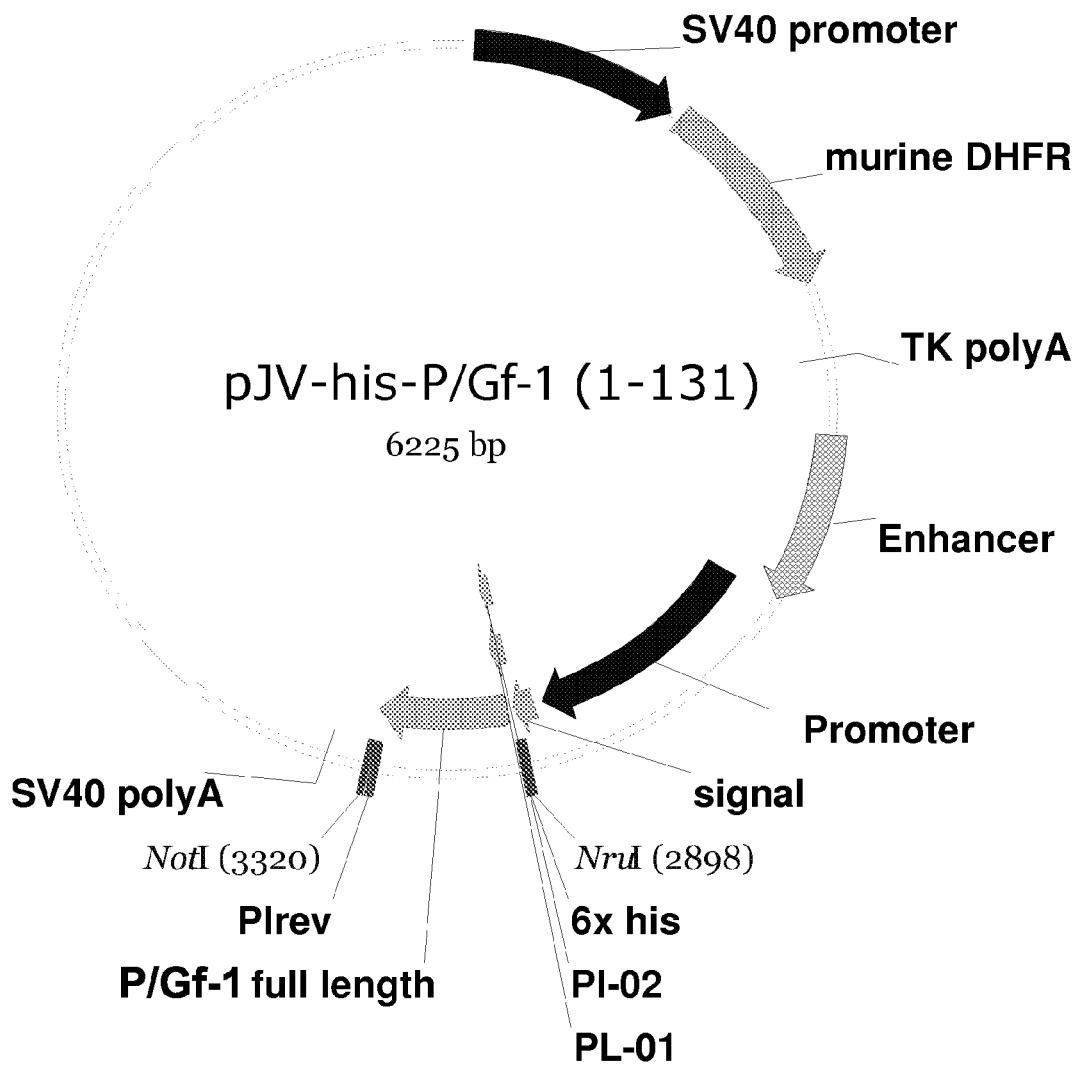
FIG. 2 shows the vector pJV-His-human PlGF-1 (1-131).

The present disclosure relates to human PlGF-1 proteins (i.e., glycosylated and deglycosylated human PlGF-1 proteins) and to antibodies that bind to certain human PlGF-1 proteins. The human PlGF-1 proteins alone or in or in combination with antibodies directed against the human PlGF-1 proteins have a variety of uses, for example, as a component of a diagnostic assay, or present in an immunoassay kit, or as immunogens for making antibodies in improved immunoassays.

A. Definitions

As used herein, the singular forms "a" "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antibody

As used herein, the terms "antibody" and "antibodies" refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, feline, canine, rat, murine, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present disclosure), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$), subclass, fragments or derivatives thereof. For simplicity sake, an antibody against an analyte is frequently referred to as being either an "anti-analyte antibody", or merely an "analyte antibody" (e.g., a human PlGF-1 antibody). The antibody may be derivatized by the attachment of one or more chemical, peptide, or polypeptide moieties known in the art. The antibody may be conjugated with a chemical moiety.

b) Binding Constants (e.g., $K_D$, $k_a$, and $k_d$).

The terms "equilibrium dissociation constant" or "$K_D$", as used interchangeably herein, refer to the value obtained in a titration measurement at equilibrium, or by dividing the dissociation rate constant ($k_{off}$) by the association rate constant ($k_{on}$). The association rate constant, the dissociation rate constant and the equilibrium dissociation constant are used to represent the binding affinity of an antibody to an antigen.

The term "association rate constant", "$k_{on}$" or "$k_a$" as used interchangeably herein, refers to the value indicating the binding rate of an antibody to its target antigen or the rate of complex formation between an antibody and antigen as shown by the equation below:

Antibody ("Ab")+Antigen ("Ag")→Ab–Ag.

The term "dissociation rate constant", "$k_{off}$" or "$k_d$" as used interchangeably herein, refers to the value indicating the dissociation rate of an antibody from its target antigen or separation of Ab-Ag complex over time into free antibody and antigen as shown by the equation below:

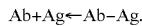

Ab+Ag←Ab–Ag.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

c) Cardiovascular Disease

As used herein, the phrase "cardiovascular disease" refers to various clinical diseases, disorders or conditions involving the heart, blood vessels or circulation. The diseases, disorders or conditions may be due to atherosclerotic impairment of coronary, cerebral or peripheral arteries. Cardiovascular disease includes, but is not limited to, coronary artery disease, peripheral vascular disease, hypertension, myocardial infarction, heart failure, etc. For example, in heart failure, "increased severity" of cardiovascular disease refers to the worsening of disease as indicated by increased NYHA classification, to, for example, Class III or Class IV and "reduced severity" of cardiovascular disease refers to an improvement of the disease as indicated by reduced NYHA classification, from, for example, class III or IV to class II or I.

d) Glycosylated Human PlGF-1 or Glycosylated Human PlGF-1 Fragment

As used herein, the phrases "oligosaccharide moiety" or "oligosaccharide molecule" as used interchangeably herein refers to a carbohydrate-containing molecule comprising one or more monosaccharide residues, capable of being attached to a polypeptide (to produce a glycosylated polypeptide, such as, for example, human PlGF-1 or human PlGF-1 fragment) by way of in vivo or in vitro glycosylation. Except where the number of oligosaccharide moieties attached to the polypeptide is expressly indicated, every reference to "oligosaccharide moiety" referred to herein is intended as a reference to one or more such moieties attached to a polypeptide. Preferably, the polypeptide to which said carbohydrate-containing molecule is capable of being attached is human PlGF-1 or human PlGF-1 fragment, i.e., to provide "glycosylated human PlGF-1" or "glycosylated human PlGF-1 fragment" as described further herein.

The term "in vivo glycosylation" is intended to mean any attachment of an oligosaccharide moiety occurring in vivo, for example, during posttranslational processing in a glycosylating cell used for expression of the polypeptide, for example, by way of N-linked and O-linked glycosylation. Usually, the N-glycosylated oligosaccharide-moiety has a common basic core structure composed of five monosaccharide residues, namely two N-acetylglucosamine residues and three mannose residues. The exact oligosaccharide structure depends, to a large extent, on the glycosylating organism in question and on the specific polypeptide.

The phrase "in vitro glycosylation" refers to a synthetic glycosylation performed in vitro, normally involving covalently linking an oligosaccharide moiety to an attachment group of a polypeptide, optionally using a cross-linking agent. In vitro glycosylation can be achieved by attaching chemically synthesized oligosaccharide structures to a polypeptide (such as, for example, human PlGF-1 or human PlGF-1 fragment) using a variety of different chemistries. For example, the chemistries that can be employed are those used for the attachment of polyethylene glycol (PEG) to proteins, wherein the oligosaccharide is linked to a functional group, optionally, via a short spacer. In vitro glycosylation can be carried out in a suitable buffer at a pH of about 4.0 to about 7.0 in protein concentrations of about 0.5 to about 2.0 mg/mL in a volume of about 0.02 to about 2.0 mL. Other in vitro glycosylation methods are described, for example in WO 87/05330, by Aplin et al., *CRC Crit. Rev. Biochem.* 259-306 (1981), by Lundblad et al. in *Chemical Reagents for Protein Modification*, CRC Press Inc., Boca Raton, Fla., Yan et al., *Biochemistry*, 23:3759-3765 (1982) and Doebber et al., *J. Biol. Chem.*, 257:2193-2199 (1982).

e) Heart Failure

As used herein, the phrase "heart failure" refers to a condition in which the heart cannot pump blood efficiently to the rest of the body. Heart failure may be due to damage to the heart or narrowing of the arteries due to infarction, cardiomyopathy (primary or secondary), hypertension, coronary artery disease, valve disease, birth defects or infection. Heart failure can further be described as chronic, congestive, acute, decompensated, systolic or diastolic. The New York Heart Association (NYHA) classification describes the severity of the disease based on functional capacity of the patient; NYHA class can progress and/or regress based on treatment or lack of response to treatment.

f) Human PlGF-1 Fragment

As used herein, the term "human PlGF-1 fragment" refers to a polypeptide that comprises a part that is less than the entirety (i.e., not full length) of a human PlGF-1 (131 amino acids, referred to by some as the mature protein) or PlGF-1 including a signal peptide (149 amino acids, referred to by some as the immature protein). In particular, a human PlGF-1 fragment comprises from about 5 to about 130 contiguous amino acids of SEQ ID NOS: 1, 2, 3 or 4. In particular, a human PlGF-1 fragment comprises at least about 5 contiguous amino acids of SEQ ID NO: 1, 2, 3 or 4, at least about 10 contiguous amino acids residues of SEQ ID NOS: 1, 2, 3 or 4; at least about 15 contiguous amino acids residues of amino acids of SEQ ID NOS: 1, 2, 3 or 4; at least about 20 contiguous amino acids residues of SEQ ID NOS: 1, 2, 3 or 4; at least about 25 contiguous amino acids residues of SEQ ID NOS: 1, 2, 3 or 4, at least about 30 contiguous amino acid residues of amino acids of SEQ ID NOS: 1, 2, 3 or 4, at least about 35 contiguous amino acid residues of SEQ ID NOS: 1, 2, 3 or 4, at least about 40 contiguous amino acid residues of SEQ ID NOS: 1, 2, 3 or 4, at least about 45 contiguous amino acid residues of SEQ ID NOS: 1, 2, 3 or 4, at least about 50 contiguous amino acid residues of SEQ ID NOS:1, 2, 3 or 4, at least about 55 contiguous amino acid residues of SEQ ID NOS:1, 2, 3 or 4, at least about 60 contiguous amino acid residues of SEQ ID NOS:1, 2, 3 or 4, at least about 65 contiguous amino acid residues of SEQ ID NOS:1, 2, 3 or 4, at least about 70 contiguous amino acid residues of SEQ ID NOS:1, 2, 3 or 4, at least about 75 contiguous amino acid residues of SEQ ID NOS:1, 2, 3 or 4, at least about 80 contiguous amino acid residues of SEQ ID NOS:1, 2, 3 or 4, at least about 85 contiguous amino acid residues of SEQ ID NOS:1, 2, 3 or 4, at least about 90 contiguous amino acid residues of SEQ ID NOS:1, 2, 3 or 4, at least about 95 contiguous amino acid residues of SEQ ID NOS:1, 2, 3 or 4, at least about 100 contiguous amino acid residues of SEQ ID NOS:1, 2, 3 or 4, at least about 105 contiguous amino acid residues of SEQ ID NOS:1, 2, 3 or 4, at least about 110 contiguous amino acid residues of SEQ ID NOS:1, 2, 3 or 4, at least about 115 contiguous amino acid residues of SEQ ID NOS:1, 2, 3 or 4, at least about 120 contiguous amino acid residues of SEQ ID NOS:1, 2, 3 or 4, at least about 125 contiguous amino acid residues of SEQ ID NOS:1, 2, 3 or 4 or 130 contiguous amino acid residues of SEQ ID NOS:1, 2, 3 or 4.

Examples of human PlGF-1 fragments contemplated by the present disclosure include, but are not limited to:

(a) a human PlGF-1 fragment of at least about 115 contiguous amino acids having the amino acid sequence shown in SEQ ID NO:5;

(b) a human PlGF-1 fragment of at least about 121 contiguous amino acids having the amino acid sequence shown in SEQ ID NO:6 (which is identical to SEQ ID NO:5 but includes a linking sequence, specifically, a His tag (HHH-HHH (SEQ ID NO:17));

(c) a human PlGF-1 fragment of at least about 122 contiguous amino acids having the amino acid sequence shown in SEQ ID NO:7 (which is identical to SEQ ID NO:5, but includes a linking sequence, specifically, an enterokinase cleavage site (DDDDK (SEQ ID NO:18)); and (d) a human PlGF-1 fragment of at least about 128 contiguous amino acids having the amino acid sequence shown in SEQ ID NO:8 (SEQ ID NO:8 is identical to SEQ ID NO:5, but includes two linking sequences, specifically a His tag (HHHHHH (SEQ ID NO:17)) and an enterokinase cleavage site (DDDDK (SEQ ID NO:18)).

g) Human PlGF-1 Polynucleotide

As used herein, the phrase "human PlGF-1 polynucleotide" refers to a polynucleotide encoding human PlGF-1 or a human PlGF-1 fragment. The human PlGF-1 polynucleotide can be isolated, purified or isolated and purified. The human PlGF-1 polynucleotide of the present disclosure can be either RNA or DNA (e.g., cDNA, genomic DNA or synthetic DNA). The DNA is either double-stranded or single-stranded, and, if single-stranded, is either the coding strand or non-coding (antisense) strand.

An exemplary human PlGF-1 polynucleotide of the present disclosure is an isolated, a purified, or isolated and purified human PlGF-1 polynucleotide comprising or consisting of (a) SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:22, SEQ ID NO:23 or SEQ ID NO:26; and (b) a polynucleotide sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the entire sequence of SEQ ID NO:9, SEQ ID NO:10, SEQ ID NO:11, SEQ ID NO:12 SEQ ID NO:13, SEQ ID NO:14, SEQ ID NO:15 SEQ ID NO:16, SEQ ID NO:22, SEQ ID NO:23 or SEQ ID NO:26. SEQ ID NO:9 is the polynucleotide sequence of the full length human PlGF-1 sequence of SEQ ID NO:1. SEQ ID NO:10 is the polynucleotide sequence of the full length human PlGF-1 sequence of SEQ ID NO:2 containing the His tag. SEQ ID NO:11 is the polynucleotide sequence of the full length human PlGF-1 sequence of SEQ ID NO:3 containing the enterokinase cleavage site, except that SEQ ID NO:11 does not recite the polynucleotide sequence of the N-terminal GlyAla of SEQ ID NO:3. SEQ ID NO:12 is the polynucleotide sequence of the full length human PlGF-1 sequence of SEQ ID NO:4 containing the His tag and enterokinase cleavage site. SEQ ID NO:13 is the polynucleotide sequence of the human PlGF-1 fragment having the sequence of SEQ ID NO:5. SEQ ID NO:14 is the polynucleotide sequence of the human PlGF-1 fragment having the sequence of SEQ ID NO:6 containing the His tag. SEQ ID NO:15 is the polynucleotide sequence of the human PlGF-1 fragment having the sequence of SEQ ID NO:7 containing the enterokinase cleavage site, except that SEQ ID NO:15 does not recite the polynucleotide sequence of the N-terminal GlyAla of SEQ ID NO:7. SEQ ID NO:16 is the polynucleotide sequence of the human PlGF-1 fragment having the sequence of SEQ ID NO:8 containing the His tag and enterokinase cleavage site. SEQ ID NO:22 is the polynucleotide sequence of the full length human PlGF-1 sequence of SEQ ID NO:2 containing the His tag as well as an antibody kappa light chain signal sequence. SEQ ID NO:23 is the polynucleotide sequence of the full length human PlGF-1 sequence of SEQ ID NO:6 containing the His tag as well as an antibody kappa light chain signal sequence. SEQ ID NO:26 is the polynucleotide sequence of SEQ ID NO:4 containing the His tag, enterokinase cleavage site as well as an antibody kappa light chain signal sequence.

h) Human PlGF-1 or Human PlGF-1 Polypeptide

The phrases "human PlGF-1" or "human PlGF-1 polypeptide" as used interchangeably herein refer to any full length (i.e., not a fragment thereof) human PlGF-1 sequence, either with or without a signal peptide. For example, the full length human PlGF-1 can be a 149 amino acid immature polypeptide with an 18 amino acid signal sequence having a centrally located PDGF-like domain with 8 conserved cysteine residues that form a cysteine knot structure. Alternatively, the human PlGF-1 can be a 131 amino acid mature polypeptide that does not contain the 18 amino acid signal sequence (such as that shown in SEQ ID NO: 1). The PlGF may exist in at least four alternatively spliced forms: PlGF-1, PlGF-2, PlGF-3 and PlGF-4. PlGF-2 and PlGF-4 may differ from other forms by the insertion of a heparin-binding domain in PlGF-2 and PlGF-4 that may result in increased association with the cell membrane or altered affinities for PlGF receptors. Human PlGF-1 polynucleotide and polypeptide (e.g., polyamino acid) sequences are as found in nature, based on sequences found in nature, isolated, synthetic, semi-synthetic, recombinant, or other.

Accordingly, the disclosure herein encompasses a multitude of different human PlGF-1 polynucleotide and polypeptide sequences as present and/or produced in a prokaryotic and/or eukaryotic background (e.g., with consequent optimization for codon recognition). In sum, the human PlGF-1 polynucleotide and polypeptide sequences may or may not comprise: (a) one or more signal sequences (e.g., a signal peptide); (b) one or more linking sequences; and (c) other variations such as would be apparent to one skilled in the art.

Exemplary sequences include, but are not limited to, those as set forth herein, namely (a) SEQ ID NO: 1 (which is human PlGF-1 which comprises 131 amino acids and which does not contain a signal sequence or any linking sequences), SEQ ID NO:2 (SEQ ID NO:2 is identical to SEQ ID NO: 1 but includes a linking sequence, specifically, a His tag (HHHHHH (SEQ ID NO: 17)), SEQ ID NO:3 (SEQ ID NO:3 is identical to SEQ ID NO: 1, but includes a linking sequence, specifically, a enterokinase cleavage site (DDDDK (SEQ ID NO:18)), or SEQ ID NO:4 (SEQ ID NO:4 is identical to SEQ ID NO: 1, but includes two linking sequences, specifically a His tag (HHHHHH (SEQ ID NO: 17)) and a enterokinase cleavage site (DDDDK (SEQ ID NO: 18)); and (b) a polypeptide that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% identical to the entire sequence of SEQ ID NO: 1, SEQ ID NO:2, SEQ ID NO:3 or SEQ ID NO:4.

i) Hypertensive Disorder of Pregnancy

A "hypertensive disorder of pregnancy (HDP)" is used herein in the context defined by the National Heart, Lung and Blood Institute (NHLBI) (see Roberts, et al. (2003) *Hypertension* 41(3): 437-45). The NHLBI classify the HDP into 4 categories:

Pre-eclampsia (PE) defined as: blood pressure (BP)≥140/90; >300 mg/24 h proteinuria at >20 weeks gestation.

Chronic Hypertension (CHTN) defined as: BP≥140/90 prior to pregnancy or <20 weeks gestation.

Superimposed pre-eclampsia on chronic hypertension (PE+CHTN) defined as: the development of newly increased proteinuria in a woman with existing chronic hypertension>20 weeks of gestation.

Gestational Hypertension (GH) defined as: hypertension without proteinuria at >20 weeks.

Comparison of these measurements with pre-determined values allows the hypertensive status of the subject to be determined, for example, to distinguish between pre-eclampsia and chronic hypertension.

j) Hypertensive Status

As used herein, the term "hypertensive status," refers to the condition of a subject with respect to the presence or absence of a hypertensive disorder, for example chronic hypertension, a hypertensive disorder associated with pregnancy (HDP), or a hypertensive disorder associated with anti-angiogenic drug therapy.

k) Identical

"Identical" or "identity" as used herein in the context of two or more polypeptide or polynucleotide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

l) Immunodiagnostic Reagent

An "immunodiagnostic reagent" according to the present disclosure comprises one or more antibodies that specifically bind to a region of human PlGF-1 or human PlGF-1 fragment. The use of such antibodies of the present disclosure, e.g., in immunoassays and/or as calibrators, controls, and immunodiagnostic agents, is described herein. However, the antibodies of the subject invention also optionally can be employed in improved human PlGF-1 assays as described herein.

m) Linking Sequence

As used herein, the phrase "linking sequence" refers to a natural or artificial polypeptide sequence that is connected to one or more polypeptide sequences of interest (e.g, full length, fragments, etc.). The term "connects" refers to the joining of the linking sequence to the polypeptide sequence of interest. Such polypeptide sequences are preferably joined by one or more peptide bonds.

Linking sequences can have a length of from about 4 to about 50 amino acids. Preferably, the length of the linking sequence is from about 6 to about 30 amino acids. Natural linking sequences may be modified by amino acid substitutions, additions, or deletions to create artificial linking sequences.

Exemplary linking sequences include, but are not limited to:

(a) Histidine (His) tags, such as a 6×His tag which has an amino acid sequence of HHHHHH (SEQ ID NO: 17). Histidine tags are useful as linking sequences to facilitate the isolation and purification of polypeptides and antibodies of interest.

(b). Enterokinase cleavage sites. Enterokinase cleavage sites, like His tags, used in the isolation and purification of proteins and antibodies of interest. Often, enterokinase cleavage sites are used together with His tags in the isolation and purification of proteins and antibodies of interest. A variety of enterokinase cleavage sites are known in the art. An example of enterokinase cleavage site includes, but is not limited to the amino acid sequence of DDDDK (SEQ ID NO: 18) and derivatives thereof (e.g, ADDDDK, etc.).

(c) Miscellaneous sequences. Such sequences include linking sequences such as the amino acid sequence GPAKELTPLKEAKVS (SEQ ID NO: 19) which can be used to link or connect the light and/or heavy chain variable regions of single chain variable region fragments. Examples of other linking sequence that can be used can be found in Bird et al., *Science*, 242:423-426 (1988), Huston et al., *Proc. Natl. Acad. Sci. USA*, 85:5879-5883 (1988) and McCafferty et al., *Nature*, 348:552-554 (1990). Linking sequences can also be modified for additional functions, such as attachment of drugs or attachment to solid supports.

In the present disclosure, the polypeptides (e.g., the glycosylated and deglycosylated full length and fragment forms of human PlGF-1 polypeptide) and antibodies of interest may contain one or more linking sequences. For example, the polypeptides and antibodies of the present disclosure may contain a His tag, a enterokinase cleavage site or both a His tag and an enterokinase cleavage site.

n) On Average

As used herein, the term "on average" refers to a single value that represents the typical example of a group of values under consideration or review.

o) PlGF-1 Hybrid

As used herein, the term "PlGF-1 hybrid" or "PlGF-1 hybridoma" refers to a particular hybridoma clone or subclone (as specified) that produces an anti-PlGF-1 antibody of interest. Generally, there may be some small variation in the affinity of antibodies produced by a hybridoma clone as compared to those from a subclone of the same type, e.g., reflecting purity of the clone. By comparison, it is well established that all hybridoma subclones originating from the same clone and further, that produce the anti-PlGF-1 antibody of interest produce antibodies of identical sequence and/or identical structure.

p) Pre-eclampsia

As used herein, the term "pre-eclampsia," refers to both a multi-system disorder that is observed during pregnancy (characterized by hypertension with or before the onset of proteinuria and/or other symptoms of pre-eclampsia (see below)), as well as "pre-eclampsia-like syndrome" (PLS) associated with anti-angiogenic treatment (e.g., chemotherapy). The term "pre-eclampsia" encompasses the NHLBI HDP designation of "pre-eclampsia/eclampsia", as well the various clinical forms of the disorder, including mild, moderate, and severe pre-eclampsia. "Pre-eclampsia" also includes HELLP syndrome, a variant of severe pre-eclampsia associated with hemolysis, elevated liver enzyme levels, and low platelet count.

The term "pre-eclampsia-like syndrome (PLS)" refers to a multi-system disorder that is observed during anti-angiogenic treatment (e.g., chemotherapy), which is characterized by the new onset of hypertension with or without proteinuria, and potentially other symptoms of pre-eclampsia (see below).

The term "symptoms of pre-eclampsia" refers to both patient physical and analytical findings and complaints including hypertension (a systolic blood pressure (BP) greater than 140 mmHg and a diastolic BP greater than 90 mmHg after 20 weeks gestation); new onset proteinuria (1+ by dipstick on urinanalysis, greater than 300 mg of protein in a 24 hour urine collection, or random urine protein/creatinine ratio greater than 0.3), and resolution of hypertension and proteinuria by 26 weeks postpartum, or upon cessation of anti-angiogenic therapy. The symptoms of pre-eclampsia can also include renal dysfunction, glomerular endotheliosis, edema, neuropathy, coagulopathy and/or fatigue.

q) Pretreatment Reagent (e.g., Lysis, Precipitation and/or Solubilization Reagent)

A pretreatment reagent used in a diagnostic assay as described herein is one that lyses any cells and/or solubilizes any analyte that are present in a test sample. Pretreatment is not necessary for all samples, as described further herein. Among other things, solubilizing the analyte (i.e., human PlGF-1 or human PlGF-1 fragment) entails release of the analyte from any endogenous binding proteins present the sample. A pretreatment reagent may be homogenous (not requiring a separation step) or heterogeneous (requiring a separation step). With use of a heterogenous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

r) Solid Phase

A "solid phase," as used herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

s) Substantially Identical

"Substantially identical," as used herein may mean that a first and second sequence are at least from about 50% to about 99% identical over a region of from about 8 to about 100 or more residues (including, in particular, any range within from about 8 to about 100 residues).

t) Variant

"Variant" as used herein may mean a peptide or polypeptide that differs in amino acid sequence by the insertion, deletion, or conservative substitution of amino acids, but retain at least one biological activity. For purposes of this disclosure, "biological activity" includes the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated herein by reference. Substitution of amino acids having similar hydrophilicity values can result in peptides retaining biological activity, for example immunogenicity, as is understood in the art. In one aspect, substitutions are performed with amino acids having hydrophilicity values within±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Variant may also refer to a protein that is (i) a portion of a referenced protein which may be from about 8 to about 100 or more amino acids (including, in particular, any range within from about 8 to about 100 residues); or (ii) a protein that is substantially identical to a referenced protein. A variant may also be a differentially processed protein, such as by proteolysis, phosphorylation, or other post-translational modification.

u) Subject

As used herein, the terms "subject" and "patient" are used interchangeably irrespective of whether the subject has or is currently undergoing any form of treatment. As used herein, the terms "subject" and "subjects" refer to a mammal including, a non-primate (for example, a cow, pig, camel, llama, horse, goat, rabbit, sheep, hamsters, guinea pig, feline, canine, rat, and murine), a non-human primate (for example, a monkey, such as a cynomologous monkey, chimpanzee, etc) and a human. Preferably, the subject is a human.

v) Test Sample

As used herein, the term "test sample" generally refers to a biological material being tested for and/or suspected of containing an analyte of interest, such as a human PlGF-1 or human PlGF-1 fragment. The test sample may be derived from any biological source, such as, a physiological fluid, including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

The terminology used herein is for the purpose of describing particular embodiments only and is not otherwise intended to be limiting.

B. Glycosylated and Deglycosylated Human PlGF-1 and Human PlGF-1 Fragments

In one aspect, the present disclosure relates to human PlGF-1 forms of any type (e.g., isolated, recombinant, mutant, synthetic, semi-synthetic, etc.). The human PlGF-1 forms of the present disclosure can be a human PlGF-1, a human PlGF-1 fragment or mutant forms of the human PlGF-1 or human PlGF-1 fragment. The human PlGF-1 and human PlGF-1 fragments described herein can each optionally be glycosylated. Moreover, glycosylated forms of human PlGF-1 or human PlGF-1 fragments can optionally be deglycosylated using one of more techniques known in the art to produce deglycosylated forms of human PlGF-1 or PlGF-1 fragments. Each of these human PlGF-1 forms can be employed, e.g., as immunogens for making antibodies, and/or in assessing binding of such antibodies. Moreover, the human PlGF-1 fragments, including any that may be optionally glycosylated or deglycosylated, can be used as one or calibrators or controls in an immunoassay.

In one embodiment, the present disclosure relates to the use of isolated glycosylated human PlGF-1. More specifically, the present disclosure relates to glycosylated human PlGF-1 that contains at least one oligosaccharide molecule or moiety and up to about ten (10) oligosaccharide molecules or moieties. For example, the glycosylated human PlGF-1 of the present disclosure can be a full length human PlGF-1 having an amino acid sequence of 131 amino acids such as that shown in SEQ ID NO: 1. Specifically, the full length human PlGF-1 having the amino acid sequence shown in SEQ ID NO: 1 or SEQ ID NO:2 can be glycosylated at the asparagine shown at amino acid 15 or 83 of SEQ ID NO: 1 (which will result in N-linked glycosylation), at the asparagine shown at amino acid 21 or 89 of SEQ ID NO:2 (which will result in N-linked glycosylation) and at any or all of the serine residues shown at amino acids 1, 17, 18, 32, 45, 49, 56, 58, 61, 93, 98 and 105 of SEQ ID NO:1 (which will result in O-linked glycosylation). Alternatively, the glycosylated human PlGF-1 of the present disclosure can have the amino acid sequences shown in SEQ ID NO:3 or SEQ ID NO:4.

The isolated or purified glycosylated human PlGF-1 forms of the present disclosure may contain different percentages of glycosylation for certain amino acid residues. For example, amino acid residue 15 of SEQ ID NO:1 is on average about 70% glycosylated and amino acid residue 83 of SEQ ID NO:1 is on average about 100% glycosylated when compared to the wild-type sequence. Alternatively, amino acid residue 21 of SEQ ID NO:2 is on average about 70% glycosylated and amino acid residue 89 of SEQ ID NO:2 is on average about 100% glycosylated when compared to the wild-type sequence.

The isolated or purified human PlGF-1 forms of the present disclosure having the amino acid sequence shown in SEQ ID NO: 1 or SEQ ID NO:2 can be glycosylated at least one asparagine shown at amino acid 15, 83 or 15 and 83 of SEQ ID NO: 1 or at least one asparagine shown at amino acid 21, 89 or 21 and 89 of SEQ ID NO:2 with at least one N-glycan. The at least one glycan having a structure selected from the group consisting of: (a) N-acetylneuraminic acid(Galactose)$_2$(Mannose)$_3$(N-acetyl-D-glucosamine)$_4$Fucose, (b) (N-acetylneuraminic acid)$_2$(Galactose)$_2$(Mannose)$_3$(N-acetyl-D-glucosamine)$_4$Fucose, (c) (N-acetylneuraminic acid)$_2$ (Galactoseβ1-4N-acetyl-D-glucosamine)$_2$(Galactose)$_2$ (Mannose)$_3$ (N-acetyl-D-glucosamine)$_4$Fucose or (Galactoseβ1-4N-acetyl-D-glucosamine)(Galactose)$_3$(Mannose)$_3$(N-acetyl-D-glucosamine)$_5$Fucose; (d) (N-acetylneuraminic acid)$_2$(Galactose)$_3$(Mannose)$_3$(N-acetyl-D-glucosamine)$_5$Fucose; (e) (N-acetylneuraminic acid)$_3$ (Galactose)$_3$(Mannose)$_3$(N-acetyl-D-glucosamine)$_5$Fucose; (f) (N-acetylneuraminic acid)$_3$(Galactoseβ1-4N-acetyl-D-glucosamine) (Galactose)$_3$ (Mannose)$_3$ (N-acetyl-D-glucosamine)$_5$Fucose or (N-acetylneuraminic acid)$_3$ (Galactose)$_4$(Mannose)$_3$ (N-acetyl-D-glucosamine)$_6$Fucose; (g) (N-acetylneuraminic acid)$_4$(Galactose)$_4$(Mannose)$_3$(N-acetyl-D-glucosamine)$_6$Fucose; and (h) (N-acetylneuraminic acid)$_4$(Galactoseβ1-4N-acetyl-D-glucosamine) (Galactose)$_4$ (Mannose)$_3$ (N-acetyl-D-glucosamine)$_6$Fucose.

Alternatively, the glycosylated human PlGF-1 of the present disclosure can be a human PlGF-1 fragment. An exemplary glycosylated human PlGF-1 fragment is a human PlGF-1 fragment having an amino acid sequence of 115 amino acids such as that shown in SEQ ID NO:5. For example, the human PlGF-1 fragment having the amino acid sequence shown in SEQ ID NO:5 can be glycosylated at any or all of the serine residues shown at amino acids 1, 2, 16, 29, 33, 40, 42, 45, 77, 82 or 89 of SEQ ID NO:5 (which will result in O-linked glycosylation). The human PlGF-1 fragment having the sequence of SEQ ID NO:5 does not exhibit N-linked glycosylation like the full length human PlGF-1 of SEQ ID NO: 1 because the human PlGF-1 fragment of SEQ ID NO:5 does not contain the N-terminal asparagine at amino acid 15 of SEQ ID NO: 1. Other exemplary glycosylated human PlGF-1 fragments of the present disclosure are provided for in amino acid sequences shown in SEQ ID NO:6, SEQ ID NO:7 or SEQ ID NO:8.

Alternatively, the glycosylated human PlGF-1 can be a glycosylated mutant human human PlGF-1 (e.g., any of SEQ ID NOS: 1-4) or glycosylated mutant human PlGF-1 fragments (e.g., any of SEQ ID NOS:5-8) that comprise an amino acid sequence comprising one or more amino acid substitutions, deletions or additions when compared to the corresponding amino acid sequence of SEQ ID NOS: 1-8. For example, the glycosylated human PlGF-1 can be a human PlGF-1 wherein the amino acid sequence of the human PlGF-1 (See, e.g., SEQ ID NOS:1-4) contains at least one amino acid substitution, deletion or addition. Optionally, the glycosylated human PlGF-1 can be a human PlGF-1 fragment wherein the amino acid sequence of the human PlGF-1 fragments (See, e.g., SEQ ID NOS:5-8) contains at least one amino acid substitution, deletion or addition. Such amino acid substitutions, deletions or additions can be made using routine techniques known to those skilled in the art.

The human PlGF-1 forms of the present disclosure can be made using recombinant DNA technology, by chemical synthesis or by a combination of chemical synthesis and recombinant DNA technology. Specifically, a polynucleotide sequence encoding a human PlGF-1 or human PlGF-1 fragment may be constructed by isolating or synthesizing a polynucleotide sequence encoding the human PlGF-1 or human PlGF-1 fragment of interest. For example, any of the polynucleotides of SEQ ID NO:9, SEQ ID NO:10, SEQ ID NO:1, SEQ ID NO: 12, SEQ ID NO:13, SEQ ID NO: 14, SEQ ID NO:15, SEQ ID NO:16, SEQ ID NO:22, SEQ ID NO:23 or SEQ ID NO:26 can be used. As mentioned above, the human PlGF-1 (e.g., optionally glycosylated) can be a full length human PlGF-1, a human PlGF-1 fragment, a mutant human PlGF-1 or a mutant human PlGF-1 fragment containing one more amino acid substitutions, deletions or additions. Such amino acid substitutions, deletions or additions can be made using routine techniques known in the art, such as by mutagenesis (for example, using site-directed mutagenesis in accordance with well known methods, e.g., as described in Nelson and Long, *Analytical Biochemisty* 180:147-151 (1989), random mutagenesis, or shuffling).

The polynucleotide sequence encoding any of the human PlGF-1 forms of interest may be prepared by chemical synthesis, such as by using an oligonucleotide synthesizer, wherein oligonucleotides are designed based on the amino acid sequence of the desired human PlGF-1 form of interest (namely, a full length human PlGF-1, a human PlGF-1 fragment, a mutant form of human PlGF-1 or a mutant form of human PlGF-1 fragment), and by preferably selecting those codons that are favored in the host cell in which the recombinant human PlGF-1 form of interest will be produced. For example, several small oligonucleotides coding for portions of the desired human PlGF-1 form of interest may be synthesized and assembled by polymerase chain reaction (PCR), ligation or ligation chain reaction (LCR). The individual oligonucleotides typically contain 5' or 3' overhangs for complementary assembly.

Once assembled (such as by synthesis, site-directed mutagenesis or another method), the polynucleotide sequence encoding the human PlGF-1 form of interest may be inserted into a recombinant vector and operably linked to any control sequences necessary for expression of thereof in the desired transformed host cell.

Although not all vectors and expression control sequences may function equally well to express a polynucleotide sequence of interest and not all hosts function equally well with the same expression system, it is believed that those skilled in the art will be able to easily make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors can also be considered. These include, but are not limited to, the relative strength of the sequence, its controllability, and its compatibility with the polynucleotide sequence encoding the human PlGF-1 form of interest, particularly as regards potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products coded for by the nucleotide sequence, etc.

The recombinant vector may be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector, in which the polynucleotide sequence encoding the human PlGF-1 form of interest is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include, pcDNA3.1 (+)\Hyg (Invitrogen Corp., Carlsbad, Calif.) and pCI-neo (Stratagene, La Jolla, Calif., USA). Examples of expression vectors for use in yeast cells include, but are not limited to, the 2µ plasmid and derivatives thereof, the POT1 vector (See, U.S. Pat. No. 4,931,373), the pJSO37 vector (described in Okkels, *Ann. New York Acad. Sci.*, 782:202-207, (1996)) and pPICZ A, B or C (Invitrogen Corp., Carlsbad, Calif.). Examples of expression vectors for use in insect cells include, but are not limited to, pVL941, pBG311 (Cate et al., "Isolation of the Bovine and Human Genes for Mullerian Inhibiting Substance And Expression of the Human Gene In Animal Cells" *Cell*, 45:685-698 (1986), pBluebac 4.5 and pMelbac (both of which are available from Invitrogen Corp., Carlsbad, Calif.). A preferred vector for use in the invention is pJV (available from Abbott Laboratories, Abbott Bioresearch Center, Worcester, Mass.).

Other vectors that can be used allow the polynucleotide sequence encoding the human PlGF-1 form of interest to be amplified in copy number. Such amplifiable vectors are well known in the art. These vectors include, but are not limited to, those vector that can be amplified by DHFR amplification (See, for example, Kaufman et al., "Construction Of A Modular Dihydrofolate Reductase cDNA Gene: Analysis Of Signals Utilized For Efficient Expression" *Mol. Cell. Biol.*, 2:1304-1319 (1982)) and glutamine synthetase (GS) amplification (See, for example, U.S. Pat. No. 5,122,464 and EP Patent Publication No. 0 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2µ replication genes REP 1-3 and origin of replication.

The vector may also comprise a selectable marker, namely, a gene or polynucleotide, the product of which complements a defect in the host cell, such as the gene coding for dihydrofolate reductase (DHFR) or the *Schizosaccharomyces pombe* TPI gene (See, P. R. Russell, *Gene*, 40: 125-130 (1985)), or one which confers resistance to a drug, such as, ampicillin, kanamycin, tetracycline, chloramphenicol, neomycin, hygromycin or methotrexate. For filamentous fungi, selectable markers include, but are not limited to, amdS, pyrG, arcB, niaD and sC.

As used herein, the phrase "control sequences" refers to any components, which are necessary or advantageous for the expression of the human PlGF-1 form of interest. Each control sequence may be native or foreign to the nucleic acid sequence encoding the human PlGF-1. Such control sequences include, but are not limited to, a leader, polyadenylation sequence, propeptide sequence, promoter, enhancer or upstream activating sequence, signal peptide sequence and transcription terminator. At a minimum, the control sequences include at least one promoter operably linked to the polynucleotide sequence encoding the human PlGF-1 form of interest.

As used herein, the phrase "operably linked" refers to the covalent joining of two or more polynucleotide sequences, by means of enzymatic ligation or otherwise, in a configuration relative to one another such that the normal function of the sequences can be performed. For example, a polynucleotide sequence encoding a presequence or secretory leader is operably linked to a polynucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the polynucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

A wide variety of expression control sequences may be used in the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, *J Mol. Biol.*, 196:947-50 (1987)).

In order to improve expression in mammalian cells a synthetic intron may be inserted in the 5' untranslated region of the polynucleotide sequence encoding the human PlGF-1 form of interest. An example of a synthetic intron is the synthetic intron from the plasmid pCI-Neo (available from Promega Corporation, WI, USA).

Examples of suitable control sequences for directing transcription in insect cells include, but are not limited to, the polyhedrin promoter, the P10 promoter, the baculovirus immediate early gene 1 promoter and the baculovirus 39K delayed-early gene promoter and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator and the ADH3 terminator.

The polynucleotide sequence encoding the human PlGF-1 form of interest may or may not also include a polynucleotide sequence that encodes a signal peptide. The signal peptide is present when the human PlGF-1 form of interest is to be secreted from the cells in which it is expressed. Such signal peptide, if present, should be one recognized by the cell chosen for expression of the polypeptide. The signal peptide may be homologous (for example, it may be that normally associated with the human PlGF-1 form of interest) or heterologous (namely, originating from another source than the human PlGF-1 form of interest) to the human PlGF-1 form of interest or may be homologous or heterologous to the host cell, namely, be a signal peptide normally expressed from the host cell or one which is not normally expressed from the host cell. Accordingly, the signal peptide may be prokaryotic, for example, derived from a bacterium, or eukaryotic, for example, derived from a mammalian, or insect, filamentous fungal or yeast cell.

The presence or absence of a signal peptide will, for example, depend on the expression host cell used for the production of the human PlGF-1 form of interest. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide may be derived from an insect gene (See, WO 90/05783), such as the lepidopteran *Manduca sexta* adipokinetic hormone precursor, (See, U.S. Pat. No. 5,023,328), the honeybee melittin (Invitrogen Corp., Carlsbad, Calif.), ecdysteroid UDP glucosyltransferase (egt) (Murphy et al., *Protein Expression and Purification* 4: 349-357 (1993), or human pancreatic lipase (hpl) (*Methods in Enzymology*, 284:262-272 (1997)).

Specific examples of signal peptides for use in mammalian cells include murine Ig kappa light chain signal peptide (Coloma, M, *J. Imm. Methods,* 152:89-104 (1992)). For use in yeast cells suitable signal peptides include the α-factor signal peptide from *S. cerevisiae* (See, U.S. Pat. No. 4,870,008), the signal peptide of mouse salivary amylase (See, O. Hagenbuchle et al., *Nature,* 289:643-646 (1981)), a modified carboxypeptidase signal peptide (See, L. A. Valls et al., *Cell,* 48:887-897 (1987)), the yeast BAR1 signal peptide (See, WO 87/02670), and the yeast aspartic protease 3 (YAP3) signal peptide (See, M. Egel-Mitani et al., *Yeast,* 6:127-137 (1990)).

Any suitable host may be used to produce the glycosylated human PlGF-1 form of interest (e.g., human PlGF-1, human PlGF-1 fragment, mutant human PlGF-1 or mutant human PlGF-1 fragment) of the present disclosure, including bacteria, fungi (including yeasts), plant, insect mammal or other appropriate animal cells or cell lines, as well as transgenic animals or plants. When a non-glycosylating organism such as *E. coli* is used, the expression in *E. coli* is preferably followed by suitable in vitro glycosylation in order to produce the glycosylated human PlGF-1 form of interest of the present disclosure.

Examples of bacterial host cells include, but are not limited to, gram positive bacteria such as strains of *Bacillus,* for example, *B. brevis* or *B. subtilis, Pseudomonas* or *Streptomyces*, or gram negative bacteria, such as strains of *E. coli*. The introduction of a vector into a bacterial host cell may, for instance, be effected by protoplast transformation (See, for example, Chang et al., *Molecular General Genetics,* 168: 111-115 (1979)), using competent cells (See, for example, Young et al., *Journal of Bacteriology,* 81:823-829 (1961)), or Dubnau et al., *Journal of Molecular Biology,* 56:209-221 (1971)), electroporation (See, for example, Shigekawa et al., *Biotechniques,* 6:742-751 (1988)), or conjugation (See, for example, Koehler et al., *Journal of Bacteriology,* 169:5771-5278 (1987)).

Examples of suitable filamentous fungal host cells include, but are not limited to, strains of *Aspergillus,* for example, *A. oryzae, A. niger,* or *A. nidulans, Fusarium* or *Trichoderma*. Fungal cells may be transformed by a process involving protoplast formation, transformation of the protoplasts, and regeneration of the cell wall using techniques known to those skilled in the art. Suitable procedures for transformation of *Aspergillus* host cells are described in EP Patent Application 238 023 and U.S. Pat. No. 5,679,543. Suitable methods for transforming *Fusarium* species are described by Malardier et al., *Gene,* 78:147-156 (1989) and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al, *Journal of Bacteriology,* 153:163 (1983); and Hinnen et al., *Proceedings of the National Academy of Sciences USA,* 75:1920 (1978).

Preferably, the human PlGF-1 form of interest of the present disclosure is glycosylated in vivo. When the human PlGF-1 form of interest is to be glycosylated in vivo, the host cell is selected from a group of host cells capable of generating the desired glycosylation of the human PlGF-1 form of interest. Thus, the host cell may be selected from a yeast cell, insect cell, or mammalian cell.

Examples of suitable yeast host cells include strains of *Saccharomyces,* for example, *S. cerevisiae,* Schizosaccharomyces, Klyveromyces, *Pichia,* such as *P. pastoris* or *P. methanolica, Hansenula,* such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmake™ Yeast Transformation System Kit), and by Reeves et al., *FEMS Microbiology Letters,* 99:193-198 (1992), Manivasakam et al., *Nucleic Acids Research,* 21:4414-4415 (1993) and Ganeva et al., *FEMS Microbiology Letters,* 121: 159-164 (1994).

Examples of suitable insect host cells include, but are not limited to, a *Lepidoptora* cell line, such as *Spodoptera frugiperda* (Sf9 or Sf21) or *Trichoplusia ni* cells (High Five) (See, U.S. Pat. No. 5,077,214). Transformation of insect cells and production of heterologous polypeptides are well known to those skilled in the art.

Examples of suitable mammalian host cells include Chinese hamster ovary (CHO) cell lines, Green Monkey cell lines (COS), mouse cells (for example, NS/O), Baby Hamster Kidney (BHK) cell lines, human cells (such as, human embryonic kidney cells (for example, HEK 293 (A.T.C.C. Accession No. CRL-1573))) and plant cells in tissue culture. Preferably, the mammalian host cells are CHO cell lines and HEK 293 cell lines. Another preferred host cell is the B3.2 cell line (e.g., Abbott Laboratories, Abbott Bioresearch Center, Worcester, Mass.), or another dihydrofolate reductase deficient (DHFR⁻) CHO cell line (e.g., available from Invitrogen Corp., Carlsbad, Calif.). In one aspect, the present disclosure relates to a CHO cell line which produces glycosylated full length human PlGF-1 and at least one linking sequence (namely, one which has the amino acid sequence of SEQ ID NO:2 (which contains a His tag)), wherein the CHO cell line has been deposited with American Type Culture Collection (ATCC) on Jul. 12, 2007 and received ATCC Accession No. PTA-8538. In another aspect, the present disclosure relates to a CHO cell line which produces a glycosylated full length human PlGF-1 and at least one linking sequence (namely, one which has the amino acid sequence of SEQ ID NO:3 (which contains an enterokinase cleavage site)), wherein the CHO cell line has been deposited with the ATCC on Jul. 12, 2007 and received ATCC Accession No. PTA-8537. In still yet a further aspect, the present disclosure relates to a CHO cell line which produces a glycosylated human PlGF-1 fragment (namely, one which has the amino acid sequence of SEQ ID NO:5, wherein the CHO cell line has been deposited with the ATCC on Jul. 12, 2007 and received ATCC Accession No. PTA-8540). In yet another aspect, the present disclosure relates to an isolated, a purified or an isolated and purified human PlGF-1 comprising or consisting of an amino acid sequence selected from the group consisting of SEQ ID NO: 1, SEQ ID NO:2, SEQ ID NO:3 and SEQ ID NO:4. In yet still another aspect, the present disclosure relates to an isolated, a purified or an isolated and purified human PlGF-1 fragment comprising or consisting of an amino acid sequence selected from the group consisting of SEQ ID NO:5, SEQ ID NO:6, SEQ ID NO:7 and SEQ ID NO:8.

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well known in the art and are described, for example by Ausbel et al. (eds.) *Current Protocols in Molecular Biology* John Wiley & Sons, New York, USA (1996). The cultivation of mammalian cells are conducted according to established methods, e.g., as disclosed in Jenkins, Ed., *Animal Cell Biotechnology, Methods and Protocols*, Human Press Inc. Totowa, N.J., USA (1999) and Harrison and Rae *General Techniques of Cell Culture*, Cambridge University Press (1997).

In the production methods, cells are cultivated in a nutrient medium suitable for production of the human PlGF-1 forms of interest using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the glycosylated human PlGF-1 forms of interest to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the glycosylated human PlGF-1 form of interest is secreted into the nutrient medium, the human PlGF-1 form of interest can be recovered directly from the medium. If the human PlGF-1 form of interest is not secreted, it can be recovered from cell lysates.

The resulting human PlGF-1 form of interest may be recovered by methods known in the art. For example, the human PlGF-1 form of interest may be recovered from the nutrient medium by conventional procedures including, but not limited to, centrifugation, filtration, extraction, spray drying, evaporation, or precipitation.

The human PlGF-1 form of interest may be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (See, for example, J-C Janson and Lars Ryden, editors, *Protein Purification*, VCH Publishers, New York (1989)).

The glycosylated human PlGF-1 forms of interest can be optionally deglycosylated using routine techniques in the art. Specifically, the human PlGF-1 or human PlGF-1 fragments can be deglycosylated to remove the N-linked glycosylation (in the case of the full length human PlGF-1 (e.g., SEQ ID NOS:1-4)), one or more O-linked glycosylations (in the case of the human PlGF-1 or human PlGF-1 fragment forms (e.g., SEQ ID NOS:1-8)) or both the N-linked glycosylation and one or more O-linked glycosylations (in the case of human PlGF-1 (e.g., SEQ ID NOS:1-4)). Such N-linked, O-linked or both N-linked and O-linked deglycosylations can be performed using routine techniques known in the art, such as by treating such human PlGF-1 forms with one or more enzymes.

Examples of enzymes that can be used for deglycosylation include PNGase F for N-linked deglycosylation (Asn), and O-Glycanase for removing carbohydrates from O-linked sites (Ser and Thr). Other enzymes also can be used, such as Sialidase, β(1-4)-Galactosidase, and β-N-acetyl-Glucosaminidase, which cleave carbohydrates from special linkages. These enzymes and others are available from, e.g., Prozyme (San Leandro, Calif.) and Sigma-Aldrich (St. Louis, Mo.), and furthermore may be purchased in the form of mixtures or "cocktails." For example, the Sigma-Aldrich E-DE-GLY kit includes a cocktail of PNGase F, α-2(2,6,8,9) Neuraminidase, O-Glycosidase, β(1-4)-Galactosidase, and β-N-acetyl-Glucosaminidase, and the Enzymatic Deglycosylation Kit from Prozyme comprises PNGase F, O-Glycosidase, and Sialidase.

Glycosylated human PlGF-1 forms of interest (namely, a human PlGF-1, a human PlGF-1 fragment, a mutant form of human PlGF-1 or a mutant form of human PlGF-1 fragment) that are deglycosylated using the methods described herein may produce deglycosylated human PlGF-1 forms of interest having at least one amino acid residue converted to or changed to a different amino acid residue as a result of the deglycosylation. If more than one amino acid residue is changed or converted as a result of the deglycosylation, any or all of the resulting changed or converted amino acid residues in the deglycosylated human PlGF-1 form of interest may be changed to the same amino acid residue or to different amino acid residues. For example, a deglycosylated human PlGF-1 form of interest may have at least one asparagine residue converted to or changed to an aspartic acid residue (when compared to its glycosylated form). By way of another example, a deglycosylated human PlGF-1 form of interest may have a first asparagine residue converted to or changed to at least aspartic acid residue and a second asparagine residue converted to or changed to aspartic acid residue (when compared to its glycosylated form). Table A provides some exemplary isolated or purified deglycosylated human PlGF-1 forms of interest that contain at least one amino acid residue that has been changed or converted as a result of deglycosylation.

TABLE A

| Glycosylated Human P/GF-1 Form | Deglycosylated Human P/GF-1 Form | Position of Amino Acid Conversion | Conversion Type | Enzyme used for Deglycosylation |
| --- | --- | --- | --- | --- |
| SEQ ID NO: 1 | SEQ ID NO: 36 | 15 | Asn to Asp | PNGase F |
| SEQ ID NO: 2 | SEQ ID NO: 37 | 21 | Asn to Asp | PNGase F |
| SEQ ID NO: 1 | SEQ ID NO: 38 | 15 and 83 | Asn to Asp (at 15 and 83) | PNGase F |
| SEQ ID NO: 2 | SEQ ID NO: 39 | 21 and 89 | Asn to Asp (at 21 and 89) | PNGase F |
|  | SEQ ID NO: 40 | 21 and 89 | Asn to Asp (at 21); Asn or Asp were detected at 89 | Trypsin |

The glycosylated and deglycosylated human PlGF-1 forms of interest (namely, a human PlGF-1, a human PlGF-1 fragment, a mutant form of human PlGF-1 or a mutant form of human PlGF-1 fragment) can be used for a variety of different purposes and in a variety of different ways. Specifically, the glycosylated and deglycosylated human PlGF-1 forms of interest described herein can be used as one or more calibrators, one or more controls or as a combination of one or more calibrators or controls in an assay, preferably, an immunoassay, for detecting human PlGF-1 in a test sample. Preferably, the glycosylated and deglycosylated full human PlGF-1 comprise or consist of the amino acid sequence of any of SEQ ID NO: 1, SEQ ID NO:2, SEQ ID NO:3, SEQ ID NO:4, SEQ ID NO:36, SEQ ID NO:37, SEQ ID NO:38 or SEQ ID NO:39 and the glycosylated and deglycosylated human PlGF-1 fragments comprise or consist of the amino acid sequence of any of SEQ ID NO:5, SEQ ID NO:6, SEQ ID NO:7 or SEQ ID NO:8.

Furthermore, and as discussed further herein, the human PlGF-1 forms of interest can be employed as immunogen to immunize animals for antibody production, e.g., where the animal can be a mouse, rabbit, chicken, rat, sheep, goat, shark, camel, horse, cat dog, non-human primate, human or other animal. In one embodiment, the immunogen comprises glycosylated or deglycosylated human PlGF-1, especially a glycosylated or deglycosylated human PlGF-1 comprising or consisting of any of the sequences of SEQ ID NO: 1, SEQ ID NO:2, SEQ ID NO:3, SEQ ID NO:4, SEQ ID NO:36, SEQ ID NO:37, SQ ID NO:38 or SEQ ID NO:39 or a glycosylated or deglycosylated human PlGF-1 fragment, especially a glycosylated or deglycosylated human PlGF-1 fragment comprising or consisting of any of the sequences of SEQ ID NO:5-8. In another embodiment, as will be discussed further herein, the human PlGF-1 fragments, including any that may be optionally glycosylated or deglycosylated, can be used as one or calibrators or controls in an immunoassay.

C. Human PlGF-1 Antibodies

The present disclosure provides antibodies that specifically bind to PlGF-1 (e.g., any of SEQ ID NOS: 1-4) or human PlGF-1 fragment (e.g., any of SEQ ID NOS:5-8), which, as described previously herein can be optionally, glycosylated or if glycosylated, optionally, deglycosylated.

In particular, in one aspect, the present disclosure relates to an isolated antibody that specifically binds to human PlGF-1 or human PlGF-1 fragment, wherein the antibody has a variable heavy domain region comprising an amino acid sequence of SEQ ID NO:32.

In another aspect, the present disclosure relates to an isolated antibody that specifically binds to human PlGF-1 or human PlGF-1 fragment, wherein the antibody has a variable light domain region comprising an amino acid sequence of SEQ ID NO:29.

In another aspect, the present disclosure relates to an isolated antibody that specifically binds to human PlGF-1 or human PlGF-1 fragment, wherein the antibody has a variable heavy domain region comprising an amino acid sequence of SEQ ID NO:32 and a variable light domain region comprising an amino acid sequence of SEQ ID NO:29.

In yet another aspect, the present disclosure relates to murine hybridoma cell line 1-255-713 having ATCC Accession No. PTA-8536, deposited on Jul. 12, 2007. In yet another aspect, the present disclosure relates to an antibody produced by murine hybridoma cell line 1-255-713 having ATCC Accession No. PTA-8536, deposited on Jul. 12, 2007. Murine hybridoma cell line 1-255-713 has a variable heavy domain comprising the amino acid sequence of SEQ ID NO:32 and a variable light domain comprising the amino acid sequence of SEQ ID NO:29.

In yet still another aspect, the present invention relates to murine hybridoma cell line 1-255-2675. Murine hybridoma cell line 1-255-2675 is a subclone of murine hybridoma cell line 1-255-713. Murine hybridoma cell line 1-255-2675 produces an antibody that is identical to the antibody produced by hybridoma cell line 1-255-713. Murine hybridoma cell line 1-255-2675 has a variable heavy domain comprising the amino acid sequence of SEQ ID NO:32 and a variable light domain comprising the amino acid sequence of SEQ ID NO:29.

In yet another aspect, the present disclosure relates to an isolated antibody that specifically binds to human PlGF-1 or human PlGF-1 fragment, wherein the antibody has a variable heavy domain region comprising an amino acid sequence of SEQ ID NO:35.

In yet another aspect, the present disclosure relates to an isolated antibody that specifically binds to human PlGF-1 or human PlGF-1 fragment, wherein the antibody has a variable light domain region comprising an amino acid sequence of SEQ ID NO:43.

In another aspect, the present disclosure relates to an isolated antibody that specifically binds to human PlGF-1 or human PlGF-1 fragment, wherein the antibody has a variable heavy domain region comprising an amino acid sequence of SEQ ID NO:35 and a variable light domain region comprising an amino acid sequence of SEQ ID NO:43.

In yet another aspect, the present disclosure relates to murine hybridoma cell line 2-826-335 having ATCC Accession No. PTA-8539, deposited on Jul. 12, 2007. In yet another aspect, the present disclosure relates to an antibody produced by murine hybridoma cell line 2-826-335 having ATCC Accession No. PTA-8539, deposited on Jul. 12, 2007. Murine hybridoma cell line 2-826-335 has a variable heavy domain comprising the amino acid sequence of SEQ ID NO:35 and a variable light domain comprising the amino acid sequence of SEQ ID NO:43.

D. Methods of Making and Using PlGF-1 Antibodies

The antibodies of the present disclosure can be made using a variety of different techniques known in the art. For example, polyclonal and monoclonal antibodies against human PlGF-1 or human PlGF-1 fragment can be raised by immunizing a suitable subject (such as, but not limited to, a rabbit, goat, mouse or other mammal) with an immunogenic preparation which contains a suitable immunogen. The immunogen that can be used for the immunization can include cells such as cells from immortalized cell lines NSO which is known to express human PlGF-1 or human PlGF-1 fragment.

Alternatively, the immunogen can be the purified or isolated human PlGF-1 protein itself (namely, any of SEQ ID NOS:1-4) or a human PlGF-1 fragment thereof (namely, any of SEQ ID NOS:5-8). For example, human PlGF-1 (See, SEQ ID NOS:1-4) that has been isolated from a cell which produces the protein (such as NSO) using affinity chromatography, immunoprecipitation or other techniques which are well known in the art, can be used as an immunogen. Alternatively, immunogen can be prepared using chemical synthesis using routine techniques known in the art (such as, but not limited to, a synthesizer).

The antibodies raised in the subject can then be screened to determine if the antibodies bind to human PlGF-1 or human PlGF-1 fragment. Such antibodies can be further screened using the methods described herein (See, e.g., Example 1). Suitable methods to identify an antibody with the desired characteristics are described herein (See, Example, 1). Moreover, it is fully anticipated that results obtained with antibodies that bind to human PlGF-1 fragment (See, SEQ ID NOS: 5-8) are fully translatable to binding of human PlGF-1, and that antibodies will bind to comparable residues of human PlGF-1 (See, SEQ ID NOS: 1-4). Accordingly, for convenience, and unless there lacks a rational basis in a particular instance for not doing so, human PlGF-1 fragment can be employed to assess binding properties of antibodies.

The unit dose of immunogen (namely, the purified protein, tumor cell expressing the protein, or recombinantly expressed human PlGF-1 or human PlGF-1 fragment) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen, namely, human PlGF-1 (e.g., SEQ ID NOS: 1-4), or a human PlGF-1 fragment thereof (e.g., SEQ ID NOS:5-8) as described herein.

Other methods of raising antibodies against human PlGF-1 (e.g., SEQ ID NOS: 1-4), or a human PlGF-1 fragment thereof (e.g., SEQ ID NOS:5-8) include using transgenic mice which express human immunoglobin genes (See, for example, PCT International Applications WO 91/00906, WO 91/10741 or WO 92/03918). Alternatively, human monoclonal antibodies can be produced by introducing an antigen into immune deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (See, for example, PCT International Application WO 93/05796, U.S. Pat. No. 5,411,749; or McCune et al., *Science,* 241:1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody producing cells can be harvested from an immunized animal and used to prepare monoclonal antibodies using standard techniques. For example, the antibody producing cells can be fused by standard somatic cell fusion procedures with immortalizing cells such as myeloma cells to yield hybridoma cells. Such techniques are well known in the art, and include, for example, the hybridoma technique as originally developed by Kohler and Milstein, *Nature,* 256:495497 (1975)), the human B cell hybridoma technique (Kozbar et al., *Immunology Today,* 4:72 (1983)), and the EBV-hybridoma technique to produce human monoclonal antibodies (Cole et al., *Monoclonal Antibodies and Cancer Therapy,* Alan R. Liss, Inc. pp. 77-96 (1985)). The technology for producing monoclonal antibody hybridomas is well known to those skilled in the art.

Monoclonal antibodies can also be made by harvesting antibody producing cells, for example, splenocytes, from transgenic mice expressing human immunoglobulin genes and which have been immunized with the human PlGF-1 protein. The splenocytes can be immortalized through fusion with human myelomas or through transformation with Epstein-Barr virus (EBV). These hybridomas can be made using human B cell- or EBV-hybridoma techniques described in the art (See, for example, Boyle et al., European Patent Publication No. 0 614 984).

Hybridoma cells producing a monoclonal antibody which specifically binds to the human PlGF-1 (e.g., SEQ ID NOS: 1-4) or a human PlGF-1 fragment thereof (e.g., SEQ ID NOS:5-8) are detected by screening the hybridoma culture supernatants by, for example, screening to select antibodies that specifically bind to the immobilized human PlGF-1 or human PlGF-1 fragment, or by testing the antibodies as described herein to determine if the antibodies have the desired characteristics, namely, the ability to bind to human PlGF-1 or human PlGF-1 fragment. After hybridoma cells are identified that produce antibodies of the desired specificity, the clones may be subcloned, e.g., by limiting dilution procedures, for example the procedure described by Wands et al. (*Gastroenterology* 80:225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in *Monoclonal Antibodies: A New Dimension In Biological Analyses*, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the human PlGF-1 or human PlGF-1 fragment. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen Corp., Carlsbad, Calif.). Briefly, the antibody library is screened to identify and isolate phages or yeast cells that express an antibody that specifically binds to human PlGF-1 (e.g., SEQ ID NOS: 1-4) or human PlGF-1 fragment (SEQ ID NOS:5-8). Preferably, the primary screening of the library involves screening with an immobilized human PlGF-1 or human PlGF-1 fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen Corporation, Carlsbad, Calif.)) by well known recombinant DNA techniques. The polynucleotide can be further manipulated (for example, linked to nucleic acid encoding additional immunoglobulin domains, such as additional constant regions) and/or expressed in a host cell.

Alternatively, recombinant forms of antibodies, such as chimeric and humanized antibodies, can also be prepared to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, namely, antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (See, for example, PCT Patent Publication PCT/US86/02269, European Patent Application 184,187 or European Patent Application 171,496).

A chimeric antibody can be further "humanized" by replacing portions of the variable region not involved in antigen binding with equivalent portions from human variable regions. General reviews of "humanized" chimeric antibodies can be found in Morrison, S. L., *Science*, 229:1202-1207 (1985) and in Oi et al., *BioTechniques*, 4-214 (1986). Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by complementarity determining region (CDR) substitution (See, for example, U.S. Pat. No. 5,225,539; Jones et al., *Nature,* 321:552-525 (1986); Verhoeyan et al., *Science* 239:1.534 (1988); and Beidler et al., *J. Immunol,* 141:4053-4060 (1988)).

Epitope imprinting can also be used to produce a "human" antibody polypeptide dimer that retains the binding specificity of the antibodies (e.g., hamster antibodies) specific for the human PlGF-1 (e.g., SEQ ID NOS: 1-4) or human PlGF-1 fragment (e.g., SEQ ID NOS:5-8). Briefly, a gene encoding a non-human variable region (VH) with specific binding to an antigen and a human constant region (CHI), is expressed in *E. coli* and infected with a phage library of human Vλ.Cλ genes. Phage displaying antibody fragments are then screened for binding to the human PlGF-1 protein. Selected human Vλ genes are recloned for expression of Vλ.Cλ. chains and *E. coli* harboring these chains are infected with a phage library of human VHCH1 genes and the library is subject to rounds of screening with antigen coated tubes (See, WO 93/06213).

In another aspect, the present disclosure contemplates that the antibody is an antibody fragment. For example, the antibody fragment can include, but is not limited to, a Fab, a Fab', a Fab'-SH fragment, a di-sulfide linked Fv, a single chain Fv (scFv) and a F(ab')$_2$ fragment. Various techniques are known to those skilled in the art for the production of antibody fragments. For example, such fragments can be derived via proteolytic digestion of intact antibodies (See, for example, Morimoto et al., *J. Biochem. Biophys. Methods,* 24:107-117 (1992) and Brennan et al., *Science,* 229:81 (1985)) or produced directly by recombinant host cells. For example, Fab'-SH fragments can be directly recovered from *E. coli* and chemically coupled to form F(ab')$_2$ fragments (See, Carter et al., *Bio/Technology,* 10:163-167 (1992)). In another embodiment, the F(ab')$_2$ is formed using the leucine zipper GCN4 to promote assembly of the F(ab')$_2$ molecule. Alternatively, Fv, Fab or F(ab')$_2$ fragments can be isolated directly from recombinant host cell culture. Single chain variable region fragments (scFv) are made by linking light and/or heavy chain variable regions by using a short linking peptide or sequence (See, Bird et al. *Science,* 242:423-426 (1998)). An example of a linking sequence is GPAKELTPLKEAKVS (SEQ ID NO: 19).

The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art. Moreover, other forms of single chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (See, for example, Holliger, P., et al., *Proc. Natl. Acad. Sci. USA,* 90:6444-6448 (1993); Poljak, R. J., et al., *Structure,* 2:1121-1123 (1994)).

Furthermore, in some aspects of the invention(s) as described herein (e.g., use as controls), it may be possible to employ commercially available anti-PlGF-1 antibodies, or anti-PlGF-1 antibodies or their methods for production described in the literature. These include but are not limited to: (1) monoclonal antibody 264 (also referred to as "MAB264"), which is an unconjugated, mouse anti-human PlGF-1 monoclonal antibody from Clone 37203 which is commercially available from R&D Systems, Inc., Minneapolis, Minn. (Catalog Number MAB264); (2) polyclonal antibody pB264 (also referred to as "pB264", "AF-264-PB", "PAB264" or AB-264-PB as used interchangeably herein), which is an unconjugated, goat anti-human PlGF-1 polyclonal antibody that is available from R&D Systems, Inc., Minneapolis, Minn. (Catalog Number AF-264-PB); and/or (3) rat monoclonal antibody 04 (also known as Rat anti-Human PlGF clone number 358932, which was obtained as a pre-release reagent from R&D Systems, Inc., Minneapolis, Minn.).

The antibodies of the present disclosure have a variety of uses. In one aspect, the antibodies of the present disclosure can be used as one or more immunodiagnostic reagents. For example, the antibodies of the present disclosure can be used as one or more immunodiagnostic reagents in one or more methods for detecting the presence of human PlGF-1 or human PlGF-1 fragment in a test sample. More specifically, the antibodies of the present disclosure can be used as one or more capture antibodies, one or more conjugate antibodies or as both one or more capture antibodies and one or more conjugate antibodies in immunoassays to detect the presence of human PlGF-1 or human PlGF-1 fragment in a test sample in a test sample.

E. Sample Collection And Pretreatment

Methods well known in the art for collecting, handling and processing urine, blood, serum and plasma, and other body fluids, are used in the practice of the present disclosure, for instance, when the antibodies according to the invention are employed as immunodiagnostic reagents, and/or in an PlGF-1 immunoassay kit.

The test sample may comprise further moieties in addition to the PlGF-1 analyte of interest such as antibodies, antigens, haptens, hormones, drugs, enzymes, receptors, proteins, peptides, polypeptides, oligonucleotides or polynucleotides. For example, the sample may be a whole blood sample obtained from a subject. It may be necessary or desired that a test sample, particularly whole blood, be treated prior to immunoassay as described herein, e.g., with a pretreatment reagent. Even in cases where pretreatment is not necessary (e.g., most urine samples), pretreatment optionally may be done for mere convenience (e.g., as part of a regimen on a commercial platform). The pretreatment reagent can be a heterogeneous agent or a homogeneous agent.

With use of a heterogenous pretreatment reagent according to the invention, the pretreatment reagent precipitates analyte binding protein (e.g., protein capable of binding human PlGF-1 or human PlGF-1 fragment) present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with the capture antibody in the antibody capture step. The pretreatment reagent employed for such an assay typically is diluted in the pretreated test sample mixture, either before the antibody capture step or during encounter with the antibody in the antibody capture step. Despite such dilution, a certain amount of the pretreatment reagent (for example, 5 M methanol and/or 0.6 M ethylene glycol) is still present (or remains) in the test sample mixture during antibody capture.

The pretreatment reagent can be any reagent appropriate for use with the immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, *Clin. Chem.,* 36:1969-1973 (1990) and Wallemacq et al., Evaluation of the New AxSYM Cyclosporine Assay:Comparison with TDx Monoclonal Whole Blood and EMIT Cyclosporine Assays, *Clin. Chem.* 45: 432-435 (1999)), and/or as commercially available. Additionally, pretreatment can be done as described in Abbott's U.S. Pat. No. 5,135,875, EP Patent Publication No. 0 471 293, U.S. Patent Application 60/878,017 filed Dec. 29, 2006; and U.S. Patent Application No. US 2008-0020401 (incorporated by reference in its entirety for its teachings regarding pretreatment).

F. Human PlGF-1 or Human PlGF-1 Fragment Immunoassays

The present disclosure also relates to immunoassays. Specifically, in one aspect, the present disclosure relates to improved immunoassays for the detection of human PlGF-1 or human PlGF-1 fragment which employ the human PlGF-1 or human PlGF-1 fragments described herein in Section B. In another aspect, the present disclosure relates to immunoassays that employ the antibodies described herein in Section C.

The immunoassays of the present disclosure can be conducted using any format known in the art, such as, but not limited to, a sandwich format. For example, at least two antibodies can be employed to separate and quantify human PlGF-1 or human PlGF-1 fragment in a test sample in a test sample. Specifically, the at least two antibodies bind to certain epitopes of human PlGF-1 or human PlGF-1 fragment forming an immune complex which is referred to as a "sandwich". Generally, in the immunoassays one or more antibodies can be used to capture the human PlGF-1 or human PlGF-1 fragment in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody", "detection antibodies", a "conjugate" or "conjugates"). The immunoassays of the present disclosure can be conducted to evaluate whether or not a subject is suffering from cardiovascular disease, sickle cell disease, chronic obstructive pulmonary disease, age-related macular degeneration, peripheral vascular occlusive disease, inflammation, preeclampsia, psoriasis, Crohn's disease, endometriosis, rheumatoid arthritis or any combinations thereof.

In mentioned briefly above, in one aspect, the present disclosure relates to an improvement of an immunoassay for the detection of human PlGF-1 or human PlGF-1 fragment which employs the human PlGF-1 or human PlGF-1 fragments described herein in Section B. This particular method as described herein can be employed in any human PlGF-1 or human PlGF-1 fragment immunoassay, with use of any antibodies for capture and/or detection. In one embodiment, the present disclosure thus provides, an improvement of a method for detecting the presence of human PlGF-1 or human PlGF-1 fragment in a test sample, the method comprising:

(a) contacting a test sample suspected of human PlGF-1 or human PlGF-1 fragment with at least one antibody specific for said human PlGF-1 or human PlGF-1 fragment for a time and under conditions that allow the formation of a human PlGF-1 or human PlGF-1 fragment/antibody complex; and (b) detecting any human PlGF-1 or human PlGF-1 fragment/antibody complex formed as indicating the presence of said human PlGF-1 or human PlGF-1 fragment;

wherein the improvement comprises employing as a calibrator or control a calibrator or control which is a human PlGF-1 or human PlGF-1 fragment as described herein in Section B (e.g., which may optionally be a glycosylated human PlGF-1, a glycosylated human PlGF-1 fragment, a deglycosylated human PlGF-1 or deglycosylated human PlGF-1 fragment)

Generally speaking, a test sample being tested for (for example, suspected of containing) human PlGF-1 or human PlGF-1 fragment can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing human PlGF-1 or human PlGF-1 fragment is first brought into contact with an at least one first capture antibody under conditions which allow the formation of a first antibody/human PlGF-1 or human PlGF-1 fragment complex. If more than one capture antibody is used, a first multiple capture antibody/human PlGF-1 or human PlGF-1 fragment complex is formed. In a sandwich assay, the antibodies, preferably, the at least one capture antibody, are used in molar excess amounts of the maximum amount of human PlGF-1 or human PlGF-1 fragment expected in the test sample. For example, from about 5 μg/mL to about 1 mg/mL of antibody per mL of buffer (e.g., microparticle coating buffer) can be used.

Optionally, prior to contacting the test sample with the at least one capture antibody (for example, the first capture antibody), the at least one capture antibody can be bound to a solid support which facilitates the separation the first antibody/human PlGF-1 or human PlGF-1 fragment complex from the test sample. Any solid support known in the art can be used, including, but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind human PlGF-1 or human PlGF-1 fragment. Alternatively, the antibody (or antibodies) can be bound with microparticles that have previously coated with streptavidin or biotin (for example, using Power-Bind™—SA-MP streptavidin coated microparticles, available from Seradyn, Indianapolis, Ind.). Alternatively, the antibody (or antibodies) can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl) carbodiimide.

After the test sample being tested for and/or suspected of containing human PlGF-1 or human PlGF-1 fragment is brought into contact with the at least one capture antibody (for example, the first capture antibody), the mixture is incubated in order to allow for the formation of a first antibody (or multiple antibody)-human PlGF-1 or human PlGF-1 fragment complex. The incubation can be carried out at a pH of from about 4.5 to about 10.0, at a temperature of from about 2° C. to about 45° C., and for a period from at least about one (1) minute to about eighteen (18) hours, preferably from about 1 to about 20 minutes, most preferably for about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/human PlGF-1 or human PlGF-1 fragment complex, the complex is then contacted with at least one detection antibody (under conditions which allow for the formation of a (first or multiple) capture antibody/human PlGF-1 or human PlGF-1 fragment/second antibody detection complex). The at least one detection antibody can be the second, third, fourth, etc. antibodies used in the immunoassay. If the capture antibody/human PlGF-1 or human PlGF-1 fragment complex is contacted with more than one detection antibody, then a (first or multiple) capture antibody/human PlGF-1 or human PlGF-1 fragment/(multiple) detection antibody complex is formed. As with the capture antibody (e.g., the first capture antibody), when the at least second (and subsequent) detection antibody is brought into contact with the capture antibody/human PlGF-1 or human PlGF-1 fragment complex, a period of incubation under conditions similar to those described above is required for the formation of the (first or multiple) capture antibody/human PlGF-1 or human PlGF-1 fragment/(second or multiple) detection antibody complex. Preferably, at least one detection antibody contains a detectable label. The detectable label can be bound to the at least one detection antibody (e.g., the second detection antibody) prior to, simultaneously with or after the formation of the (first or multiple) capture antibody/human PlGF-1 or human PlGF-1 fragment/(second or multiple) detection antibody complex. Any detectable label known in the art can be used. For example, the detectable label can be a radioactive label, such as, $^{3}$H, $^{125}$I, $^{35}$S, $^{14}$C, $^{32}$P, $^{33}$P, an enzymatic label, such as horseradish peroxidase, alkaline phosphatase, glucose 6-phosphate dehydrogenase, etc., a chemiluminescent label, such as, acridinium esters (e.g., acridium esters, acridinium SPSP (N10-(3-sulfopropyl)-N-(3-sulfopropyl, etc.), luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The (first or multiple) capture antibody/human human PlGF-1 or human PlGF-1 fragment/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support it can be simultaneously contacted with the human PlGF-1 or human PlGF-1 fragment-containing sample and the at least one second detection antibody to form a first (multiple) antibody/human PlGF-1 or human PlGF-1 fragment/second (multiple) antibody complex, followed by removal of the fluid (test sample) from contact with the solid support. If the at least one first capture antibody is not bound to a solid support, then the (first or multiple) capture antibody/human PlGF-1 or human PlGF-1 fragment/(second or multiple) detection antibody complex does not have to be removed from the test sample for quantification of the amount of the label.

After formation of the labeled capture antibody/human PlGF-1 or human PlGF-1 fragment/detection antibody complex (e.g., the first capture antibody/human PlGF-1 or human PlGF-1 fragment/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of human PlGF-1 or human PlGF-1 fragment in the test sample is determined by use of a standard curve that has been generated using serial dilutions of human PlGF-1 or human PlGF-1 fragment of known concentration. Other than using serial dilutions of human PlGF-1 or human PlGF-1 fragment, the standard curve can be generated gravimetrically, by mass spectroscopy and by other techniques known in the art.

In another aspect, the antibodies described in Section C herein can be employed as an immunodiagnostic agents, e.g., in methods for detecting the presence of human PlGF-1 or human PlGF-1 fragment in a test sample suspected of containing human PlGF-1 or human PlGF-1 fragment. The method comprises the steps of:

(a) contacting a test sample suspected of containing human PlGF-1 or human PlGF-1 fragment with the immunodiagnostic reagent as described herein for a time and under conditions that allow formation of a human PlGF-1 or human PlGF-1 fragment/antibody complex; and (b) detecting any human PlGF-1 or human PlGF-1 fragment/antibody complex formed as indicating the presence of antigen, namely, human PlGF-1 or human PlGF-1 fragment.

In one embodiment, the immunodiagnostic reagent comprises one or more antibodies selected from the group consisting of:

(a) an isolated antibody that specifically binds to human PlGF-1 or human PlGF-1 fragment, wherein said antibody has a variable heavy domain region comprising the amino acid sequence of SEQ ID NO:32;

(b) an isolated antibody that specifically bind to human PlGF-1 or human PlGF-1 fragment, wherein said antibody has a variable light domain region comprising the amino acid sequence of SEQ ID NO:29;

(c) an isolated antibody that specifically binds to human PlGF-1 or human PlGF-1 fragment, wherein said antibody has a variable heavy domain region comprising the amino acid sequence of SEQ ID NO:32 and a variable light domain region comprising the amino acid sequence of SEQ ID NO:29;

(d) an antibody produced by murine hybridoma cell line 1-255-713 having ATCC Accession No. PTA-8536;

(e) an isolated antibody that specifically binds to human PlGF-1 or human PlGF-1 fragment, wherein said antibody has a variable heavy domain region comprising the amino acid sequence of SEQ ID NO:35;

(f) an isolated antibody that specifically bind to human PlGF-1 or human PlGF-1 fragment, wherein said antibody has a variable light domain region comprising the amino acid sequence of SEQ ID NO:43;

(g) an isolated antibody that specifically binds to human PlGF-1 or human PlGF-1 fragment, wherein said antibody has a variable heavy domain region comprising the amino acid sequence of SEQ ID NO:35 and a variable light domain region comprising the amino acid sequence of SEQ ID NO:43; and (h) an antibody produced by murine hybridoma cell line 2-826-335 having ATCC Accession No. PTA-8539.

Excellent immunoassays, particularly, sandwich assays, can be performed using the antibodies of the present disclosure (e.g., namely those described in Section C) as the capture antibodies, detection antibodies or as capture and detection antibodies. For example, at least one of the capture antibodies, at least one of the detection antibodies or both the capture antibody or detection antibody can be an antibody produced by murine hybridoma cell line 1-255-713 having ATCC Accession No. PTA-8536 or murine hybridoma cell line 2-826-335 having ATCC Accession No. PTA-8539.

In still a further aspect, the human PlGF-1 assay employs a monoclonal antibody sandwich that utilizes a capture antibody that binds only free human PlGF-1 and excludes human PlGF-1 bound to sFlt-1. The amount of captured free human PlGF-1 is detected with an acridinylated anti-human PlGF-1 monoclonal antibody. The monoclonal antibody produced by murine hybridoma cell line 2-826-335 having ATCC Accession No. PTA-8539 and deposited on Jul. 12, 2007 can be employed as a capture antibody that binds only free human PlGF-1 and excludes human PlGF-1 bound to sFlt-1. Optionally, the detection antibody that can be used is an antibody produced by murine hybridoma cell line 1-255-713 having ATCC Accession No. PTA-8536.

The test sample being tested for (for example, suspected of containing) human PlGF-1 or human PlGF-1 fragment can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing human PlGF-1 or human PlGF-1 fragment is first brought into contact with an at least one first capture antibody under conditions which allow the formation of a first antibody/human PlGF-1 or human PlGF-1 fragment complex. If more than one capture antibody is used, a first multiple capture antibody/human PlGF-1 or human PlGF-1 fragment complex is formed. In a sandwich assay, the antibodies, preferably, the at least one capture antibody, are used in molar excess amounts of the maximum amount of human PlGF-1 or human PlGF-1 fragment expected in the test sample. For example, from about 5 µg/mL to about 1 mg/mL of antibody per mL of buffer (e.g., microparticle coating buffer) can be used. Examples of other antibodies that can be used as capture antibodies include, but are not limited to: (1) monoclonal antibody 264; (2) polyclonal antibody pB264; and/or (3) rat monoclonal antibody 04.

Optionally, prior to contacting the test sample with the at least one capture antibody (for example, the first capture antibody), the at least one capture antibody can be bound to a solid support which facilitates the separation the first antibody/human PlGF-1 or human PlGF-1 fragment complex from the test sample. Any solid support known in the art can be used, including, but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind human PlGF-1 or human PlGF-1 fragment. Alternatively, the antibody (or antibodies) can be bound with microparticles that have previously coated with streptavidin or biotin (for example, using Power-Bind™—SA-MP streptavidin coated microparticles, available from Seradyn, Indianapolis, Ind.). Alternatively, the antibody (or antibodies) can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl) carbodiimide.

After the test sample being tested for and/or suspected of containing human PlGF-1 or human PlGF-1 fragment is brought into contact with the at least one capture antibody (for example, the first capture antibody), the mixture is incubated in order to allow for the formation of a first antibody (or multiple antibody)-human PlGF-1 or human PlGF-1 fragment complex. The incubation can be carried out at a pH of from about 4.5 to about 10.0, at a temperature of from about 2° C. to about 45° C., and for a period from at least about one (1) minute to about eighteen (18) hours, preferably from about 1 to about 20 minutes, most preferably for about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/human PlGF-1 or human PlGF-1 fragment complex, the complex is then contacted with at least one detection antibody (under conditions which allow for the formation of a (first or multiple) capture antibody/human PlGF-1 or human PlGF-1 fragment/second antibody detection complex). The at least one detection antibody can be the second, third, fourth, etc. antibodies used in the immunoassay. If the capture antibody/human PlGF-1 or human PlGF-1 fragment complex is contacted with more than one detection antibody, then a (first or multiple) capture antibody/human PlGF-1 or human PlGF-1 fragment/(multiple) detection antibody complex is formed. Examples of other antibodies that can be used as detection antibodies include, but are not limited to: (1) monoclonal antibody 264; (2) polyclonal antibody pB264; and/or (2) rat monoclonal antibody 04.

As with the capture antibody (e.g., the first capture antibody), when the at least second (and subsequent) detection antibody is brought into contact with the capture antibody/human PlGF-1 or human PlGF-1 fragment complex, a period of incubation under conditions similar to those described above is required for the formation of the (first or multiple) capture antibody/human PlGF-1 or human PlGF-1 fragment/(second or multiple) detection antibody complex. Preferably, at least one detection antibody contains a detectable label. The detectable label can be bound to the at least one detection antibody (e.g., the second detection antibody) prior to, simultaneously with or after the formation of the (first or multiple) capture antibody/human PlGF-1 or human PlGF-1 fragment/(second or multiple) detection antibody complex. Any detectable label known in the art can be used. For example, the detectable label can be a radioactive label, such as, $^3$H, $^{125}$I, $^{35}$S, $^{14}$C, $^{32}$P, $^{33}$P, an enzymatic label, such as horseradish peroxidase, alkaline phosphatase, glucose 6-phosphate dehydrogenase, etc., a chemiluminescent label, such as, acridinium esters, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The (first or multiple) capture antibody/human PlGF-1 or human PlGF-1 fragment/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support it can be simultaneously contacted with the human PlGF-1 or human PlGF-1 fragment-containing sample and the at least one second detection antibody to form a first (multiple) antibody/human PlGF-1 or human PlGF-1 fragment/second (multiple) antibody complex, followed by removal of the fluid (test sample) from contact with the solid support. If the at least one first capture antibody is not bound to a solid support, then the (first or multiple) capture antibody/human PlGF-1 or human PlGF-1 fragment/ (second or multiple) detection antibody complex does not have to be removed from the test sample for quantification of the amount of the label.

After formation of the labeled capture antibody/human PlGF-1 or human PlGF-1 fragment/detection antibody complex (e.g., the first capture antibody/human PlGF-1 or human PlGF-1 fragment/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of human PlGF-1 or human PlGF-1 fragment in the test sample is determined by use of a standard curve that has been generated using serial dilutions of human human PlGF-1 or human PlGF-1 fragment of known concentration. Other than using serial dilutions of human PlGF-1 or human PlGF-1 fragment, the standard curve can be generated gravimetrically, by mass spectroscopy and by other techniques known in the art.

The test sample being tested to determine the amount of human PlGF-1 or human PlGF-1 fragment can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

It goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® Human PlGF-1 conjugate diluent (Abbott Laboratories, Abbott Park, Ill.) containing 2-(N-morpholino) ethanesulfonic acid (MES), other salt, protein blockers, antimicrobial and detergent. An exemplary calibrator diluent is ARCHITECT® Human PlGF-1 calibrator diluent (Abbott Laboratories, Abbott Park, Ill.), which comprises a buffer containing MES, other salt, a protein blocker and an antimicrobial.

Furthermore, as previously mentioned, the methods and kits optionally are adapted for use on an automated or semi-automated system. Some of the differences between an automated or semi-automated system as compared to a non-automated system (e.g., ELISA) include the substrate to which the capture antibody is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent (Pb264) for a relatively longer incubation time (e.g., about 2 hours), an automated or semi-automated format (e.g., ARCHITECT®) may have a relatively shorter incubation time (e.g., approximately 4 minutes for the ARCHITECT®).

Various parameters can be used to quantify and compare an automated or semi-automated assay (e.g., Abbott ARCHITECT® assay as described herein in the Examples) as compared to a non-automated assay (e.g., ELISA). In one aspect, however, an automated or semi-automated assay as encompassed herein can be considered "better" than an non-automated assay (e.g., ELISA) in that the automated or semi-automated assay is more sensitive or potentially more specific in terms of detecting free PlGF. This is corroborated by the fact that the automated or semi-automated assay shows greater inhibition or sensitivity to sFlt-1 and therefore it is more likely to detect free PlGF.

G. Human PlGF-1 Immunoassay Kits

The present disclosure also contemplates diagnostic kits for detecting the presence of antigen, namely, human PlGF-1 or human PlGF-1 fragment in a test sample. In one aspect, such kits can comprise one or more of the immunodiagnostic reagents (e.g., antibodies) described previously herein in Section C. More specifically, if the kit is a kit for performing an immunoassay, the kit optionally can comprise the immunodiagnostic reagent described herein and instructions. In another aspect, such kits comprise at least one calibrator or control as described previously herein in Section B. In still yet another aspect, such kits comprise one or more of the immunodiagnostic reagents (e.g., antibodies) described previously herein in Section C and at least one calibrator or control as described previously herein in Section B. Moreover and optionally, each of these kits can be optimized for use on commercial platforms or employed in a variety of other formats (e.g., on electrochemical or other hand-held or point-of-care assay systems).

In one aspect, the present disclosure further provides for diagnostic and quality control kits comprising one or more of the antibodies described herein in Section C.

For example, such kits can contain at least one of:

(a) an isolated antibody that specifically binds to human PlGF-1 or human PlGF-1 fragment, wherein said antibody has a variable heavy domain region comprising the amino acid sequence of SEQ ID NO:32;

(b) an isolated antibody that specifically bind to human PlGF-1 or human PlGF-1 fragment, wherein said antibody has a variable light domain region comprising the amino acid sequence of SEQ ID NO:29;

(c) an isolated antibody that specifically binds to human PlGF-1 or human PlGF-1 fragment, wherein said antibody has a variable heavy domain region comprising the amino acid sequence of SEQ ID NO:32 and a variable light domain region comprising the amino acid sequence of SEQ ID NO:29;

(d) an antibody produced by murine hybridoma cell line 1-255-713 having ATCC Accession No. PTA-8536;

(e) an isolated antibody that specifically binds to human PlGF-1 or human PlGF-1 fragment, wherein said antibody has a variable heavy domain region comprising the amino acid sequence of SEQ ID NO:35;

(f) an isolated antibody that specifically bind to human PlGF-1 or human PlGF-1 fragment, wherein said antibody has a variable light domain region comprising the amino acid sequence of SEQ ID NO:43;

(g) an isolated antibody that specifically binds to human PlGF-1 or human PlGF-1 fragment, wherein said antibody has a variable heavy domain region comprising the amino acid sequence of SEQ ID NO:35 and a variable light domain region comprising the amino acid sequence of SEQ ID NO:43;

(h) an antibody produced by murine hybridoma cell line 2-826-335 having ATCC Accession No. PTA-8539; and (i) combinations of any of (a)-(h).

Optionally these kits can include quality control reagents (e.g., sensitivity panels, calibrators, and positive controls). The calibrator or control can be at least one calibrator or control as described previously herein in Section B (namely, a glycosylated human PlGF-1, a glycosylated human PlGF-1 fragment, a deglycosylated human PlGF-1 or a deglycosylated human PlGF-1 fragment having the amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, and combinations of SEQ ID NOS:1, 2, 3, 4, 5, 6, 7 or 8). Preparation of quality control reagents is well known in the art, and is described, e.g., on a variety of immunodiagnostic product insert sheets. PlGF-1 sensitivity panel members optionally can be prepared in varying amounts containing, e.g., known quantities of PlGF-1 antibody ranging from "low" to "high", e.g., by spiking known quantities of the PlGF-1 antibodies according to the invention into an appropriate assay buffer (e.g., a phosphate buffer). These sensitivity panel members optionally are used to establish assay performance characteristics, and further optionally are useful indicators of the integrity of the immunoassay kit reagents, and the standardization of assays.

In another embodiment, the present disclosure provides for quality control kits comprising one or more antibodies of the present disclosure (e.g, namely, described herein in Section C) for use as a sensitivity panel to evaluate assay performance characteristics and/or to quantitate and monitor the integrity of the antigen(s) used in the assay.

The antibodies provided in these kits can incorporate a detectable label, such as a fluorophore, radioactive moiety, enzyme, biotin/avidin label, chromophore, chemiluminescent label, or the like, or the kit may include reagents for labeling the antibodies or reagents for detecting the antibodies (e.g., detection antibodies) and/or for labeling the antigens or reagents for detecting the antigen. The antibodies, calibrators and/or controls can be provided in separate containers or pre-dispensed into an appropriate assay format, for example, into microtiter plates.

In another aspect, the present disclosure relates to kits for performing an immunoassay that contains at least one calibrator or control as described previously herein in Section B. Preferably, however, for immunoassay kits as described herein, the calibrator or control is a human PlGF-1 or human PlGF-1 fragment, especially a glycosylated human PlGF-1 or a glycosylated human PlGF-1 fragment, a deglycosylated human PlGF-1 or a deglycosylated human PlGF-1 fragment.

Accordingly, these kits can comprise at least one calibrator, or at least one control, or a combination of at least one calibrator and at least one control, wherein the calibrator or control comprises a glycosylated human PlGF-1, a glycosylated human PlGF-1 fragment, a deglycosylated human PlGF-1 or a deglycosylated human PlGF-1 fragment of the present disclosure. Preferably, the at least one calibrator or at least one control is a glycosylated human PlGF-1, a glycosylated human PlGF-1 fragment, a deglycosylated human PlGF-1 or a deglycosylated human PlGF-1 fragment having the amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, and combinations of SEQ ID NOS: 1, 2, 3, 4, 5, 6, 7 or 8. If the kit is a kit for performing an immunoassay, then the kit optionally further comprises: (1) at least one capture antibody that specifically binds to a human PlGF-1 or a human PlGF-1 fragment; (2) at least one conjugate; (3) one or more instructions for performing the immunoassay; or (4) or any combination of items (1)-(3). Items (1) and (2) can be any of the antibodies described herein in Section C. Any antibodies provided in such a kit can incorporate a detectable label, such as a fluorophore, radioactive moiety, enzyme, biotin/avidin label, chromophore, chemiluminescent label, or the like. Alternatively, the kit may include reagents for labeling the antibodies or reagents for detecting the antibodies (e.g., detection antibodies) and/or for labeling the antigens or reagents for detecting the antigen.

The methods and kits as described herein also can be adapted for use in a variety of automated and semi-automated systems (including those wherein the solid phase comprises a microparticle), as described, e.g., in U.S. Pat. Nos. 5,089,424 and 5,006,309, and as, e.g., commercially marketed, e.g., by Abbott Laboratories (Abbott Park, Ill.). Abbott's platforms include but are not limited to, ARCHITECT®, AxSYM®, IMx® (see, e.g., U.S. Pat. No. 5,294,404, which is hereby incorporated by reference in its entirety), PRISM®, EIA (bead), and Quantum™ II instruments, as well as other platforms. Moreover, the disclosure optionally is adaptable for the Abbott Laboratories' commercial Point of Care (i-STAT®; Abbott Laboratories, Abbott Park, Ill.) electrochemical immunoassay system for performing sandwich immunoassays. Immunosensors, and their methods of manufacture and operation in single-use test devices are described, for example in, U.S. Pat. No. 5,063,081, U.S. Patent Application 2003/0170881, U.S. Patent Application 2004/0018577, U.S. Patent Application 2005/0054078, and U.S. Patent Application 2006/0160164, which are incorporated in their entireties by reference for their teachings regarding same.

In particular, with regard to the adaptation of the present autoantibody assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample holding chamber of the cartridge there is a layer comprising the second detection antibody labeled with alkaline phosphatase (or other label). Within the fluid pouch of the cartridge is an aqueous reagent that includes p-aminophenol phosphate.

In operation, a sample suspected of containing PlGF-1 is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, PlGF-1, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte PlGF-1 in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® Human PlGF-1 conjugate diluent (Abbott Laboratories, Abbott Park, Ill.) containing 2-(N-morpholino)ethanesulfonic acid (MES), other salt, protein blockers, antimicrobial and detergent. An exemplary calibrator diluent is ARCHITECT® Human PlGF-1 calibrator diluent (Abbott Laboratories, Abbott Park, Ill.), which comprises a buffer containing MES, other salt, a protein blocker and an antimicrobial.

Furthermore, as previously mentioned, the methods and kits optionally are adapted for use on an automated or semi-automated system. Some of the differences between an automated or semi-automated system as compared to a non-automated system (e.g., ELISA) include the substrate to which the capture antibody is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent (Pb264) for a relatively longer incubation time (e.g., about 2 hours), an automated or semi-automated format (e.g., ARCHITECT®) may have a relatively shorter incubation time (e.g., approximately 4 minutes for the ARCHITECT®).

By way of example, and not of limitation, examples of the present disclosure shall now be given.

EXAMPLE 1

Human PlGF-1 (1-131) Wild-type Antigen Human PlGF-1 (1-131) wild-type gene cloning Human PlGF-1 plasmid clone pCMV6-XL4-PlGF1 (Origene Technologies Inc., Rockville, Md., Catalog number TC118512, NM_002632) was used as template. A pair of PCR primers were designed to clone out the human (wild-type) PlGF-1 gene. The 5'-end primer contained a partial sequence of the kappa light chain signal sequence, a NruI restriction site and a 6×His tag, and the 3'-end primer contained a Not I restriction site and a partial sequence of the human PlGF-1 C-terminus. The 5' and 3'-end primers are shown below:

```
Human P/GF-1 5'-end primer (PL01)
                                     (SEQ ID NO: 20)
5'-CCGGCTCGCGATGCCATCATCACCATCACCATCTGCCTGCTGTGCCC
CCCCAGCAGT-3';

Human P/GF-1 3'-end primer (Plrev)
                                     (SEQ ID NO: 21)
5'-CCCCGCGGCCGCTCACCTCCGGGGAACAGCATC-3'.
```

The PCR reaction was executed in 2× reaction Buffer (dNTP), with the 5' and 3' primers and 1.25 units of Pfx DNA polymerase (Invitrogen Corp., Carlsbad, Calif.). The PCR was performed for 30 cycles of 15 seconds at 94° C. followed by 1 minute at 68° C. A total of 30 cycles were performed. The wild-type human PlGF-1 antigen sequence including the signal peptide is shown in FIG. 1.

A 440 bp PCR product was gel purified and restriction enzyme trimmed by Nru I and Not I, and then cloned into a pJV vector and transformed into E. coli DH5α. The pJV vector was obtained from Abbott Laboratories (Abbott Bioresearch Center, Worcester, Mass.) and comprises the ampicillin resistance gene, pUC origin, SV40 origin and EF-1a promoter. The resulting pJV-based vector was referred to as pJV-His-PlGF-1 (1-131) (See, FIG. 2)

The transformed E. coli clones were grown in LB broth overnight with shaking at 37° C. Plasmid DNA was purified from each individual clone with the QIAprep spin miniprep kit (QIAGEN, Valencia, Calif.) followed by sequencing using the BigDye Terminator v3.1 Cycle Sequencing kit (Applied Biosystems, Foster City, Calif.). Plasmid pJV-His-PlGF-1 (1-131)-T1 was selected by sequencing and analyzed by Vector NTI Advance™ software (Invitrogen Corp., Carlsbad, Calif.). Once the pJV clone was identified, separate E. coli DH5α cell banks containing pJV-His-PlGF-1 (1-131) plasmid were made to preserve the pJV clones.

Establishing a Stable CHO Cell Line and Expression of the Human PlGF-1

A Chinese Hamster Ovary (CHO) cell line (B3.2, Abbott Laboratories, Abbott Bioresearch Center, Worcester, Mass.) that lacked the dihydrofolate reductase (DHFR) gene was used for transfection and stable human PlGF-1 expression as described below. The CHO cells were cultured and transfected by standard lipofectamine 2000 transfection with the pJV-His-PlGF-1 (1-131) plasmid per the manufacturer's instructions (Invitrogen Corp., Carlsbad, Calif.). The human PlGF-1 transfected CHO cells were selected for several weeks in alpha MEM medium (Invitrogen Corp., Carlsbad, Calif.) lacking ribonucleosides and deoxyribonucleosides, and containing 5% dialyzed FBS (dFBS) in 96-well plates. Once the CHO clones had grown to more than 50% confluency, the supernatant was tested by enzyme immunoassay (EIA) to rank the performance of the CHO clones. The anti-human PlGF-1 antibody was coated on 96-well EIA plates for at least 1 hour at room temperature, and then were blocked with 2% BSA/PBS buffer for 30 minutes. The supernatant from CHO cell 96 well plates were added into the coated wells and the plates were incubated for at least 1 hour at room temperature. After incubation, the plates were washed and incubated with Biotin labeled human PlGF-1 antigen for about 1 hour. The plates then washed and dried, incubated with Avidin-HRP for 30 minutes. The plates were developed using O-Phenylenediamine-2HCl (OPD) and read at an optical density of 492 nm. The 15 CHO clones that gave the highest signal in the EIA were expanded and re-assayed. Eight clones were then selected based on the highest signal given in the EIA re-assay, and methotrexate (MTX) amplification was done to boost human PlGF-1 secretion.

Methotrexate Amplification of CHO Cell Clone #6305

Transfected CHO cells were passed through a series of media changes of α-MEM supplemented with L-Glutamine and FBS and increasing concentrations of methotrexate (MTX) from 0.02 µM, 0.1 µM, 0.25 µM, 0.5 µM, 1 µM, 2 µM, 5 µM, to 25 µM. All CHO cultures were incubated at 37° C. in a humid incubator supplied with 8% $CO_2$.

The transformed CHO cells on 25 µM MTX were cloned by seeding into Clone Medium for CHO semi-solid growth medium (Genetix Ltd.) for colony selection on the Clonepix Fla. The cells were plated in this semi-solid medium and allowed to grow for approximately 15 days in a 37° C. humidified incubator. Alexa-488 labeled anti-human PlGF-1-255-189 was sprayed on top of the semi-solid medium containing the growing colonies, which were allowed to incubate an additional 24 hours. The semi-solid medium colonies identified as producing the highest amount of human PlGF-1 antigen, as measured by fluorescence intensity generated from the AF488 labeled 1-255-189 immuno-precipitating around the colony, were transferred to a 96-well tissue culture plate with 0.2 mL per well of α-MEM supplemented with 25 µM MTX, 8 mM Glutamine and 5% dialyzed FBS using the ClonepixFL. These plates were incubated for 14-15 days at 37° C. in a humidified incubator. As growth was apparent, the supernatants were tested for the ability to form a sandwich with anti-PlGF-1 2-826-335 and biotin labeled goat anti-PlGF-1 polyclonal antibody (pAb264 from R&D systems) in a microtiter EIA that resulted in the selection of primary clone CHO 6305. This clone was weaned into CHO DHFR negative medium (Sigma-Aldrich, St. Louis, Mo.) with 8 mM L-Glutamine and 25 mM MTX while monitoring antigen secretion in the aforementioned EIA. A cell bank of CHO subclone number 6305 was prepared and named PlGF-1 (1-131) recombinant antigen (rAg) CHO 6305.

Human PlGF-1 (1-131) Wildtype Antigen Purification

CHO cell culture was harvested by centrifugation at 4000 rpm for 20 minutes and the supernatant collected where the human PlGF-1 secreted. The supernatant was dia-filtrated using Pelicon 2 mini (Millipore, Mass.) three times to change the buffer to Phosphate Buffered Saline (PBS), pH 7.2. The dia-filtrated human PlGF-1 solution was purified using nickel-nitrilotriacetic acid (Ni-NTA, Qiagen, CA) metal-affinity chromatography. Basically, the NI-NTA superflow resin was assembled into a FPLC column washed with 3 volume distilled water and pre-equilibrated with wash buffer (50 mM $NaH_2PO_4$, 10 mM imidazole, 300 mM NaCl, 0.05% Tween 20 and adjust the pH to 8.0 with 6N NaOH). The dia-filtrated human PlGF-1 sample was loaded onto the column at flow rate of 0.5 mL/minute, washed with 10-20 volume of wash buffer, the human PlGF-1 protein eluted from column with elution buffer (50 mM $NaH_2PO_4$, 250 mM imidazole, 300 mM NaCl, 0.05% Tween 20 and adjust the pH to 8.0 with 6N NaOH). Purified human PlGF-1 protein was dialyzed three times using 3-5 liters Phosphate Buffered Saline (PBS), pH 7.2.

Gel Permeation Chromatography

Dialyzed protein samples were concentrated to about 5 mL, and pre-equilibrated Sephacryl S100 or G3000 sizing column (e.g., Amersham Biosciences, LKB/Pharmacia) with 10 volumes PBS buffer, pH 7.2. The sample was loaded onto the sizing column at flow rate of 1 mL/minute. All fractions were collected and analyzed by SDS-PAGE gel. Human PlGF-1 dimer fractions were pooled and frozen.

EXAMPLE 2

Figure 3:
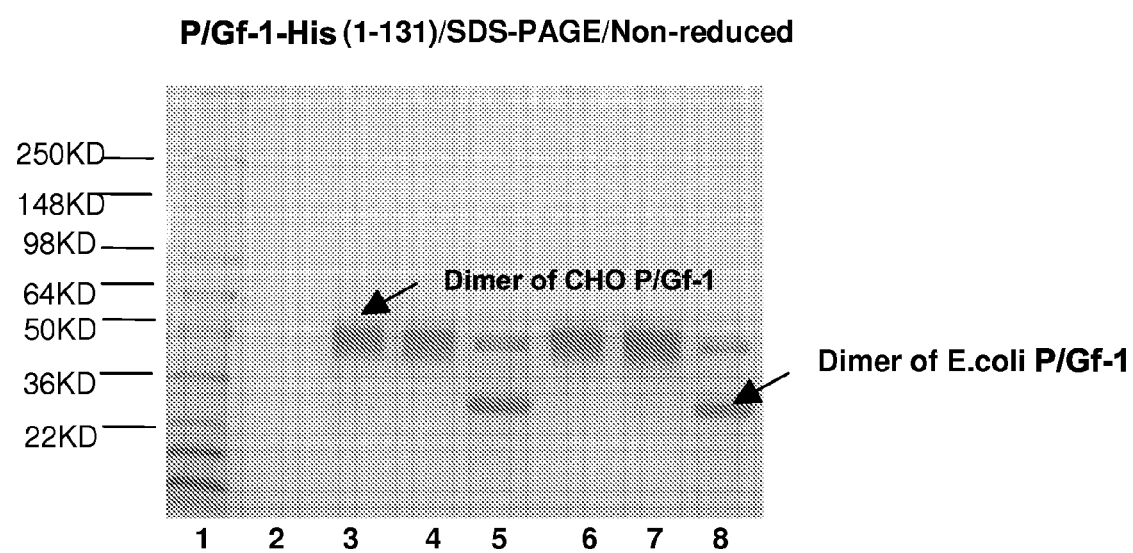
FIG. 3 is a sodium dodecyl sulfate (SDS) polyacrylamide gel electrophoresis (PAGE) showing the conversion of human PlGF-1 in the form of a dimer/tetramer to monomer under reducing conditions in β-mercaptoethanol containing loading buffer as described in Example 2. Lane 1 is the protein marker; Lane 2 is blank; Lane 3 is human PlGF-1-His (1-131), GPC G3000; 2 µg as assessed by OD280; Lane 4 is human PlGF-1-His (1-131), GPC S100; 2 µg as assessed by OD280; Lane 5 is human PlGF-1-His (R&D Systems, produced in E. coli); 2 µg as assessed by OD280; Lane 6 is human PlGF-1-His (1-131), GPC G3000, 2 µg as determined by the Bradford protein assay; Lane 7 is human PlGF-1-His (1-131), GPC S100, 2 µg as determined by the Bradford protein assay; and Lane 8 is human PlGF-1 (R&D Systems, produced in E. coli), 2 µg as determined by the Bradford protein assay.

Characterization of Recombinant Human PlGF-1 Antigen SDS-PAGE Gel Electrophoresis SDS-PAGE gel electrophoresis was performed on CHO cells (CHO clone #6305) expressing human PlGF-1 recombinant antigen under reducing condition or nonreducing conditions. About 3 µg of recombinant human PlGF-1 antigen was mixed with loading buffer with or without reducing agents (β-mercaptoethanol), boiled for 10 minutes, then loaded onto a 4-20% SDS-PAGE gel and run at 80 Volts for 1.5 hours. Monomer human PlGF-1 should migrate at about 20 kDa (calculated MW: 15.5 KDa) and the dimer human PlGF-1 should migrate at about 40 kDa. Functional human PlGF-1 is in dimer form. The CHO cells expressing human PlGF-1 antigen demonstrated that about ~60-80% of the expressed human PlGF-1 is dimer and ~20-40% human PlGF-1 is tetramer. The human PlGF-1 in the form of a dimer/tetramer was converted to monomer under reducing conditions in β-mercaptoethanol containing loading buffer (See, FIG. 3).

Western Blot Analysis

Figure 4A:
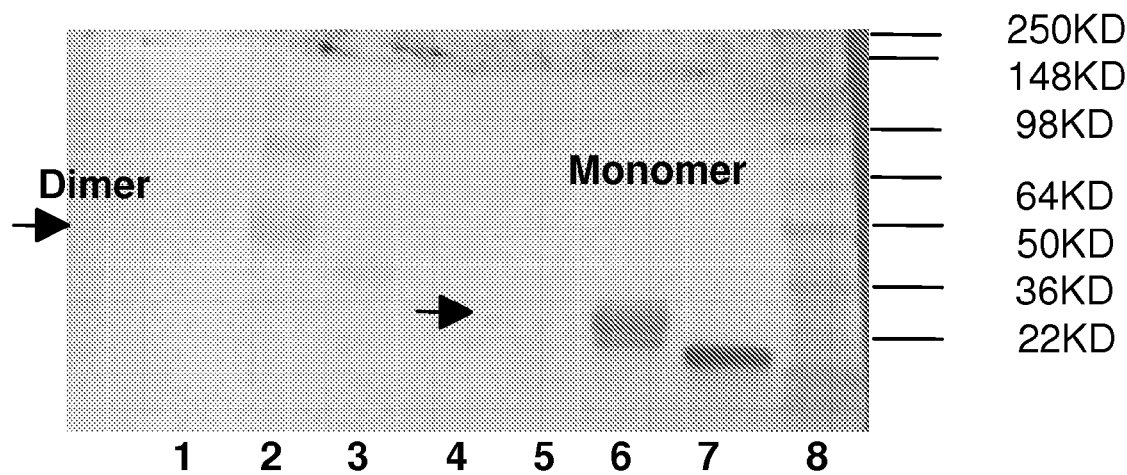
In FIGS. 4A and 4B, Lane 1 is human PlGF-1-His (R&D Systems, produced in E. coli); 2 µg by OD280; Lane 2 is human PlGF-1-His (1-131), GPC S100, 2 µg determined by the Bradford protein assay, non-reduced; Lane 3 is human PlGF-1-His (17-131), GPC S300, ~2 µg by OD280, non-reduced; Lane 4 is blank; Lane 5 is human PlGF-1-His (R&D Systems, produced in E. coli); 2 µg determined by the Bradford protein assay, reduced; Lane 6 is human PlGF-1-His (1-131), GPC S3000, 2 µg determined by the Bradford protein assay, reduced; Lane 7 is human PlGF-1-His (17-131), GPC S300, ~2 µg by OD280, reduced; and Lane 8 is the protein marker.
Figure 4B:
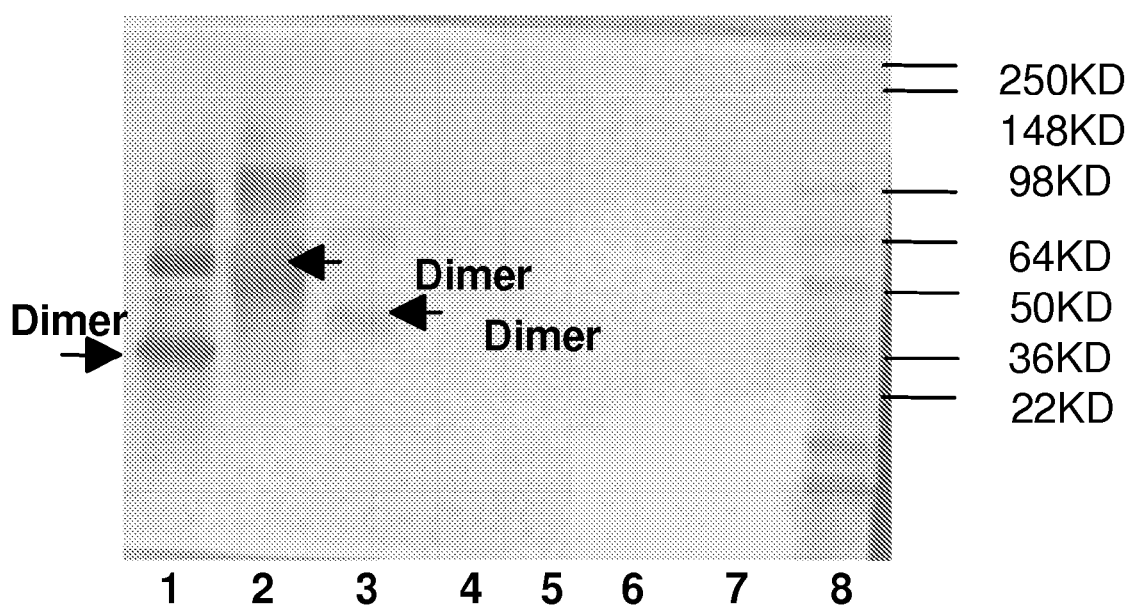
Figure 4C:
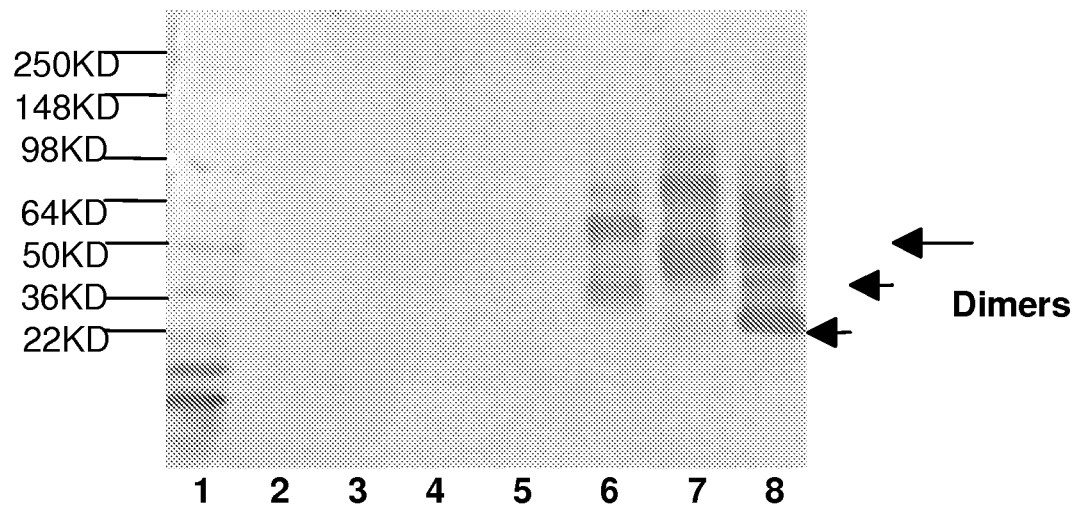
In FIG. 4C, Lane 1 is the protein marker; Lane 2 is human PlGF-1-His (17-131), GPC S300, ~2 µg by OD280, reduced; Lane 3 is human PlGF-1-His (1-131), GPC S3000, 2 µg determined by the Bradford protein assay, reduced; Lane 4 is human PlGF-1-His (R&D Systems, produced in E. coli); GPC G3000 2 µg determined by the Bradford protein assay, reduced; Lane 5 is blank; Lane 6 is human PlGF-1-His (17-131), GPC S300, ~2 µg by OD280, non-reduced; Lane 7 is human PlGF-1-His (1-131), GPC S100, 2 µg determined by the Bradford protein assay, non-reduced; Lane 8 is human PlGF-1-His (1-131), GPC S100, 2 µg determined by the Bradford protein assay, non-reduced.

Approximately 0.5 µg of purified human recombinant human PlGF-1 protein was treated with SDS and 2-mercaptoethanol at 100° C. and electrophoresed in a 4-20% polyacrylamide-SDS gel (Laemmli et al., Nature, 227:680-685 (1970)). Proteins were transferred from the gel to nitrocellulose membranes by electrophoresis at 100 volts for 1-2 hours in a standard transfer buffer comprising 25 mM Tris ((Hydroxymethyl) Aminomethane), 192 mM glycine, and 2.0% methanol, pH 8.3 (Towbin et al., Natl. Acad. Sci., 73:4350-4354 (1979)). After transferring the proteins and blocking the nitrocellulose with 2% BSA in PBS, the nitrocellulose was used to determine the presence of human recombinant antigen. The nitrocellulose membrane was incubated with an appropriate amount of anti-human PlGF-1 or anti His-tag monoclonal antibody (either monoclonal antibody 1-255-713 or 2-826-335) in 10 mL of PBS/2% BSA buffer, pH 7.2. The nitrocellulose membranes were washed with phosphate buffered saline (PBS) pH 7.2, followed by addition of goat anti-mouse IgG antibody conjugated to HRP. The nitrocellulose membranes were incubated for one to two hours at room temperature, followed by washing with PBS. Finally, antibody bound to the protein was visualized by the addition of freshly prepared metal enhanced DAB in stable peroxide buffer (Pierce Biotechnology, Rockford, Ill.). This assay demonstrated that the anti-human PlGF-1 monoclonal antibodies (namely, either monoclonal antibody 1-255-713 or 2-826-335) can bind to recombinant human PlGF-1 antigen in non-reduced forms. (See, FIGS. 4A, 4B and 4C).

Glycosylation Analysis

Figure 5:
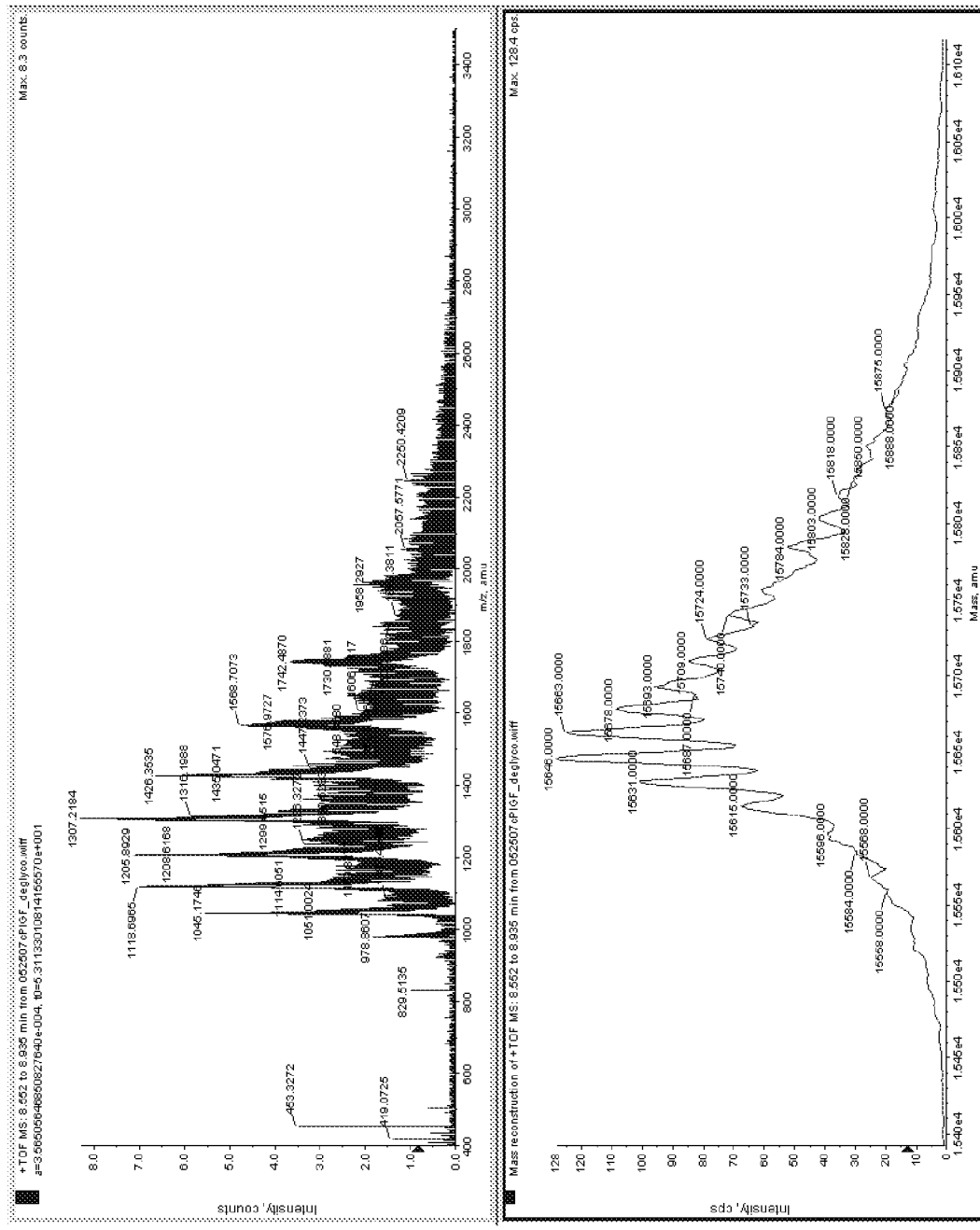
FIG. 5 shows the glycosylation analysis of human PlGF-1 using ESI-MS, specifically, the molecular weights of deglycosylated human PlGF-1. Molecular weight 15646 was the most abundant peak. Top panel abscissa: mass-to-charge ratio ("m/z"), atomic mass unit ("amu"). Bottom panel abscissa: molecular mass ("Mass"), atomic mass unit ("amu").
Figure 7:
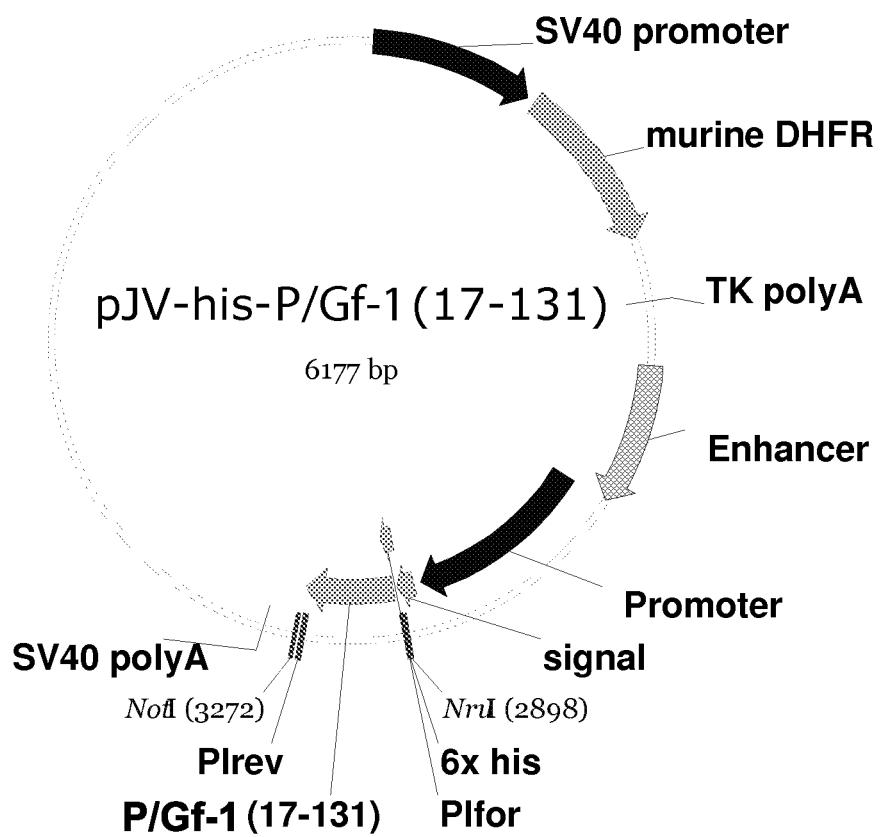
FIG. 7 shows the vector pJV-His-human PlGF-1 (17-131).

CHO cell-expressed human PlGF-1 antigen was analyzed by ESI-MS to determine PlGF-1 glycosylation. The human PlGF-1 solution (30 μL) was incubated with 2.2 μL of denaturation solution, 2.2 μL of detergent, 1 μL each of N-glycanase, O-glycanase, sialidase A, β(1-4) Galactosidase, and β-N-Acetyl-Glucosaminidase at 37° C. for 48 hours. The solution was cleaned-up using Norgen detergent removal device and then desalted using Microcon YM-10 device. The sample was analyzed by ESI-MS. The deglycosylated form of human PlGF-1 showed up as indicated by the appearance of a peak at 15646 Da. This demonstrated there are glycans present on the CHO expressed human PlGF-1 (See, FIG. 5).

Glycosylation Sites Determination

Trypsin digestion, PNGase deglycosylation, and LC/MS/MS were performed to determine the glycosylation sites of CHO cell-expressed human PlGF-1 antigen. 20 μg of human PlGF-1 was vacufuge dried and reconstituted with 30 μL of denaturing buffer (0.5M Tris-HCl, 2.75 mM EDTA, 6 M Guanidine-HCl, adjusted to pH 8.1+/−0.1 w/diluted HCl). The human PlGF-1 was then reduced with DTT and alkylated with iodoacetamide. The solution was desalted using Microcon YM-10 centrifuge device. The desalted solution was incubated with 1:25 (w/w) trypsin at 37° C. overnight. A portion of 20 μL of trypsin digested human PlGF-1 peptides was transferred to a microcentrifuge tube. The solution was then incubated with 1 μL of PNGase overnight. The deglycosylated peptides were desalted using Ziptip C-18 and analyzed by LC/MS/MS using a C18 column. The LC/MS/MS results revealed that CHO cells expressed human PlGF-1 had two glycosylation sites, N21 and N89. N21 was completely glycosylated, while N89 was partially glycosylated (See, FIG. 20). The extracted ion chromatogram showed peak areas ratio around 2.5:1 for peptides derived from human PlGF-1 with glycosylated N89 to peptide derived from human PlGF-1 with non-glycosylated N89.

Carbohydrate Structure Characterization

Figure 21:
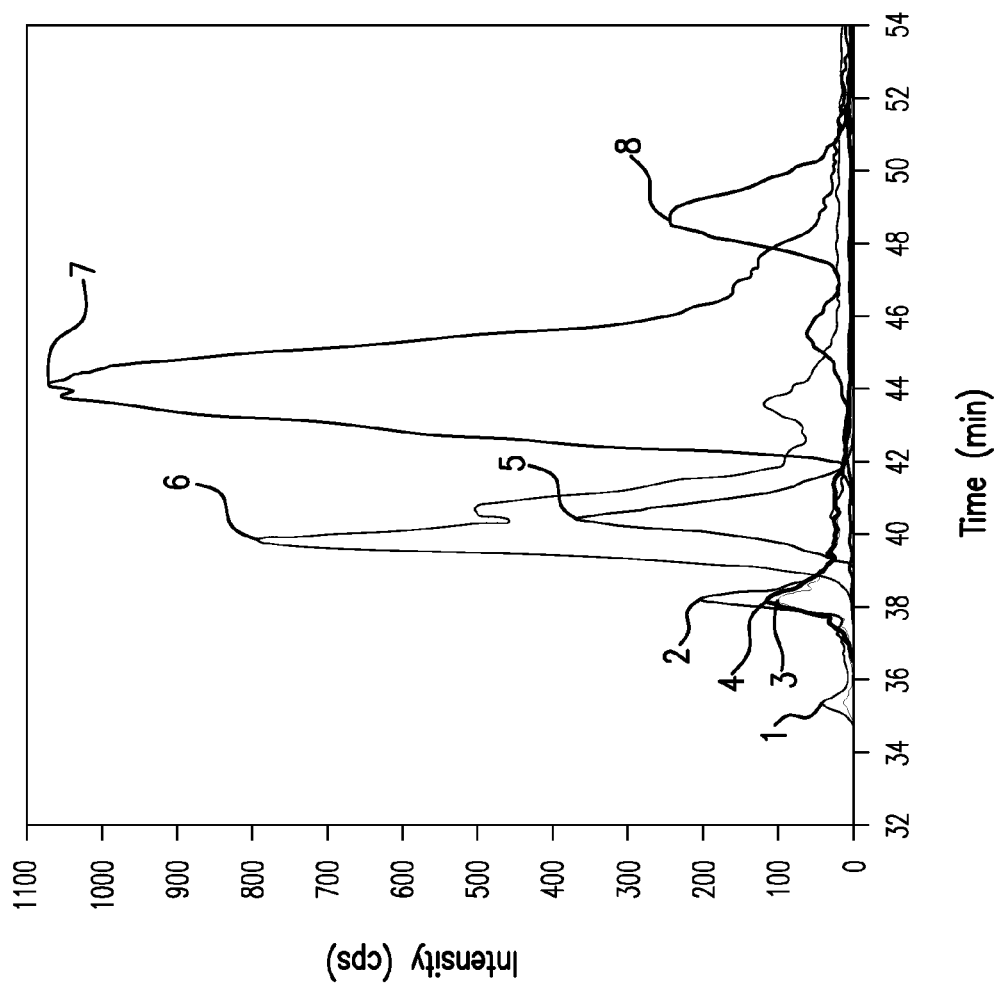
FIG. 21 shows the extracted ion chromatogram of LC/MS analysis of human PlGF-1 N-glycans 1-8 as further described in Example 2.

The N-glycans of CHO cell-expressed human PlGF-1 were analyzed using LC/MS/MS. 35 μL of human PlGF-1 solution was incubated with 2.5 μL of denaturation solution, 2.5 μL of detergent, and 2 μL of Prozyme N-glycanase at 37° C. for 72 hours. The released N-glycans were recovered using Carbograph column. The recovered N-glycans were analyzed by LC/MS/MS using a Hypercarb column. This experiment elucidated structures of eight N-glycans (See, FIG. 21). The data for each of the peaks and the structure for each of the N-glycans is provided in the below Table B.

TABLE B

| Number | Observed m/z | Charge state | Experiment MW | Theoretical MW | Structure |
|---|---|---|---|---|---|
| 1 | 1039.8929 | 2 | 2077.7858 | 2077.7455 | NeuAcGal2Man3GlcNac4-Fuc |
| 2 | 1185.4482 | 2 | 2368.8964 | 2368.8409 | NeuAc2Gal2Man3GlcNAc4-Fuc |
|   | 790.6433 | 3 | 2368.9299 |   |   |
| 3 | 1034.0648 | 3 | 3099.1944 | 3099.1053 | NeuAc2LacNAc2Gal2Man3GlcNAc4-Fuc or LacNAcGal3Man3GlcNAc5-Fuc |
|   | 1550.5689 | 2 | 3099.1378 |   |   |
| 4 | 1368.0192 | 2 | 2734.0384 | 2733.9731 | NeuAc2Gal3Man3GlcNAc5-Fuc |
|   | 912.3489 | 3 | 2734.0467 |   |   |
| 5 | 1009.3865 | 3 | 3025.1595 | 3025.0685 | NeuAc3Gal3Man3GlcNAc5-Fuc |
|   | 1513.5565 | 2 | 3025.113 |   |   |
| 6 | 1131.0991 | 3 | 3390.2973 | 3390.2007 | NeuAc3LacNAcGal3Man3GlcNAc5-Fuc or NeuAc3Gal4Man3GlcNAc6-Fuc |
| 7 | 1228.135 | 3 | 3681.405 | 3681.2961 | NeuAc4Gal4Man3GlcNAc6-Fuc |
| 8 | 1349.8576 | 3 | 4046.5728 | 4046.4283 | NeuAc4LacNAcGal4Man3GlcNAc6-Fuc |

Abbreviations:
Fuc: Fucose;
Gal: Galactose;
GlcNAc: N-acetyl-D-glucosamine;
LacNAc: Galβ1-4GlcNAc disaccharide;
Man: Mannose;
NeuAc: N-acetylneuraminic acid.

EXAMPLE 3

Human PlGF-1 Fragment Antigen 17-131

Human PlGF-1 plasmid clone pCMV6-XL4-human PlGF-1 (Origene Technologies Inc., Rockville, Md., Catalog number TC118512, NM_002632) was used as template. A pair of PCR primers was designed to clone out the human (wild-type) PlGF-1 gene. The 5'-end primer contained a partial sequence of the Kappa light chain signal sequence, a NruI restriction site and a 6×His tag, and the 3'-end primer contained a Not I restriction site and a partial sequence of the human PlGF-1 C-terminus. The 5' and 3'-end primers are shown below:

```
Human P/GF-1 fragment (17-131) 5'-end primer
(Plfor)
                                       (SEQ ID NO: 24)
5'-CCGGCTCGCGATGCCATCATCACCATCACCATTCGTCAGAGGTGGAA
GTGGTACCCTTCCAG-3';

Human P/GF-1 3'-end primer (Plrev)
                                       (SEQ ID NO: 21)
5'-CCCCGCGGCCGCTCACCTCCGGGGAACAGCATC-3'.
```

The PCR reaction was executed in 2× reaction Buffer (dNTP), with the 5' and 3' primers and 1.25 units of Pfx DNA polymerase (Invitrogen Corp., Carlsbad, Calif.). The PCR was performed for 30 cycles of 15 seconds at 94° C. followed by 1 minute at 68° C. A total of 30 cycles were performed. The wild-type human PlGF-1 fragment antigen sequence including the signal peptide is shown in FIG. 6.

A 392 bp PCR product was gel purified and restriction enzyme trimmed by Nru I and Not I, and then cloned into a pJV vector and transformed into E. coli DH5α. The pJV vector was obtained from Abbott Laboratories (Abbott Bioresearch Center, Worcester, Mass.) and comprises the ampicillin resistance gene, pUC origin, SV40 origin, EF-1a promoter. The resulting pJV-based vector is referred to as pJV-His-human PlGF-1 (17-131). The transformed E. coli clones were grown in LB broth overnight with shaking at 37° C. Plasmid DNA was purified from each individual clone with the QIAprep spin miniprep kit (QIAGEN, Valencia, Calif.) followed by sequencing using the BigDye Terminator v3.1 Cycle Sequencing kit (Applied Biosystems, Foster City, Calif.). Plasmid pJV-His-PlGF-1 (17-131)-T1 was selected by sequencing and analyzed by Vector NTI Advance™ software (Invitrogen Corp., Carlsbad, Calif.). Once the pJV clone was identified, separate E. coli DH5 cell banks containing pJV-His-PlGF-1 (17-131) plasmid were made to preserve the pJV clones.

Human PlGF-1 (17-131) Mutant Antigen Transient Expression in HEK293 Cells pJV-His-human PlGF-1 (17-131)-T1 plasmid DNA was Maxi prepared using Endofree plasmid Maxi kit (QIAGEN, Valencia, Calif.) by standard techniques. The high purity plasmid DNA obtained was then transiently transfected into HEK293 cells by 293fectin (Invitrogen Corp., Carlsbad, Calif.). The transiently expressed human PlGF-1 antigen mutant was harvested and dia-filtrated as described in Example 1.

Human PlGF-1 (17-131) Mutant Antigen Purification

The dia-filtrated PlGF-1 (17-131) mutant solution was purified using nickelnitrilotriacetic acid (Ni-NTA, QIAGEN, Valencia, Calif.) metal-affinity chromatography and Gel permeation chromatography as described in Example 1.

Establishing a Stable Human PlGF-1 (17-131) Mutant Expression CHO Cell Line and Methotrexate Amplification A Chinese Hamster Ovary cell line (CHO, B3.2) that lacks the dihydrofolate reductase (DHFR) gene was used for transfection and stable human PlGF-1 expression as in Example 1. The CHO cells were cultured and transfected by standard calcium phosphate-mediated transfection with the plasmid pJV-His-human PlGF-1 (17-131)-T1. The transfected human PlGF-1 (17-131) CHO cells were selected for several weeks in alpha MEM medium (Invitrogen Corp., Carlsbad, Calif.) lacking ribonucleosides and deoxyribonucleosides and containing 5% dialyzed FBS (dFBS) in a 10 cm tissue culture plate. Transfected CHO cells were passed through a series of media changes of α-MEM supplemented with L-Glutamine and FBS and increasing concentrations of methotrexate (MTX) from 0.02 µM, 0.1 µM, 0.25 µM, 0.5 µM, 1 µM, 2 µM, to 5 µM. All CHO cultures were incubated at 37° C. in a humid incubator supplied with 8% $CO_2$. After methotrexate amplification, 5 µM MTX amplified CHO cells were subcloned by end point dilution into alpha MEM+5% dFBS medium supplemented with 5 µM MTX in 96-well plates. The EIA assay was executed to rank the cell clones using anti-PlGF-1 mouse monoclonal antibody coated on the EIA 96-well plates, followed by washing, and then incubating with supernatant from cultured CHO cell clones, then washing again and incubating with biotin labeled human PlGF-1 (R&D Systems, Minneapolis, Minn.), then washing again and incubating with streptavidin (SA)-HRP for another 30 minutes to 1 hour. The plates were developed using O-Phenylenediamine-2HCl (OPD) and read at an optical density of 492 nm. The 2 CHO clones that gave the highest signal in the EIA were identified. A human PlGF-1 (17-131) mutant CHO cell clone #786 was identified and weaned into serum-free medium, i.e., DHFR—CHO medium (Sigma-Aldrich, St. Louis, Mo.). A cell bank of human PlGF-1 (17-131) rAg CHO cell clone #786 was established.

EXAMPLE 4

Figure 8:
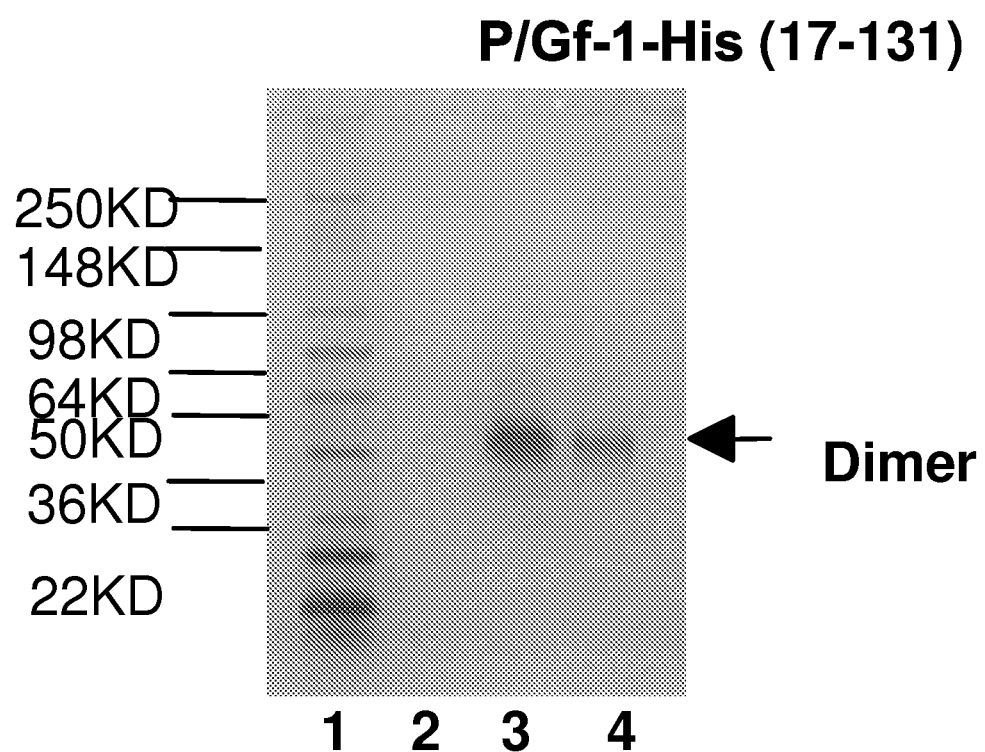
FIG. 8 is a SDS-PAGE gel electrophoresis showing the migration of human PlGF-1 fragment (17-131) in the form of a dimer produced by Chinese Hamster Ovary (CHO) cells as described in Example 4. Lane 1 is the protein marker; Lane 2 is blank; Lane 3 is 6 µg of human PlGF-1 fragment (17-131), non-reduced; and Lane 4 is 2 µg of human PlGF-1 fragment (17-131), non-reduced.

Characterization of Recombinant Human PlGF-1 (17-131) Antigen SDS-PAGE Gel Electrophoresis SDS-PAGE gel electrophoresis was performed on CHO cell-expressed human PlGF-1 fragment (17-131) recombinant antigen under non-reducing conditions. The mutant human PlGF-1 fragment (17-131) antigen was mixed with loading buffer without reducing agents, boiled for 10 minutes, then loaded onto a 4-20% SDS-PAGE gel and run at 80 Volts for 1.5 hours. Monomer human PlGF-1 fragment (17-131) should migrate at about 18 kDa (calculated MW: 13.9 KDa) The dimer human PlGF-1 fragment (17-131) should migrate at about 36 kDa. The CHO cells expressing human PlGF-1 fragment (17-131) antigen demonstrated that about >95% human PlGF-1 fragment (17-131) is in dimer form (See, FIG. 8). Western blot analysis is described in Example 2.

EXAMPLE 5

Human PlGF-1 Antigen 1-131 with Enterokinase Cleavage Site

Human PlGF-1 plasmid clone pCMV6-XL4-PlGF1 (Origene Technologies Inc., Rockville, Md., Catalog number TC118512, NM_002632) was used as template.

A pair of PCR primers was designed to clone out the human (wild-type) human PlGF-1 gene. The 5'-end primer contained a partial sequence of the Kappa light chain signal sequence, a NruI restriction site and a 6×His tag, and the 3'-end primer contained a Not I restriction site and a partial sequence of the human PlGF-1 C-terminus. The 5' and 3'-end primers are shown below:

```
PlGF-1 His-EK-(1-131) 5'-end primer (P103)
                                       (SEQ ID NO: 25)
5'-GGC TCG CGA TGC CAT CAT CAC CAT CAC CAT GGT GCA
GAT GAC GAC GAC AAG CTG CCT GCT GTG CCC CCC
CAG -3';

PLGF-1 3'-end primer (Plrev)
                                       (SEQ ID NO: 21)
5'-CCCCGCGGCCGCTCACCTCCGGGGAACAGCATC-3'.
```

The PCR reaction was executed in 2× reaction Buffer (dNTP), with the 5' and 3' primers and 1.25 units of Pfx DNA polymerase (Invitrogen Corp., Carlsbad, Calif.). The PCR was performed for 30 cycles of 15 seconds at 94° C. followed by 1 minute at 68° C. A total of 30 cycles were performed. The wild-type human PlGF-1 antigen sequence including the signal peptide is shown in FIG. 9.

Figure 10:
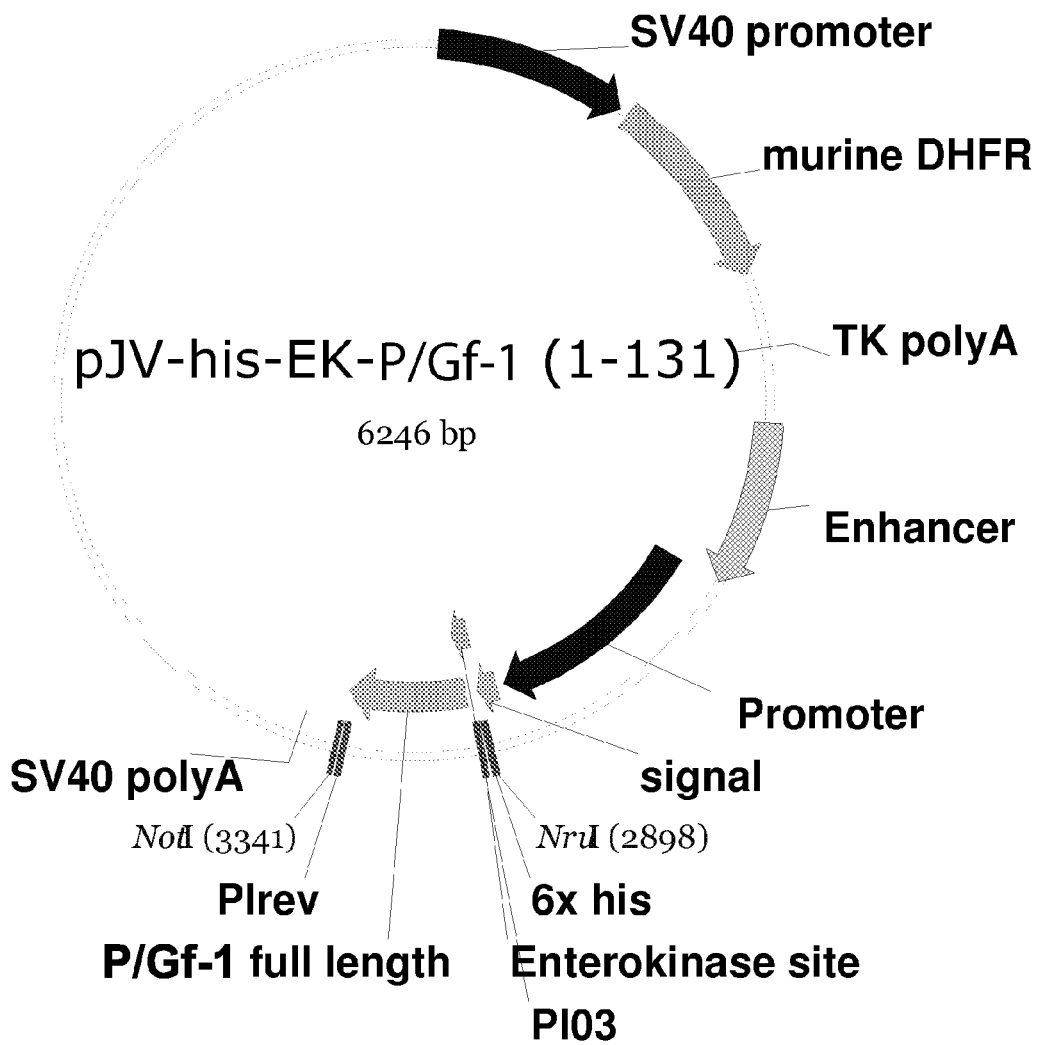
FIG. 10 shows the vector pJV-His-human PlGF-1 (1-131).

A 460 bp PCR product was gel purified and restriction enzyme trimmed by Nru I and Not I, and then cloned into a pJV vector and transformed into *E. coli* DH5α. The pJV vector was obtained from Abbott Laboratories (Abbott Bioresearch Center, Worcester, Mass.) and comprises the ampicillin resistance gene, pUC origin, SV40 origin, EF-1a promoter. The resulting pJV-based vector is referred to as pJV-His-human PlGF-1 (1-131) (See FIG. 10).

The transformed *E. coli* clones were grown in LB broth overnight with shaking at 37° C. Plasmid DNA was purified from each individual clone with the QIAprep spin miniprep kit (QIAGEN, Valencia, Calif.) followed by sequencing using the BigDye Terminator v3.1 Cycle Sequencing kit (Applied Biosystems, Foster City, Calif.). Plasmid pJV-His-EK-PlGF-1 (1-131)-T3 was selected by sequencing and analyzed by Vector NTI Advance™ software (Invitrogen Corp., Carlsbad, Calif.). Once the pJV clone was identified, separate *E. coli* DH5αcell banks containing pJV-His-EK-PlGF-1 (1-131)-T3 plasmid were made to preserve the pJV clones.
Establishing a Stable PlGF-1 (1-131) EK Mutant Expression CHO Cell Line and Methotrexate Amplification A Chinese Hamster Ovary (CHO) cell line (CHO, B3.2) that lacks the dihydrofolate reductase (DHFR) gene was used for transfection and stable human PlGF-1 expression as in Example 1. The CHO cells were cultured and transfected by standard lipofectamine 2000 transfection with the pJV-His-human PlGF-(1-131) plasmid per the manufacturer's instructions (Invitrogen Corp., Carlsbad, Calif.). The transfected human PlGF-1 (1-131) EK CHO cells were selected for several weeks in alpha MEM medium (Invitrogen Corp., Carlsbad, Calif.) lacking ribonucleosides and deoxyribonucleosides and containing 5% dialyzed FBS (dFBS) in a 10 cm tissue culture plate. Once the CHO clones had grown to more than 50% confluency, the supernatant was tested by enzyme immunoassay (EIA) to rank the performance of the CHO clones. The anti-human PlGF-1 antibody was coated on 96-well EIA plates for at least 1 hour at room temperature, and then reactions were blocked with 2% BSA/PBS buffer for 30 minutes. The supernatant from 96 well plates were added into the coated wells and the plates were incubated for at least 1 hour at room temperature. After incubation, the plates were washed and incubated with biotin-labeled human PlGF-1 antigen for about 1 hour. The plates then washed and dried, incubate with avidin-HRP for 30 minutes. The plates were developed using O-Phenylenediamine-2HCl (OPD) and read at an optical density of 492 nm. The 18 CHO clones that gave the highest signal in the EIA were expanded and re-assayed. Eight clones were then selected based on the highest signal given in the EIA re-assay, and methotrexate (MTX) amplification was done to boost human PlGF-1 secretion.
Methotrexate Amplification of CHO Cell Clone #350

Transfected CHO cells were passed through a series of media changes of α-MEM supplemented with L-Glutamine and FBS and increasing concentrations of methotrexate (MTX) from 0.02 μM, 0.1 μM, 0.25 μM, 0.5 μM, 1 μM, 2 μM, 5 μM, to 25 μM. All CHO cultures were incubated at 37° C. in a humid incubator supplied with 8% $CO_2$. The transfected CHO cells on 25 μM MTX were cloned by seeding into Clone Medium for CHO semi-solid growth medium (Genetix Ltd.) for colony selection on the Clonepix Fla. The cells were plated in this semi-solid medium and allowed to grow for approximately 15 days in a 37° C. humidified incubator. Alexa-488 labeled Anti-human PlGF-1 1-255-189 was sprayed on top of the semi-solid medium containing the growing colonies, which were allowed to incubate an additional 24 hours. The semi-solid medium colonies identified as producing the highest amount of human PlGF-1 antigen, as measured by fluorescence intensity generated from the AF488 labeled 1-255-189 immuno-precipitating around the colony, were transferred to a 96-well tissue culture plate with 0.2 mL per well of α-MEM supplemented with 25 μM MTX, 8 mM Glutamine and 5% dialyzed FBS using the ClonepixFL. These plates were incubated for 14-15 days at 37° C. in a humidified incubator. As growth was apparent, the supernatants were tested for the ability to form a sandwich with anti-human PlGF-1 2-826-335 and biotin labeled goat anti-PlGF polyclonal antibody (pAb264 from R&D Systems) in a microtiter EIA that resulted in the selection of primary clone CHO 350. This clone was weaned into CHO DHFR negative medium (Sigma-Aldrich, St. Louis, Mo.) with 8 mM L-Glutamine and 25 μM MTX while monitoring antigen secretion in the aforementioned EIA. A cell bank of CHO subclone number 350 was prepared and named human PlGF-1 (1-131) EK rAg CHO 350.
Human PlGF-1 (1-131) EK Antigen Purification CHO cell culture harvested and dia-filtrated as described in Example 1. The dia-filtrated human PlGF-1 (1-131) EK solution was purified using nickelnitrilotriacetic acid (Ni-NTA, QIAGEN, Valencia, Calif.) metal-affinity chromatography as described in Example 1.

EXAMPLE 6

Characterization of Recombinant Human PlGF-1 (1-131) EK Antigen

Figure 11:
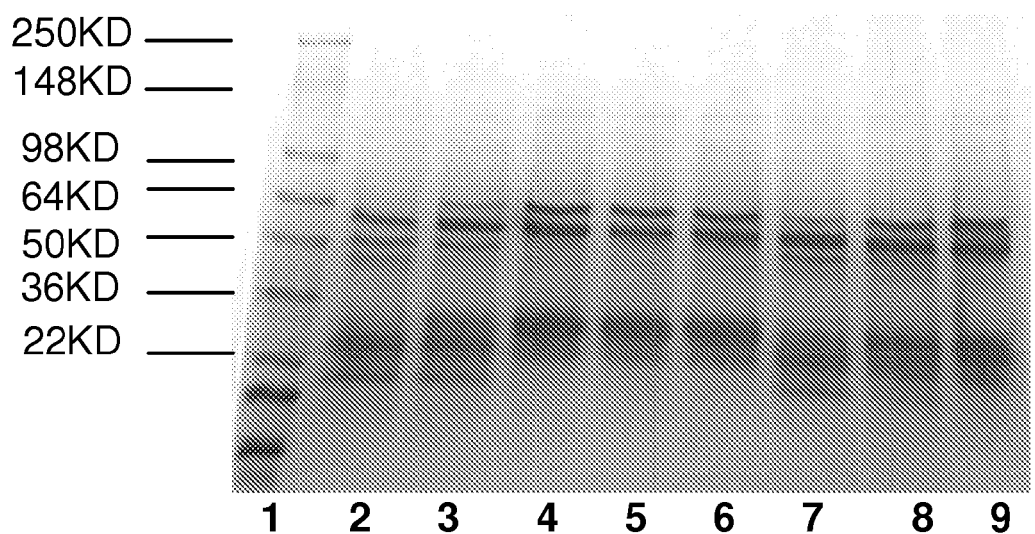
FIG. 11 is a SDS-PAGE gel electrophoresis showing the migration of recombinant human PlGF-1 (1-131) enterokinase antigen as described in Example 6. Lane 1 is the protein marker; Lane 2 is 40 µl of human PlGF-1-EK plus 3 U of Invitrogen enterokinase at room temperature; Lane 3 is 40 µl of human PlGF-1-EK plus 0.5 U of Invitrogen enterokinase at room temperature; Lane 4 is 40 µl of human PlGF-1-EK plus 0.05 U of Invitrogen enterokinase at room temperature; Lane 6 is 40 µl of human PlGF-1-EK with no enterokinase control at room temperature; Lane 7 is 40 µl of human PlGF-1-EK plus 2 U of Novagen enterokinase at room temperature; Lane 8 is 40 µl of human PlGF-1-EK plus 0.2 U of Novagen enterokinase at room temperature; and Lane 9 is 40 µl of human PlGF-1-EK with no enterokinase control at 4° C.

Nickel column-purified human PlGF-1-enterokinase (EK) antigen was pooled, and a portion of the sample was used for enterokinase cleavage at room temperature. Varying amounts of the enterokinase (Invitrogen Corp., Carlsbad, Calif. or Novagen, Calif.) was incubated with human PlGF-1-EK at room temperature overnight, then analyzed on SDS-PAGE gel electrophoresis under reduced conditions. The human PlGF-1-EK antigen samples were mixed with loading buffer with reducing agents, boiled for 10 minutes, then loaded onto a 4-20% SDS-PAGE gel and run at 80 Volts for 1.5 hours. Monomer human PlGF-1-EK (1-131) should migrate at about 20 kDa (calculated MW: 16.2 KDa). Enterokinase treatment removed the 6xHis tag and enterokinase cleavage site, so the treated antigen is 1557 dalton less than human PlGF-1-EK (See, FIG. 11).

EXAMPLE 7

Development of PlGF-1 Murine Cell Lines

The antigen used to stimulate an immune response in the mice was recombinant human PlGF-1 (R&D Systems, Minneapolis Minn.), which is reported as having been produced in *E. coli*. RBf/Dnj mice from Jax Labs, Bar Harbor, Me.; were used in the study. Mice were given 5 bi-weekly immunizations of 5 μg of human PlGF-1 coupled with a carrier protein followed by 3 bi-weekly immunizations of 2.5 μg of human PlGF-1 without the carrier protein. These immunizations alternated between Fruend's Adjuvant (DIFCO, Detroit Mich.) and two variations of RIBI Adjuvant (MPL+TDM and MPL+TDM+CWS) (Corixa, Hamilton, Mo.). Sera samples from the mice were taken 14 days after the eighth immunization for evaluation by enzyme linked immunoassay (EIA).

Rabbit anti-mouse IgG Fc (Jackson Immunoresearch, West Grove Pa.) was coated on 96 well microtiter EIA plates (Nunc Corporation, Rochester N.Y.) at 5 ug/mL). After the capture reagent had been coated on the solid phase, it was removed and any unoccupied binding sites remaining on the plates were blocked using a 2% BSA solution in phosphate buffered saline (PBS) (block solution). The plates were washed three times with distilled water and log 4 serial dilutions of control antibodies and mouse sera samples were added for a one-hour incubation. The plates were washed four times with distilled water and a 1500 pg/mL solution of biotin labeled human PlGF-1 antigen, diluted in PBS, was added to the plate and allowed to incubate for 60 minutes. Following this incubation, the antigen was washed from the plate with distilled water and Streptavidin-HRPO (Zymed, San Francisco Calif.) diluted to 200 ng/mL in block solution was added to the plate and allowed to incubate for 30 minutes. Following this incubation, the plates were washed four times with distilled water and o-phenylenediamine substrate (OPD; Abbott Laboratories, Abbott Park, Ill.) was used as the chromogen to generate signal. Plates were read at 492 nm and the results were plotted to determine the sera dilution that generates approximately 50% of maximal binding. The sera dilution that generated 50% binding for each mouse was then used in a human PlGF-1 antigen titration EIA. Rabbit anti-mouse IgG Fc was once again coated on 96 well microtiter EIA plates at 5 ug/mL. After the capture reagent had been coated on the solid phase, it was removed and the plates were blocked. The plates were washed three times with distilled water. The dilution that generated 50% of maximal binding was determined for each mouse and added to the plates, then incubated for 60 minutes. Following incubation, the plates were washed four times with distilled water and log 4 dilutions of biotin labeled human PlGF-1 starting at 4000 pg/mL were added and allowed to incubate for 60 minutes. Following this incubation, the antigen was washed from the plate with distilled water and streptavidin-HRPO diluted to 200 ng/mL in block solution was added to the plate and allowed to incubate for 30 minutes. The plates were once again washed four times with distilled water and OPD was used as a chromogen to generate signal. The results from this assay showed that mouse numbers 528, 531 and 532 exhibited high titer and affinity to human PlGF-1 antigen compared to mouse numbers 527, 529 and 530.

After demonstrating high titer and affinity to the human PlGF-1 antigen, mouse numbers 528, 531 and 532 were allowed to rest prior to pre-fusion boost of antigen. On week 45, three days prior to fusion, the mice were anesthetized and an incision was made in order to open the body cavity and expose the spleen. Each mouse was given a 10 µg injection of recombinant human PlGF-1 antigen diluted in 0.9% saline solution directly into the spleen, and an additional 10 µg into the body cavity around the spleen. The incisions were closed using surgical staples and the mice were rested before fusion. The splenocytes from these mice were used for human PlGF-1 Fusion # 1. Two mice from the group consisting of mouse numbers 527, 529, 530 and 533 were used for human PlGF-1 fusion # 2. These four mice lost their identification tag following sera sampling so their original identification number was lost. They were assigned mouse numbers 1 and 2. On week 47, three days prior to fusion, these mice were anesthetized and an incision was made in order to open the body cavity and expose the spleen. Each mouse was given a 10 µg injection of recombinant human PlGF-1 antigen diluted in 0.9% saline solution directly into the spleen, and an additional 10 µg into the body cavity around the spleen. The incisions were closed using surgical staples and the mice were rested before fusion.

On the day of each fusion, the mice were euthanized and their spleens containing anti-human PlGF-1 splenocytes were harvested and placed into Hybridoma Serum Free Medium (HSFM) (Invitrogen Corporation, Grand Island N.Y.). A cell fusion was performed as described by Kohler and Milstein (*Nature*, 256:495-7 (1975)). Each mouse spleen was placed into a separate petri dish containing HSFM. The splenocytes were perfused out of each spleen using a syringe containing HSFM and cell scraper, then counted using a hemocytometer. For human PlGF-1 Fusion # 1, approximately $2.0 \times 10^7$ splenocytes were pooled from mouse numbers 528 and 531 along with approximately $3.0 \times 10^7$ splenocytes from mouse 532. For human PlGF-1 Fusion # 2, approximately $3.5 \times 10^7$ splenocytes from mouse 1 was pooled with approximately $1.6 \times 10^7$ splenocytes from mouse 2. The pooled splenocytes for each fusion were washed by centrifugation into a cell pellet and re-suspended in HSFM. The splenocytes were mixed with an equal number of SP 2/0 myeloma cells and centrifuged into a pellet. The fusion was accomplished by exposing the splenocytes and SP 2/0 cells to 50% polyethylene glycol (PEG) (ATCC Molecular Weight 1300-1600, Manassas Va.) in HSFM. One milliliter of the PEG solution was added to the cell pellet over 30 seconds, followed by an additional one-minute incubation. The PEG and cell pellet was diluted by slowly adding thirty milliliters of HSFM over 30 seconds. The fused cells were then removed from suspension by centrifugation and decanting the supernatant. The cell pellet for both fusions were re-suspended into HSFM supplemented with 15% FBS (Hyclone Laboratories, Logan Utah), HAT (Hypoxanthine, Aminopterin, Thymidine) (Sigma Laboratories, St. Louis, Mo.), HT Supplement (Invitrogen Corporation, Grand Island N.Y.), Hybridoma Cloning Factor (Bioveris Corporation, Gaithersburg Md.), and L-Glutamine (Invitrogen Corporation, Grand Island N.Y.) in order to select for hybridomas. The cells were plated at 0.2 mL per well into sixteen 96 well cell culture plates for fusion # 1 and thirteen plates for fusion # 2. At days 5 and 7 for fusion #1 and days 5, 7, and 12 for fusion # 2, one half of the medium in each well was removed by aspiration and replaced with HSFM supplemented with 15% FBS, HT Supplement, and L-glutamine. Hybridomas were allowed to grow for 10 to 12 days prior to supernatant screening for antibody production.

Cell supernatant samples were analyzed for anti-human PlGF-1 antibodies by EIA. Rabbit anti-mouse IgG Fc was coated on 96 well microtiter EIA plates at 5 µg/mL. After the capture reagent has been coated on the solid phase, it was removed and any open binding sites on the plates were blocked using block solution. The wells were washed three times with distilled water and cell supernatants were added to the blocked plates and allowed to incubate at room temperature for at least one hour. The anti-mouse IgG Fc will capture the anti-human PlGF-1 mouse antibody from the supernatant. Following the incubation, the supernatants were washed off using distilled water. Human PlGF-1 antigen, which has been labeled with biotin, is added to the plates at 1500 pg/mL and incubated for 60 minutes. Following this incubation, the antigen is washed from the plates using distilled water. Streptavidin-HRPO diluted to approximately 200 ng/mL in block solution is added to the plates and allowed to incubate for 30 minutes. The plates were washed four times with distilled water and o-phenylenediamine substrate was used as the chromogen to generate signal. Plates were read at 492 nm and the results were analyzed. Hybrids were considered positive if they had an EIA signal at least 3 times greater than background. Hybrid numbers 1-255 and 2-826 were selected as each had an EIA signal at least 3 times greater than background.

The positive hybrids were expanded to 24 well plates in HSFM supplemented with 10% FBS and Ht supplement. Following 4-11 days growth, the 24 well cultures were evaluated by EIA in the same manner as described in this example and once again the hybrids generating signal at least 3 times greater than background were considered positive and selected for cloning (See, Table 2, below). Both hybrid numbers 1-255 and 2-826 each had an EIA signal at least 3 times greater than background.

Hybrid 1-255 and 2-826 were cloned using Fluorescence Activated Cell Sorting (FACS) to sort live hybrid cells. From a cell suspension, viable cells were sorted from dead cells by monitoring the forward and side light scattering properties of individual cells by FACS. One or ten viable cells were individually plated into wells containing 0.2 mL of HT supplemented H—SFM with 10% FBS within 96-well tissue culture plates. The plates were allowed to incubate for 7 to 14 days at 37° C. in a humidified incubator. As growth became apparent, the cell culture supernatants were tested with anti-human PlGF-1 microtiter EIA for reactivity to human PlGF-1 as previously described in this example. Clone 1-255-189 and 2-826-127 were selected for epitope grouping and binding pair evaluation, as each of these clones had a signal at least 3 times greater than background.

Antibodies from the subcloned anti-human PlGF-1 clones (1-255-189 and 2-826-127) were biotin labeled for use in an epitope grouping assay. Briefly, Sulfo-NHS-LC-Biotin (Pierce Chemical, Rockford, Ill.) was added to purified antibody at 20 molar excess and allowed to incubate for 30 minutes. Unlabeled biotin was removed through dialysis in PBS and the monoclonal antibodies (MAbs) were tested by EIA to confirm their labeling. Recombinant human PlGF-1 antigen was coated on 96 well microtiter plates at 500 ng/mL. After the antigen has been coated on the solid phase, open binding sites were blocked with a 2% BSA/PBS block solution. The plates were washed three times with distilled water and either block solution or unlabeled MAb solution (i.e., purified antibody from 1-255-189 or 2-826-127 lacking any biotin label) at 50 µg/mL was added to the plate and allowed to incubate for approximately 60 minutes. Dilutions of the biotin-labeled MAbs were layered on top of the BSA block solution or the unlabeled MAbs and allowed to incubate for 10-15 minutes. The microtiter plates were washed four times with distilled water. Streptavidin-HRPO diluted to approximately 200 ng/mL in block solution was added to the plates and allowed to incubate for 30 minutes. The plates were washed four times with distilled water and o-phenylenediamine substrate was used as the chromogen to generate signal. Plates were read at 492 nm and the results were analyzed. The MAbs qualified for use in epitope grouping assays based on (a) an ability to bind to the human PlGF-1 antigen coated on the solid phase and generate an assay signal when added to the wells with BSA block (1-255-189-Bt/block and 2-826-127-Bt/block), and (b) blockage of this signal by the corresponding unlabeled version of the MAb (1-255-189-Bt/unlabeled self and 2-826-127-Bt/unlabeled self).

A dilution of biotin labeled MAb that generated approximately 50% of the maximal binding signal when no competitor was present, and was completely blocked by a 50 µg/mL solution of the corresponding unlabeled version of the MAb was chosen for the epitope grouping study. The epitope-grouping assay was completed using the same assay format just described. In this experiment, unlabeled purified antibody from all the anti-human PlGF-1 hybridomas were tested for their ability to compete with the labeled version of each anti-human PlGF-1 MAb for binding spots on the human PlGF-1 antigen coated plates. If an unlabeled MAb inhibited the binding of a labeled MAb, this indicates that it shares a similar binding epitope. If an unlabeled MAb does not compete for binding, it is directed against a different region. Based on these assay results, the panel of anti-human PlGF-1 MAbs can be epitope grouped and good binding pairs for a sandwich assay can be predicted. The epitope grouping results with 32 MAbs demonstrated that 1-255-189 and 2-826-127 bind to distinctly different epitopes on the human PlGF-1 antigen (namely, 1-255-189 binds to so-called 'epitope group 2' and 2-826-127 binds to so-called 'epitope group 1') and would make a good binding pair for a sandwich assay.

The ability of MAbs 1-255-189 and 2-826-127 to form a sandwich with human PlGF-1 in an EIA format was tested. A 1 µg/mL solution of 1-255-189 prepared in PBS was coated on the solid phase of 96 well microtiter assay plates and allowed to incubate for approximately 16 hours at 2-8° C. After the capture reagent has been coated on the solid phase, it was removed and any open binding sites on the plates were blocked using a BSA/PBS block solution. Human PlGF-1 antigen dilutions from 0 to 1000 pg/mL were added to the microtiter plate and allowed to incubate for 60 minutes. The antigen solution was then removed and the plates were washed four times with distilled water. Biotin labeled human PlGF-1 MAb 2-826-127 at a 125 ng/mL concentration prepared in blocking buffer was added and allowed to incubate for 60 minutes. The plates were washed four times with distilled water and streptavidin-HRPO diluted to approximately 200 ng/mL in block solution was added and allowed to incubate for 30 minutes. The plates were washed with distilled water and o-phenylenediamine substrate was used as the chromogen to generate signal. Plates were read at 492 nm and the resulting antigen titration curve was plotted (data not shown). The plot obtained confirms the capability of these two MAbs to form a sandwich with human PlGF-1.

Clone 1-255-189 was weaned for growth in serum free medium (Invitrogen H—SFM with 1.0 mg/mL Albumax). Following weaning, the cell line was cloned by growing cells in semi-solid tissue culture medium and picking colonies for subculture with the ClonepixFL instrument (Genetix Ltd., Hampshire, UK). Briefly, the cell suspension was diluted into a 2× concentration of HSFM supplemented with 10% FBS and an equal volume of Clone Matrix methylcellulose medium (Genetix Ltd.). The semi-solid cell suspension was seeded into tissue culture plates and allowed to incubate for approximately 7 days at 37° C. At the time of cell plating, a 5 µg/mL solution of goat anti-mouse IgG-FITC solution (Clone Detect, Genetix Ltd.) was added to the semi-solid medium. A colony grown in the semi-solid medium was considered clonal because the single cell from which it initiates was not allowed to move and mix with other cells. An immunoprecipitation reaction occurs between the antibody being produced by the colony and the goat anti-mouse IgG Fc-FITC that fluoresces. The brighter the fluorescence the more antibody being produced. Colonies were analyzed for fluorescence on the ClonepixFL and the ones with the most intense signal were selected for automated transfer to 96 well tissue culture plates containing HSFM with 10% FBS. These plates were incubated for 7-10 days and clone supernatants were tested for anti-human PlGF-1 titer as previously described in this example. Clone 1-255-713 was cloned two additional times using (FACS) to sort live hybrid cells as previously described in this example. One viable cell was individually plated into wells containing 0.2 mL of HT supplemented H—SFM with 10% FBS within 96-well tissue culture plates. The plates were allowed to incubate for 7 to 14 days at 37° C. in a humidified incubator. As growth became apparent, the cell culture supernatants were tested with anti-human PlGF-1 microtiter EIA for reactivity to human PlGF-1 as previously described in this example. This cell line, now referred to as 1-255-2675 was weaned to HSFM without FBS. Cell line 1-255-2675 was selected for scale up and cell banking purposes. Liquid nitrogen freezers are used for long-term storage of the cell bank. The antibody produced by cell line 1-255-2675 is identical to that produced by its parent clone, 1-255-713.

Clone 2-826-127 was weaned into H-SFM supplemented with L-Glutamine and Albumax (Invitrogen) and then cloned using Fluorescence Activated Cell Sorting (FACS) to sort individual, live hybridoma cells. From a cell suspension, viable cells were sorted from dead cells by monitoring the forward and side light scattering properties of the individual cells using FACS. Single viable 2-826-127 cells were individually plated into wells containing 0.25 mL of HSFM supplemented with 10% FBS in 96-well tissue culture plates. The plates were incubated for 7 to 14 days at 37° C. in a humidified incubator. As growth became apparent, the cell culture supernatants were tested for anti-human PlGF-1 titer as previously described in this example. Clone 2-826-335 was selected for additional evaluation. This cell line was weaned to HSFM without FBS. Cell line 2-826-335 was selected for scale up and cell banking purposes. Liquid nitrogen freezers were used for long-term storage of the cell bank.

EXAMPLE 8

Characterization of Antibodies

Purified antibody from the 1-255-2675 and 2-826-335 cell lines was tested with the Isostrip Mouse Monoclonal Antibody Isotyping Kit (Roche Diagnostics Indianapolis, Ind.). An aliquot of 150 µL of 0.15 or 0.2 µg/mL of each sample was added to the development tube and mixed. An Isostrip was added to each tube and incubated for 5-10 minutes until color development occurred on the strip's band. The results indicated that both the 1-255-2675 is mouse IgG2a subtype with kappa light chain and 2-826-335 is mouse IgG1 subtype with kappa light chain.

Purified antibody was evaluated on SDS-PAGE and IEF gels using the PhastSystem (GE Healthcare Bio-Sciences Corp. Piscataway, N.J.) according to the manufacturer's directions. DTT treated test samples were loaded into the lanes of the SDS-PAGE gel at concentrations from 0.1 to 0.4 mg/mL. Color development with silver stain for the 1-255-713 MAb indicated that the light chain molecular weight (MW) was ~27 kDa and the heavy chain MW was ~50 kDa. Development of the 2-826-335 MAb indicated that the light chain molecular weight (MW) was ~28 kDa and the heavy chain MW was ~52 kDa. 25 µl of the IEF test samples were loaded into the lanes at 0.2 µg/mL. Color development of the IEF test runs indicated the pI range of the 1-255-713 MAb was 6.78-7.80 with 8 visible bands. Development of the 2-826-335 MAb indicated the pI range was 5.98-6.87 with 8 visible bands.

EXAMPLE 9

Antibody Production and Purification

The 1-255-713 and 2-826-335 cell lines were expanded in HSFM and seeded into roller bottles at approximately 0.5× $10^5$ cells/mL. The cultures were incubated at 37° C. while rotating at approximately 1 revolution per minute for 10-14 days, or until a terminal end culture was obtained. The terminal roller bottle supernatant was harvested and clarified with a 0.45 micron filter. The clarified supernatant was concentrated using a Pellicon system and filtered with a 0.45 micron filter. The MAb concentrate was diluted with an equal volume of 1.5 M glycine/3 N NaCl buffer at pH 8.9, then loaded onto a pre-equilibrated 5 mL Protein A column using the AKTA automated purification system (Amersham/Pharmacia). The column was then washed with 5 column volumes of binding buffer and when a stable baseline is achieved, the MAb is eluted with a pH 3.0 citrate buffer. The MAb was then transferred to a 70 mL G25 column for an exchange into PBS then further dialyzed in PBS using 10,000 molecular weight cut of dialysis membrane. The antibody was aliquoted and stored at −70° C.

EXAMPLE 10

Affinity/Kinetic Characterization of Anti-Human PlGF-1 Antibody for Human PlGF-1 Antigen The affinities/kinetics of monoclonal antibodies 1-255-713 and 2-826-355 for human PlGF-1 (comprising amino acids 1-131) and human PlGF-1 fragment (comprising amino acids 17-131 (See, e.g., SEQ ID NO:5)) antigens were determined using a SPR (Surface Plasmon Resonance) technique with a BIAcore® 2000 instrument (BIAcore® International AB, a GE Healthcare company, Uppsala, Sweden). First, a ~5,500 RU rabbit anti-mouse IgG Capture Biosensor was created by amine-coupling rabbit anti-mouse IgG antibody (BIAcore® International AB, a GE Healthcare company, Uppsala, Sweden) to a CM4 biosensor chip (BIAcore® International AB, a GE Healthcare company, Uppsala, Sweden) via EDC/NHS/Ethanolamine chemistry provided in an Amine Coupling Kit (BIAcore® International AB, a GE Healthcare company, Uppsala, Sweden). Human PlGF-1 monoclonal antibodies and human PlGF-1 antigens were diluted into a running buffer (hereinafter "Running Buffer") composed of HBS-EP buffer (BIAcore® International AB, a GE Healthcare company, Uppsala, Sweden) spiked with 0.1% BSA and 0.1% CM-Dextran. Each human PlGF-1 monoclonal antibody was diluted to 0.2 µg/mL and each human PlGF-1 antigen, namely, CHO-sourced human PlGF-1 (comprising amino acids 1-131; see, SEQ ID NO:1 (A.T.C.C. Accession No. PTA-8537)) and human PlGF-1 fragment (comprising amino acids 17-131 (e.g., 115 amino acids; see SEQ ID NO:5) (A.T.C.C. Accession No. PTA-8540)) (Abbott Laboratories, Abbott Park, Ill.) and *E. coli*-sourced human PlGF-1 (comprising 1-131 (purchased from R&D Systems, Inc., Minneapolis, Minn.), was diluted to concentrations ranging from 0.0457 to 300 nM using a 3-fold dilution series.

After equilibrating the rabbit anti-mouse IgG Capture Biosensor for 5 minutes at 5 µL/minute with Running Buffer, 5 to 10 µL of human PlGF-1 monoclonal antibody was injected over individual flow cells with one flow cell being left blank as a reference flow cell. The flow cells were washed for 6 minutes at 50 µL/minute with Running Buffer before injecting 150 µL of human PlGF-1 or human PlGF-1 fragment antigen at a random concentration across the biosensor, which was immediately followed by 15 minutes of Running Buffer. The biosensor was regenerated with one 30 µL injections of 10 mM Glycine pH 1.7 (BIAcore® International AB, a GE Healthcare company, Uppsala, Sweden) at a flow rate of 10 µL/minute. All concentrations of each human PlGF-1 or human PlGF-1 fragment antigen were tested in duplicate. The binding kinetics, association and dissociation, were monitored via sensorgrams. The sensorgrams were double-referenced and fit to a 1:1 binding model with mass transport using Scrubber 2.0 software (BioLogic Software Pty Ltd., Australia) to determine association and dissociation rates, as well as overall $K_D$. The results are shown below in Table 1.

TABLE 1

| PlGF-1 MAb | PlGF-1 Antigen Source | $k_{on}$* $(M^{-1}s^{-1})$ | $k_{off}$* $(s^{-1})$ | $k_D$* (M) |
|---|---|---|---|---|
| 1-255-713 | CHO 1-131 | $7.3(2) \times 10^4$ | $1.23(2) \times 10^{-4}$ | $1.70(5) \times 10^{-9}$ |
| | CHO 17-131 | $1.82(3) \times 10^5$ | $1.29(1) \times 10^{-4}$ | $7.1(1) \times 10^{-10}$ |
| | E. coli 1-131 | $3.29(6) \times 10^5$ | $1.21(1) \times 10^{-4}$ | $3.68(8) \times 10^{-10}$ |
| 2-826-355 | CHO 1-131 | $6.52(7) \times 10^5$ | $3.25(1) \times 10^{-4}$ | $4.98(6) \times 10^{-10}$ |
| | CHO 17-131 | $1.33(1) \times 10^6$ | $2.91(1) \times 10^{-4}$ | $2.19(2) \times 10^{-10}$ |
| | E. coli 1-131 | $2.34(3) \times 10^6$ | $2.14(1) \times 10^{-4}$ | $9.2(1) \times 10^{-11}$ |

*Standard error of determined values is reported in parentheses with respect to the smallest number place value.

EXAMPLE 11

Measurement of Human PlGF-1 in Various Exemplary Sandwich Immunoassays

A number of antibodies were either raised against human PlGF-1 antigens and produced (namely, monoclonal antibodies 1-255-713 (referred to herein as MAb255) and 2-826-335 (referred to herein as MAb826), described in Examples 7-9 herein) or supplied through a number of different outside vendors. Specifically, the antibodies obtained from outside vendors were rat monoclonal antibody 04 (also referred to herein as MAb04), monoclonal antibody 264 (also referred to herein as MAb264), affinity column purified goat polyclonal antibody pAb264 and recombinant PlGF-1 (comprising amino acids 1-131) expressed in E. coli, all of which were purchased from R&D Systems (Minneapolis, Minn.).

Antibodies MAb04, MAb255, MAb264, and MAb826 were immobilized to magnetic microparticles (Polymer Labs, Amherst, Mass.) by passive coating followed by EDAC cross-linking and for use as the capture antibodies. A goat polyclonal antibody labeled with an acridinium ester or MAb826 labeled with an acridinium ester were used as the detection antibodies.

For these studies, the human PlGF-1 antigen source was E. coli (which produced a human PlGF-1 comprising amino acids 1-131), CHO (which produced a human PlGF-1 comprising amino acids 1-137 (SEQ ID NO:2) or a human PlGF-1 fragment (comprising amino acids 17-131 (SEQ ID NO:5))) or human embryonic kidney cells (which produced a human PlGF-1 comprising amino acids 1-137 (SEQ ID NO:2) or a human PlGF-1 fragment (comprising amino acids 17-131 (SEQ ID NO:5))). Each antigen construct (E. coli, human embryonic kidney cell, and CHO PlGF-1) was first dissolved in a buffer matrix called 'calibrator diluent' (a buffer containing 2-(N-morpholino)ethanesulfonic acid (MES), other salt, a protein blocker and an antimicrobial) to obtain concentrated intermediate stock solutions. Afterwards, six calibrators (identified as Cal A to Cal F, with concentration from 0.0 to 1,500 pg/mL) were prepared by diluting the intermediate stock into the calibrator diluent, using weights measured by an analytical balance.

The assay was carried out by automated ARCHITECT® i2000 analyzer (Abbott Laboratories, Abbott Park, Ill.). Briefly, the assay involved the following steps:

1. Mixing 75 µL of antigen calibrator (Cal A, Cal B, Cal C, Cal D, Cal E, and Cal F) prepared from each human PlGF-1 construct (E. coli, human embryonic kidney cell and CHO) with 50 µL of microparticles coated with anti-human PlGF-1 antibody (namely, MAb04, MAb255, MAb264, and MAb826 respectively).

2. Incubating the reaction mixture for approximately 18 minutes at a maintained ambient temperature of 33-38° C. The human PlGF-1 antigen in the sample bound to the anti-human PlGF-1 antibody on the microparticles.

3. Unbound human PlGF-1 was separated from magnet-detained microparticle and drained into waste. The microparticles were washed with a phosphate buffer.

4. Adding 50 µL of the detection antibody labeled with an acridinium ester (polyclonal goat antibody pAb264 or mouse monoclonal MAb826) to the reaction mixture.

5. Incubating the reaction mixture for approximately 4 minutes at 33-38° C. The anti-human PlGF-1 antibody-acridinium molecule forms a sandwich with human PlGF-1 captured by antibody immobilized on the microparticle.

6. Washing the microparticles with a phosphate buffer.

7. Adding Pre-trigger (acid solution) and Trigger (basic solution) to cause the captured human PlGF-1 to emit light, which was measured by the instrument as Relative Light Units (RLUs). RLUs are the designation for the optical unit of measurement utilized on the ARCHITECT® systems. The ARCHITECT® optics system is essentially a photomultiplier tube (PMT) that performs photon counting on the light emitted by the chemiluminescent reaction. The amount of light generated by the chemiluminescent reaction is proportional to the amount of acridinium tracer present in the reaction mixture, and thereby allows quantitation of the sample analyte that is also proportional to the amount of acridinium remaining in the reaction mixture at the time the chemiluminescent reaction occurs. The term "Relative Light Units" comes from the relation of the photon counting to a certain amount of acridinium. Each optics module is calibrated with a set of acridinium standards. When the chemiluminescent reaction occurs, light is emitted and the photons are measured over a 3 second time period. The PMT converts the photons counted to digital signal, which is then sent to a circuit board for processing. The optics circuit board converts the digital signal from the PMT to an analog signal that is proportional to the photons counted, which is in turn proportional to the amount of acridinium present. This analog signal is then further processed to produce an RLU value. This relationship was established to produce a standard for calibration of the optics module, where the different acridinium standards have RLU values assigned to them. So, while the RLU unit itself is arbitrary, it is proportional (i.e., relative) to a certain amount of acridinium.

Table 2 below shows the results from a human PlGF-1 immunoassay where MAb04 was used as the capture antibody and polyclonal antibody pAB264 was used as the detection antibody.

TABLE 2

| | Microparticle Ab | | | | |
|---|---|---|---|---|---|
| | MAb04 | MAb04 | MAb04 | MAb04 | MAb04 |
| | | | Detection Conjugate Ab | | |
| PlGF-1 (pg/mL) | pAb264 E. Coli (RLU) | pAb264 HEK (1-137) (RLU) | pAb264 HEK (17-131) (RLU) | pAb264 CHO (17-131) (RLU) | pAb264 CHO (1-137) (RLU) |
| 0 | 19041 | 18773 | 18702 | 18881 | 19118 |
| 15 | 51935 | 49710 | 39530 | 34223 | 32085 |
| 60 | 169247 | 159290 | 112195 | 89472 | 80081 |
| 250 | 570025 | 539030 | 382233 | 292914 | 246087 |
| 750 | 1359530 | 1255870 | 957276 | 751782 | 644333 |
| 1500 | 2188020 | 2054010 | 1637900 | 1301040 | 1129770 |

Table 3 below shows the results from a human PlGF-1 immunoassay where MAb255 was used as the capture antibody and polyclonal antibody pAB264 was used as the detection antibody.

TABLE 3

| | Microparticle Ab | | | | |
|---|---|---|---|---|---|
| | MAb255 | MAb255 | MAb255 | MAb255 | MAb255 |
| | | | Detection Conjugate Ab | | |
| PlGF-1 (pg/mL) | pAb264 E. Coli (RLU) | pAb264 HEK (1-137) (RLU) | pAb264 HEK (17-131) (RLU) | pAb264 CHO (17-131) (RLU) | pAb264 CHO (1-137) (RLU) |
| 0 | 14337 | 14197 | 14207 | 14402 | 14524 |
| 15 | 47235 | 46664 | 32940 | 28739 | 26379 |
| 60 | 161152 | 165478 | 106859 | 81229 | 71591 |
| 250 | 543401 | 558975 | 363459 | 283058 | 226231 |
| 750 | 1318490 | 1311810 | 907658 | 712518 | 599081 |
| 1500 | 2192190 | 2143720 | 1618310 | 1246490 | 1051010 |

Table 4 below shows the results from a human PlGF-1 immunoassay where MAb264 was used as the capture antibody and polyclonal antibody pAB264 was used as the detection antibody.

TABLE 4

| | Microparticle Ab | | | | |
|---|---|---|---|---|---|
| | MAb264 | MAb264 | MAb264 | MAb264 | MAb264 |
| | | | Detection Conjugate Ab | | |
| PlGF-1 (pg/mL) | pAb264 E. Coli (RLU) | pAb264 HEK (1-137) (RLU) | pAb264 HEK (17-131) (RLU) | pAb264 CHO (17-131) (RLU) | pAb264 CHO (1-137) (RLU) |
| 0 | 5112 | 4747 | 4881 | 4682 | 4646 |
| 15 | 15634 | 10414 | 8590 | 6874 | 6370 |
| 60 | 54994 | 31320 | 23483 | 14830 | 13774 |
| 250 | 195754 | 108625 | 77870 | 45959 | 38891 |
| 750 | 352417 | 277348 | 206404 | 119501 | 106432 |
| 1500 | 937030 | 507085 | 402849 | 222780 | 200511 |

Table 5 below shows the results from a human PlGF-1 immunoassay where MAb826 was used as the capture antibody and polyclonal antibody pAB264 was used as the detection antibody.

TABLE 5

| | Microparticle Ab | | | | |
|---|---|---|---|---|---|
| | MAb826 | MAb826 | MAb826 | MAb826 | MAb826 |
| | | | Detection Conjugate Ab | | |
| PlGF-1 (pg/mL) | pAb264 E. Coli (RLU) | pAb264 HEK (1-137) (RLU) | pAb264 HEK (17-131) (RLU) | pAb264 CHO (17-131) (RLU) | pAb264 CHO (1-137) (RLU) |
| 0 | 6406 | 6532 | 6587 | 6681 | 6599 |
| 15 | 19630 | 15456 | 12756 | 11181 | 10065 |
| 60 | 65533 | 47721 | 36920 | 28243 | 22171 |
| 250 | 231051 | 173397 | 125686 | 93565 | 66110 |
| 750 | 606073 | 422924 | 336270 | 238842 | 179860 |
| 1500 | 1082570 | 759689 | 624446 | 456336 | 328636 |

Table 5 below snows the results from a human PlGF-1 Immunoassay where MAb255 was used as the capture antibody and monoclonal antibody MAb826 was used as the detection antibody.

TABLE 6

| | Microparticle Ab | | | | |
|---|---|---|---|---|---|
| | MAb255 | MAb255 | MAb255 | MAb255 | MAb255 |
| | | | Detection Conjugate Ab | | |
| PlGF (pg/mL) | MAb826 E. Coli (RLU) | MAb826 HEK (1-137) (RLU) | MAb826 HEK (17-131) (RLU) | MAb826 CHO (17-131) (RLU) | MAb826 CHO (1-137) (RLU) |
| 0 | 6111 | 6114 | 5760 | 5938 | 6270 |
| 15 | 22706 | 26725 | 17195 | 13266 | 14521 |
| 60 | 83204 | 100887 | 57910 | 42063 | 42189 |
| 250 | 298156 | 367219 | 207293 | 143948 | 152791 |
| 750 | 779528 | 889552 | 576466 | 394631 | 399699 |
| 1500 | 1345170 | 1521830 | 1043690 | 750211 | 734140 |

As shown in the above Tables 2-6, the binding of HEK human PlGF-1 fragment 17-131 was comparable to full length HEK human PlGF-1 (1-137) in all five antibody sandwich formats. CHO human PlGF-1 fragment 17-131 and the full length CHO human PlGF-1 1-131 were weaker in binding to the antibodies.

EXAMPLE 12

Sandwich Assay Using Monoclonal Antibodies Produced by Hybridoma Cell Lines 1-255-713 and 2-826-335

Purified human PlGF-1 MAb 1-255-713 was coated on a white 96 well microtiter EIA plate (Nunc Corporation, Rochester N.Y.) at 5 µg/mL. After the capture reagent had been coated on the solid phase, it was removed and any unoccupied binding sites remaining on the plates were blocked using a 2% Fish Gel solution in PBS. The plates were washed and log 2 serial dilutions of recombinant antigen (rAg) lots, starting at 10,000 pg/mL in research phase ARCHITECT® Human PlGF-1 calibrator diluent (which comprises a buffer containing MES, other salt, a protein blocker and an antimicrobial; Abbott Laboratories, Abbott Park, Ill.), were added to the plate for a one-hour incubation. Purified human PlGF-1 rAg (R&D Systems Minneapolis, Minn.) that was produced in E. coli was used as a positive control and purified NGAL) rAg was used as a negative control in this assay. Purified human PlGF-1-His (1-131) and (17-131) rAg, produced in-house in CHO cells, was also tested in this assay. Purified antibody from human PlGF-1 2-826-335 was digested to form Fab'2 fragments, which were acridinium labeled. After washing off the rAg solutions, the labeled Fab'2 fragment diluted to 50 ng/mL in research phase ARCHITECT® cHuman PlGF-1 conjugate diluent (Abbott Laboratories, Abbott Park, Ill.) containing MES, other salt, protein blockers, antimicrobial and detergent was added to the plate and allowed to incubate for 30 minutes. Following this incubation, the plate was washed 4 times with distilled water and dried on paper towels. Luminescence counts per second (LCPS) were measured on a Microbeta Jet instrument (Perkin Elmer, Waltham Mass.). The plate was loaded in the instrument where 100 µl of Architect Pre-trigger Solution (Abbott Laboratories, Abbott Park, Ill.) is added to each well, followed by 100 ul of Architect Trigger Solution is added before flash chemiluminescence is read and recorded. A calibration curve was generated with each rAg and recorded in the following graph. These two MAb reagents were able to successfully form a sandwich with all three human PlGF-1 antigens while only minimal sandwich formation was observed with the highest concentration of the negative control antigen.

EXAMPLE 13

Confirmation of the Assay Ability to Bind Free PlGF

In this Example the ability of an assay using antibodies from murine hybridoma cell lines 1-255-713 and 2-826-335 to bind free human PlGF-1, as opposed to human PlGF-1 complexed with sFlt-1, was investigated.

All reagents were as described in preceding Examples. sFlt-1 calibration antigen (murine myeloma recombinant DNA human sFlt-1 comprising domains 1-3) was Recombinant Human VEGF R1/Flt-1 (aa 27-328)/Fc Chimera (purchased from R&D Systems, Catalog No. 3516-FL]. Native sFlt-1 was isolated from placental tissue using ammonium sulfate fractionation and affinity chromatography on an immobilized heparin column (Pall Membrane) (Roeckl et al., *Exp Cell Res.*, 241:161-170 (1998)).

The human PlGF-1 assay was carried out by incubating samples with concentrations of sFlt-1 of up to 12 nM. Samples containing 54 µM of human PlGF-1 were incubated for 16 hours at from 2 to 8° C. before analysis with the ARCHITECT® assay.

The human PlGF-1 assay was inhibited up to 90% at 12 nM sFlt-1 (data not shown). The 10% residual activity is likely the result of the competition between the PlGF binding to solid phase antibody and the soluble sFlt-1. For human PlGF-1, 90% maximum inhibition required a 40-fold excess of sFlt-1 over human PlGF-1. The various binding reactions in the initial incubation eventually reach steady state equilibrium that is unaffected by increasing the sFlt-1 concentration. If a sample containing a mixture of free human PlGF-1, sFlt-1 and complexed human PlGF-1/sFlt-1 is incubated for a period of time with immobilized capture human PlGF-1 antibody, the measured sFlt-1 concentration increases. This suggests that stripping of the human PlGF-1 bound to sFlt-1 has occurred.

In Table 7 below, a full factorial of concentrations of sFlt-1 was assayed within the measurement ranges of the human PlGF-1 assay. The percentage of inhibition is indicated in parenthesis. The levels measured to assess the relative impact of sFlt-1 on human PlGF-1 are consistent with what can be expected for pregnant women in the second and third trimester (data not shown). From the titration completed as described above, a maximum of 90% inhibition of human PlGF-1 by sFlt-1 could be expected. However the maximum inhibition is 80% and is observed for a higher concentration of human PlGF-1. This maximum inhibition occurs at the highest concentration measured for human PlGF-1 at a molar ratio of 29, and not at the lower concentration of human PlGF-1 with a molar ratio of 330. These data reflect the complexity of the assay. There is competition for the human PlGF-1 by the antibody on the solid phase as well as the sFlt-1 in solution. The concentrations of the soluble proteins are on the same order of magnitude of the dissociation constants. Added to that is the impact of avidity derived from the density of immobilized anti-human PlGF-1 antibody on the particles.

TABLE 7

| | Measured Human PlGF-1 Added sFlt-1, pM | | | | | |
|---|---|---|---|---|---|---|
| 0 | 93 | 186 | 389 | 788 | 1,181 | |
| 3.6 pM | 1.5 pM (−58%) | 1.2 pM (−65%) | 1.2 pM (−67%) | 1.2 pM (−66%) | 1.3 pM (−64%) | |
| 6.8 pM | 3.1 pM (−55%) | 2.4 pM (−65%) | 2.0 pM (−70%) | 1.9 pM (−72%) | 1.9 pM (−72%) | |
| 13.3 pM | 6.7 pM (−49%) | 4.9 pM (−63%) | 3.8 pM (−72%) | 3.3 pM (−76%) | 3.0 pM (−77%) | |
| 27.1 pM | 15.6 pM (−42%) | 10.6 pM (−61%) | 7.5 pM (−72%) | 6.1 pM (−78%) | 5.4 pM (−80%) | |
| 40.5 pM | 25.9 pM (−36%) | 17.8 pM (−56%) | 12.2 pM (−70%) | 9.2 pM (−77%) | 7.8 pM (−81%) | |

These results confirm that the ARCHITECT® assay described herein for human PlGF-1 measures predominantly the uncomplexed form of the protein. The equilibrium of two proteins (human PlGF-1 and sFlt-1) can be perturbed both in vivo and in vitro (during the assay). The antibodies used to capture the proteins can affect the equilibrium and therefore the end result. More importantly it is clear that sFlt-1 can act as a "sink" for sequestering human PlGF-1. High concentrations of sFlt-1 can have a significant impact on the circulating levels of human PlGF-1.

It similarly appears that the binding of the commercially available monoclonal antibody 264 (MAB264) recognizes free PlGF-1 since its binding is inhibited by sFlt-1 and the recognition site of the antibody on PlGF-1 is similar to the region described in publications as for sFlt-1 binding (data not shown).

EXAMPLE 14

Comparison of Three Human PlGF-1 Assay Formats to Detect Free Human PlGF-1

The inhibition by sFlt-1 was evaluated in three assay formats to determine the relative ability of each assay to detect human PlGF-1/sFlt-1 complex or uncomplexed human PlGF-1. Format 1 utilizes human PlGF-1 MAb 2-826-335 as the capture reagent immobilized on paramagnetic microparticles and human PlGF-1 MAb 1-255-713 as the detection reagent labeled with acridinium. Format 2 utilizes PlGF-1 MAb264 as the capture reagent immobilized on paramagnetic microparticles and human PlGF-1 Pb264 as the detection reagent labeled with acridinium. Formats 1 and 2 are tested in the ARCHITECT® i2000 assay format as described in Example 11. Format 3 is the Quantikine® Human PlGF ELISA purchased from R&D Systems which utilizes PlGF-1 MAb264 as the capture reagent immobilized on 96 well microtiter plate and PlGF-1 Pb264 as the detection reagent. PlGF-1 purchased from R&D Systems was used as calibrator material for both assay formats.

Normal human plasma was spiked with approximately 950 pg/mL purified human PlGF-1 (1-131) expressed in HEK cells. Native sFlt-1, isolated from human placental tissue, was added to the spiked human PlGF-1 plasma up to a 300-fold molar excess over human PlGF-1. The human PlGF-1 and sFlt-1 spiked plasma was incubated for 1-2 hours at ambient temperature prior to testing in the ARCHITECT® and microtiter plate assays.

The results are shown in Table 8 below. The % Inhibition is calculated based on the measured concentration in the absence of sFlt-1 for each respective assay format. Both ARCHITECT® assay formats reach 90% inhibition between 20 and 30-fold molar excess of sFlt-1 over human PlGF-1. These results demonstrate that both assay formats are inhibited by sFlt-1 binding to human PlGF-1 and therefore are able to detect free or uncomplexed human PlGF-1.

to about 50 (e.g., about 2.5, about 5, about 10, about 20, about 30, about 40, or about 50), automated/semi-automated Formats 1 and 2 exhibit inhibition of the measured PlGF-1 value where the inhibition is from about 1.5 to about 2 times greater than the inhibition of the measured PlGF-1 that is obtained using a non-automated ELISA. This suggests that the automated assay Formats as described herein are better at detecting free PlGF-1 than is the non-automated ELISA.

EXAMPLE 15

Alternate Immunoassay Format for Human PlGF-1

This Example describes an alternate immunoassay format to that set forth in Example 12.

This Example employs an ARCHITECT® immunoassay format for detection of human PlGF-1 that utilizes PlGF-1 MAb 2-826-335 as the capture reagent immobilized on paramagnetic microparticles and PlGF-1 MAb 1-255-713 or 1-255-2675 as the conjugate reagent labeled with acridinium. The conjugate reagent may be either an intact IgG MAb, an F(ab')2, or Fab fragment. The ARCHITECT assay was run as described in Example 11. A range of sample volumes from 50 to 100 microliters were used during optimization of the assay. The exemplary sample volume is 50 to 75 microliters, and the optimal sample volume is 50 microliters. PlGF-1 purchased from R&D Systems was used as calibrator material for the assay. Calibrators are prepared at PlGF-1 concentrations of 0, 10, 30, 60, 500, and 1,500 pg/mL.

TABLE 8

| | | PlGF-1 Assay Format | | | | | |
|---|---|---|---|---|---|---|---|
| sFlt- | | Format 1 (ARCHITECT) | | Format 2 (ARCHITECT) | | Format 3 (ELISA) | |
| 1:PlGF-1 Molar Ratio | sFlt-1 Added (pmol/L) | PlGF-1 Measured (pg/mL) | % Inhibition | PlGF-1 Measured (pg/mL) | % Inhibition | PlGF-1 Measured (pg/mL) | % Inhibition |
| 0 | 0 | 1021.2 | 0.0 | 786.5 | 0.0 | 865.0 | 0.0 |
| 2.5 | 77 | 593.8 | 41.9 | 494.0 | 37.2 | 706.9 | 18.3 |
| 5 | 153 | 366.6 | 64.1 | 276.2 | 64.9 | 652.1 | 24.6 |
| 10 | 307 | 196.6 | 80.7 | 143.0 | 81.8 | 583.2 | 32.6 |
| 20 | 613 | 119.5 | 88.3 | 82.9 | 89.5 | 515.3 | 40.4 |
| 30 | 920 | 95.1 | 90.7 | 68.2 | 91.3 | 475.5 | 45.0 |
| 40 | 1227 | 83.2 | 91.9 | 55.5 | 92.9 | 416.9 | 51.8 |
| 50 | 1533 | 76.6 | 92.5 | 50.4 | 93.6 | 414.7 | 52.1 |
| 75 | 2300 | 65.0 | 93.6 | 39.7 | 95.0 | 208.6 | 75.9 |
| 100 | 3067 | 60.3 | 94.1 | 33.8 | 95.7 | 165.6 | 80.9 |
| 150 | 4600 | 51.3 | 95.0 | 27.5 | 96.5 | 159.1 | 81.6 |
| 300 | 9200 | 42.1 | 95.9 | 20.0 | 97.5 | 153.6 | 82.2 |

As can be seen from Table 8, the R&D Systems ELISA format does not reach 90% inhibition with as much as 300-fold molar excess of sFlt-1 over human PlGF-1. The antibodies used in Formats 2 and 3 are the same but the two formats are not inhibited to the same degree as shown in Table 8. The ELISA in Format 3 was run according to the package insert which uses a 2 hour incubation with sample and capture reagent (MAb264) whereas the ARCHITECT® has an approximately 18 min incubation time. Similarly, the ELISA in Format 3 incubates the detection reagent (Pb264) for 2 hours whereas the ARCHITECT® has an approximately 4 min incubation time at this step. The differences in inhibition between Formats 2 and 3 are likely due to the timing differences in the two assay formats.

Regardless of the mechanism underlying this difference, within a range of sFlt-1:PlGF molar ratios of from about 2.5

The immunoassay format as described in this Example was used to measure PlGF-1 in 400 apparently normal individuals. The specimens were purchased from ProMedDx, LLC (Norton, Mass.) and comprised of 200 males and 200 females. The specimens were collected in either EDTA plasma or serum collection tubes. The results of testing are shown in Table 9, below.

TABLE 9

| Sample size | 400 |
|---|---|
| Median | 16.0 |
| Lowest value | 7.9 |
| Highest value | 29.8 |
| Geometric mean | 16.1 |
| Kolmogorov-Smirnov test | accept Normality (P = 0.751) |

TABLE 9-continued for Normal distribution

| Percentiles | |
|---|---|
| 0.5 | 9.7 |
| 2.5 | 10.7 |
| 5 | 11.1 |
| 25 | 13.9 |
| 75 | 18.6 |
| 95 | 23.6 |
| 97.5 | 25.8 |
| 99.5 | 28.0 |

Values back-transformed after logarithmic transformation.

As can be seen from Table 9, the median PlGF concentration is 16.0 pg/mL and the upper 97.5 percentile is 25.8 pg/mL. The lowest sample is 7.9 pg/mL and the highest value is 29.8 pg/mL in this sample set.

Figure 22:
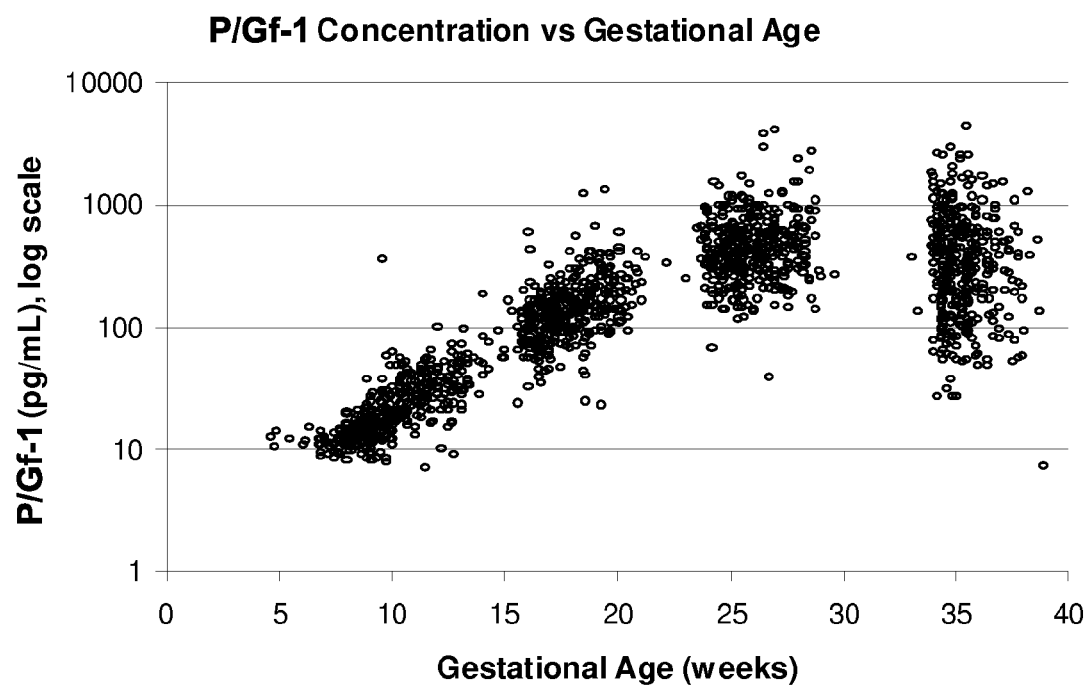
FIG. 22 is a plot of PlGF concentration versus gestational age for an exemplary PlGF-1 immunoassay format as described in Example 15.

The exemplary immunoassay format was used to measure PlGF in pregnant individuals with gestational age ranging from 4.5 to 39 weeks. The specimens were collected in EDTA plasma. The results are shown in FIG. 22 (N=1,490 specimens). As can be seen from FIG. 22, a steady increase in PlGF value is observed with increasing gestational age up to approximately 30 weeks. After approximately 32 weeks, the PlGF values are widely scattered. The PlGF concentration in these specimens ranges from approximately 7.0 pg/mL to approximately 4,500 pg/mL. Specimens with initial values greater than 1,500 pg/mL were retested after a 4-fold dilution to provide a result within the calibration range.

These results confirm that the exemplary immunoassay format as described herein is able to detect human PlGF-1 in pregnant individuals. Studies have also been done and results successfully obtained using this immunoassay format in individuals with preeclampsia, patients with cardiac conditions, and patients with carcinoma such as renal cell carcinoma, hepatocellular carcinoma, and non small cell lung carcinoma (data not shown).

EXAMPLE 16

ATCC Deposit Information

Murine hybridoma cell lines 1-255-713 and 2-826-335 were deposited with the American Type Culture Collection (hereinafter referred to as "A.T.C.C"), 10801 University Blvd., Manassas, Va. 20110-2209, on Jul. 12, 2007. Cell line 1-255-713 was assigned A.T.C.C. Accession No. PTA-8536. Cell line 2-826-335 was assigned A.T.C.C. Accession No. PTA-8539.

Chinese Hamster Ovary recombinant antigen cell lines ("CHO 350") expressing human PlGF-1-enterokinase (EK) (1-131) was deposited with the A.T.C.C. on Jul. 12, 2007 and assigned A.T.C.C. Accession No. PTA-8537 (This is full length human PlGF-1 1-131 with a His tag that is removed with the EK cleavage site) Chinese Hamster Ovary recombinant antigen cell lines ("CHO 6305") containing human PlGF-1-histidine tag (1-131) was deposited with the A.T.C.C. on Jul. 12, 2007 and assigned A.T.C.C. Accession No. PTA-8538.

Chinese Hamster Ovary recombinant antigen cell lines ("CHO 886") human PlGF-1 fragment (17-131) was deposited with the A.T.C.C. on Jul. 12, 2007 and assigned A.T.C.C. Accession No. PTA-8540.

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated antibody that specifically binds to human type 1 placental growth factor (PlGF-1) or human PlGF-1 fragment, wherein said antibody:
   (a) has a variable heavy domain region comprising the amino acid sequence of SEQ ID NO:32;
   (b) has a variable light domain region comprising the amino acid sequence of SEQ ID NO:29; or
   (c) has a variable heavy domain region comprising the amino acid sequence of SEQ ID NO:32 and a variable light domain region comprising the amino acid sequence of SEQ ID NO:29.

2. An isolated antibody that specifically binds to human PlGF-1 or human PlGF-1 fragment, wherein said antibody:
   (a) has a variable heavy domain region comprising the amino acid sequence of SEQ ID NO:35;
   (b) has a variable light domain region comprising the amino acid sequence of SEQ ID NO:43; or
   (c) has a variable heavy domain region comprising the amino acid sequence of SEQ ID NO:35 and a variable light domain region comprising the amino acid sequence of SEQ ID NO:43.

3. A murine hybridoma cell line selected from the group consisting of a cell line 1-255-713 having ATCC Accession No. PTA-8536 and a cell line 2-826-335 having ATCC Accession No. PTA-8539.

4. An antibody selected from the group consisting of an antibody produced by murine hybridoma cell line 1-255-713 having ATCC Accession No. PTA-8536 and an antibody produced by murine hybridoma cell line 2-826-335 having ATCC Accession No. PTA-8539.

5. An immunodiagnostic reagent comprising one or more antibodies selected from the group consisting of:
   (a) an isolated antibody that specifically binds to human PlGF-1 or human PlGF-1 fragment, wherein said antibody has a variable heavy domain region comprising the amino acid sequence of SEQ ID NO:32;
   (b) an isolated antibody that specifically bind to human PlGF-1 or human PlGF-1 fragment, wherein said antibody has a variable light domain region comprising the amino acid sequence of SEQ ID NO:29;
   (c) an isolated antibody that specifically binds to human PlGF-1 or human PlGF-1 fragment, wherein said antibody has a variable heavy domain region comprising the amino acid sequence of SEQ ID NO:32 and a variable light domain region comprising the amino acid sequence of SEQ ID NO:29;
   (d) an antibody produced by murine hybridoma cell line 1-255-713 having ATCC Accession No. PTA-8536;
   (e) an isolated antibody that specifically binds to human PlGF-1 or human PlGF-1 fragment, wherein said antibody has a variable heavy domain region comprising the amino acid sequence of SEQ ID NO:35;
   (f) an isolated antibody that specifically bind to human PlGF-1 or human PlGF-1 fragment, wherein said antibody has a variable light domain region comprising the amino acid sequence of SEQ ID NO:43;
   (g) an isolated antibody that specifically binds to human PlGF-1 or human PlGF-1 fragment, wherein said antibody has a variable heavy domain region comprising the amino acid sequence of SEQ ID NO:35 and a variable light domain region comprising the amino acid sequence of SEQ ID NO:43; and
   (h) an antibody produced by murine hybridoma cell line 2-826-335 having ATCC Accession No. PTA-8539.

6. An isolated or purified glycosylated human PlGF-1 or glycosylated human PlGF-1 fragment, wherein said glycosylated human PlGF-1 or glycosylated human PlGF-1 fragment comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

7. An isolated or purified deglycosylated human PlGF-1 or deglycosylated human PlGF-1 fragment wherein at least one asparagine residue of glycosylated human PlGF-1 or glycosylated human PlGF-1 fragment is converted to an aspartic acid residue as a result of the deglycosylation.

8. An isolated or purified deglycosylated human PlGF-1 or deglycosylated human PlGF-1 fragment, wherein said deglycosylated human PlGF-1 or deglycosylated human PlGF-1 fragment comprises a sequence selected from the group consisting of: SEQ ID NO:36, SEQ ID NO:37, SEQ ID NO:38, SEQ ID NO:39 and SEQ ID NO:40.

9. A calibrator or control for use in an assay for detecting human PlGF-1 in a test sample, said calibrator or control being a composition comprising a known amount of deglycosylated human PlGF-1 or deglycosylated human PlGF-1 fragment.

10. The calibrator or control of claim 9, wherein said deglycosylated human PlGF-1 or deglycosylated human PlGF-1 fragment comprises a sequence selected from the group consisting of: SEQ ID NO:1, SEQ ID NO:2, SEQ ID NO:3, SEQ ID NO:4, SEQ ID NO:36, SEQ ID NO:37, SEQ ID NO:38, SEQ ID NO:39 and SEQ ID NO:40.

11. An isolated or purified human PlGF-1 or human PlGF-1 fragment selected from the group consisting of:
(a) an isolated or purified human PlGF-1 or human PlGF-1 fragment comprising a sequence selected from the group consisting of a polypeptide wherein: (i) amino acid residue 21 of SEQ ID NO:2 is converted from asparagine to aspartic acid as compared to the wild-type sequence; and (ii) amino acid residue 89 of SEQ ID NO:2 is converted from asparagine to aspartic acid as compared to the wild-type sequence;
(b) an isolated or purified human PlGF-1 or human PlGF-1 fragment comprising a sequence selected from the group consisting of a polypeptide wherein: (i) amino acid residue 15 of SEQ ID NO:1 is converted from asparagine to aspartic acid as compared to the wild-type sequence; and (ii) amino acid residue 83 of SEQ ID NO:1 is converted from asparagine to aspartic acid as compared to the wild-type sequence;
(c) an isolated or purified human PlGF-1 or human PlGF-1 fragment wherein one or more asparagine residues at position 21, position 89 or position 21 and 89 of SEQ ID NO:2 is glycosylated with at least one N-glycan having a structure selected from the group consisting of: (a) N-acetylneuraminic acid(Galactose)$_2$(Mannose)$_3$(N-acetyl-D-glucosamine)$_4$Fucose, (b) (N-acetylneuraminic acid)$_2$(Galactose)$_2$(Mannose)$_3$(N-acetyl-D-glucosamine)$_4$Fucose, (c) (N-acetylneuraminic acid)$_2$(Galactoseβ1-4N-acetyl-D-glucosamine)$_2$(Galactose)$_2$(Mannose)$_3$(N-acetyl-D-glucosamine)$_4$Fucose or (Galactoseβ1-4N-acetyl-D-glucosamine)(Galactose)$_3$(Mannose)$_3$(N-acetyl-D-glucosamine)$_5$Fucose; (d) (N-acetylneuraminic acid)$_2$(Galactose)$_3$(Mannose)$_3$(N-acetyl-D-glucosamine)$_5$Fucose; (e) (N-acetylneuraminic acid)$_3$(Galactose)$_3$(Mannose)$_3$(N-acetyl-D-glucosamine)$_5$Fucose; (f) (N-acetylneuraminic acid)$_3$(Galactoseβ1-4N-acetyl-D glucosamine)(Galactose)$_3$(Mannose)$_3$(N-acetyl-D-glucosamine)$_5$Fucose or (N-acetylneuraminic acid)$_3$(Galactose)$_4$(Mannose)$_3$(N-acetyl-D-glucosamine)$_6$Fucose; (g) (N-acetylneuraminic acid)$_4$(Galactose)$_4$(Mannose)$_3$(N-acetyl-D-glucosamine)$_6$Fucose;
and (h) (N-acetylneuraminic acid)$_4$(Galactoseβ1-4N-acetyl-D-glucosamine)(Galactose)$_4$(Mannose)$_3$(N-acetyl-D-glucosamine)$_6$Fucose; and
(d) an isolated or purified human PlGF-1 or human PlGF-1 fragment wherein one or more asparagine residues at position 15, position 83 or position 15 and 83 of SEQ ID NO:1 is glycosylated with at least one N-glycan having a structure selected from the group consisting of: (a) N-acetylneuraminic acid(Galactose)$_2$(Mannose)$_3$(N-acetyl-D-glucosamine)$_4$Fucose, (b) (N-acetylneuraminic acid)$_2$(Galactose)$_2$(Mannose)$_3$(N-acetyl-D-glucosamine)$_4$Fucose, (c) (N-acetylneuraminic acid)$_2$(Galactoseβ1-4N-acetyl-D-glucosamine)$_2$(Galactose)$_2$(Mannose)$_3$(N-acetyl-D-glucosamine)$_4$Fucose or (Galactoseβ1-4N-acetyl-D-glucosamine)(Galactose)$_3$(Mannose)$_3$(N-acetyl-D-glucosamine)$_5$Fucose; (d) (N-acetylneuraminic acid)$_2$(Galactose)$_3$(Mannose)$_3$(N-acetyl-D-glucosamine)$_5$Fucose; (e) (N-acetylneuraminic acid)$_3$(Galactose)$_3$(Mannose)$_3$(N-acetyl-D-glucosamine)$_5$Fucose; (f) (N-acetylneuraminic acid)$_3$(Galactoseβ1-4N-acetyl-D glucosamine)(Galactose)$_3$(Mannose)$_3$(N-acetyl-D-glucosamine)$_5$Fucose or (N-acetylneuraminic acid)$_3$(Galactose)$_4$(Mannose)$_3$(N-acetyl-D-glucosamine)$_6$Fucose; (g) (N-acetylneuraminic acid)$_4$(Galactose)$_4$(Mannose)$_3$(N-acetyl-D-glucosamine)$_6$Fucose;
and (h) (N-acetylneuraminic acid)$_4$(Galactoseβ1-4N-acetyl-D glucosamine)(Galactose)$_4$(Mannose)$_3$(N-acetyl-D-glucosamine)$_6$Fucose.

12. A diagnostic kit for the detection of human PlGF-1 or human PlGF-1 fragment, the kit comprising:
(a) at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539; and
(b) instructions for using said kit.

13. The kit of claim 12, wherein the kit further comprises a calibrator or control comprising glycosylated or deglycosylated human PlGF-1 or glycosylated or deglycosylated human PlGF-1 fragment selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

14. A diagnostic kit for the detection of human PlGF-1 or human PlGF-1 fragment, the kit comprising:
(a) at least one calibrator or control comprising glycosylated or deglycosylated human PlGF-1 or glycosylated or deglycosylated human PlGF-1 fragment selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; and
(b) instructions for using said kit.

15. The kit of claim 14, wherein the kit further comprises at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539.

16. A diagnostic kit for the detection of human PlGF-1 or human PlGF-1 fragment, the kit comprising:
(a) at least one antibody selected from the group consisting of antibody produced by murine hybridoma cell line 1-255-713 having ATCC Accession No. PTA-8536 and an antibody produced by murine hybridoma cell line 2-826-335 having ATCC Accession No. PTA-8539;
(b) at least one calibrator or control comprising glycosylated or deglycosylated human PlGF-1 or glycosylated or deglycosylated human PlGF-1 fragment selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; and
(c) instructions for using said kit.

17. An isolated or purified polypeptide selected from the group consisting of SEQ ID NO: 29, SEQ ID NO: 32, SEQ ID NO: 35, and SEQ ID NO: 43.

18. An isolated antibody that specifically binds to human PlGF-1 or human PlGF-1 fragment, wherein said antibody:
(a) has a variable heavy domain region comprising the complementarity determining region (CDR) H1, the CDR H2, and the CDR H3 of SEQ ID NO: 32,
(b) has a variable light domain region comprising the CDR L1, the CDR L2, and the CDR L3 of SEQ ID NO: 29, or (c) has a variable heavy domain region comprising the CDR H1, the CDR H2, and the CDR H3 of SEQ ID NO: 32 and a variable light domain region comprising the CDR L1, the CDR L2, and the CDR L3 of SEQ ID NO: 29.

19. An isolated antibody that specifically binds to human PlGF-1 or human PlGF-1 fragment, wherein said antibody:
   (a) has a variable heavy domain region comprising the CDR H1, the CDR H2, and the CDR H3 of SEQ ID NO: 35,
   (b) has a variable light domain region comprising the CDR L1, the CDR L2, and the CDR L3 of SEQ ID NO: 43, or
   (c) has a variable heavy domain region comprising the CDR H1, the CDR H2, and the CDR H3 of SEQ ID NO: 35 and a variable light domain region comprising the CDR L1, the CDR L2, and the CDR L3 of SEQ ID NO: 43.

20. A diagnostic kit for the detection of human PlGF-1 or human PlGF-1 fragment, the kit comprising:
   (a) at least one antibody, wherein said antibody;
      (i) has a variable heavy domain region comprising the complementarity determining region (CDR) H1, the CDR H2, and the CDR H3 of SEQ ID NO:32;
      (ii) has a variable light domain region comprising the CDR L1, the CDR L2, and the CDR L3 of SEQ ID NO:29;
      (iii) has a variable heavy domain region comprising the CDR H1, the CDR H2, and the CDR H3 of SEQ ID NO:32 and a variable light domain region comprising the CDR L1, the CDR L2, and the CDR L3 of SEQ ID NO:29;
      (iv) has a variable heavy domain region comprising the CDR H1, the CDR H2, and the CDR H3 of SEQ ID NO:35;
      (v) has a variable light domain region comprising the CDR L1, the CDR L2, and the CDR L3 of SEQ ID NO:43; or
      (vi) has a variable heavy domain region comprising the CDR H1, the CDR H2, and the CDR H3 of SEQ ID NO:35 and a variable light domain region comprising the CDR L1, the CDR L2, and the CDR L3 of SEQ ID NO:43; and
   (b) instructions for using said kit.

* * * * *